(12) United States Patent
Chen

(10) Patent No.: US 9,945,847 B2
(45) Date of Patent: Apr. 17, 2018

(54) IMMUNOASSAYS USING OVER-LABELED FLUORESCENT PROBES

(71) Applicant: ASSAYPRO, LLC, Saint Charles, MO (US)

(72) Inventor: Henry J. X. Chen, Saint Charles, MO (US)

(73) Assignee: ASSAYPRO, LLC, St. Charles, MO (US)

( * ) Notice: Subject to any disclaimer, the term of this patent is extended or adjusted under 35 U.S.C. 154(b) by 113 days.

(21) Appl. No.: 14/493,963

(22) Filed: Sep. 23, 2014

(65) Prior Publication Data
US 2015/0111776 A1    Apr. 23, 2015

Related U.S. Application Data

(60) Provisional application No. 62/029,159, filed on Jul. 25, 2014, provisional application No. 61/889,762, filed on Oct. 11, 2013, provisional application No. 61/881,255, filed on Sep. 23, 2013.

(51) Int. Cl.
| | | |
|---|---|---|
| *G01N 33/543* | (2006.01) | |
| *G01N 33/68* | (2006.01) | |
| *G01N 33/58* | (2006.01) | |

(52) U.S. Cl.
CPC ..... *G01N 33/54306* (2013.01); *G01N 33/582* (2013.01); *G01N 33/6845* (2013.01); *G01N 33/6854* (2013.01); *G01N 2458/00* (2013.01)

(58) Field of Classification Search
None
See application file for complete search history.

(56) References Cited

U.S. PATENT DOCUMENTS

| | | | | |
|---|---|---|---|---|
| 4,444,879 A | * | 4/1984 | Foster | G01N 33/545 422/400 |
| 4,923,819 A | | 5/1990 | Fernandez et al. | |
| 8,357,495 B2 | | 1/2013 | Mattingly et al. | |
| 2005/0069962 A1 | | 3/2005 | Archer et al. | |
| 2006/0269962 A1 | * | 11/2006 | Watkins | G01N 33/537 435/6.16 |
| 2007/0148707 A1 | | 6/2007 | Kovalenko | |
| 2008/0200562 A1 | | 8/2008 | Yin et al. | |
| 2009/0123948 A1 | | 5/2009 | Cho-Chung et al. | |
| 2013/0165335 A1 | | 6/2013 | Lea | |

OTHER PUBLICATIONS

Darwish (International Journal of Biomedical Science, pp. 217-235, 2006).*
International Search Report PCT/US2014/057027 dated Jan. 9, 2015, 15 pages.
European Search Report from related European Application No. EP 14845825.0, dated Apr. 25, 2017; 12 pgs.
"Guide to Antibody Labeling and Detection", BIOMOL GmbH, Jul. 1, 2010, Innova Biosciences Ltd, Cambridge UK, 9 pgs.
Markiv et al., "Expression of recombinant multi-coloured fluorescent antibodies in gor-/trxB-*E. coli* cytoplasm", BMC Biotechnology, 2011, 10 pgs., vol. 11, No. 1.
Song et al., "Development of a Novel Fluorophore for Real-Time Biomonitoring System", PLOS One, 2012, e48459, pp. 1-10, vol. 7, No. 11.
Theilacker et al., "Multiplexed protein analysis using encoded antibody-conjugated microbeads", Journal of The Royal Society Interface, 2011, pp. 1104-1113, vol. 8, No. 61.

* cited by examiner

*Primary Examiner* — Lisa V Cook

(74) *Attorney, Agent, or Firm* — Polsinelli PC

(57) ABSTRACT

The present disclosure provides immunoassays using one or more over-labeled fluorescent probes, which provides for rapid, accurate and quantitative detection of one or more target analytes in sample, reading fluorescent intensity. The disclosed immunoassays provide multiplexing capability with low cross-reactivity.

16 Claims, 85 Drawing Sheets

Current Dye conjugation to antibody. We screen dyes to find the dyes can allow over label with dyes.

Fluorescent peptide conjugation to antibody scheme using Protocol A.

Fluorescent BSA conjugation to antibody scheme using Protocol A.

Fluorescent BSA conjugation to antibody scheme using Protocol B.

Fluorescent BSA conjugation to antibody scheme using Protocol C.

Assay Summary
Add 25 µl of standard/samples
and 25 µl of biotinylated protein per well.
Incubate 1 hour.
Wash, then add 50 µl of SP per well.
Incubate 30 minutes.
Wash, then add 50 µl of Chromogen Substrate per well.
Incubate 15 minutes.
Add 50 µl of Stop Solution per well.
Read at 450 nm immediately.
Figure 58

Assay Summary
Add 50 µl of standard/sample
and 50 µl of fluorescent probe per well.
Incubate 20 minutes.
Wash, then add 50 µl of reagent grade water to each well.
Read at an excitation wavelength of 620 nm and an emission wavelength of 660 nm.
Figure 59

Assay Summary
Add 50 μl of standard/sample
and 50 μl of fluorescent probe per well.
Incubate 20 minutes.
Wash, then add 50 μl of reagent grade water to each well.
Read at an excitation wavelength of 488 nm and an emission wavelength of 576 nm.
Figure 60

Assay Summary
Add 50 μl of standard/sample
and 50 μl of fluorescent probe per well.
Incubate 20 minutes.
Wash, then add 50 μl of reagent grade water to each well.
Read at an excitation wavelength of 620 nm and an emission wavelength of 660 nm.
Figure 61

Assay Summary
Add 50 μl of standard/sample
and 50 μl of fluorescent probe per well.
Incubate 20 minutes.
Wash, then add 50 μl of reagent grade water to each well.
Read at an excitation wavelength of 488 nm and an emission wavelength of 576 nm.
Figure 62

Assay Summary
Add 25 μl of standard/sample
and 25 μl of biotinylated protein per well.
Incubate 1 hour.
Wash, then add 50 μl of SP per well.
Incubate 30 minutes.
Wash, then add 50 μl of Chromogen Substrate per well.
Incubate 12 minutes.
Add 50 μl of Stop Solution per well.
Read at 450 nm immediately.
Figure 63

*Assay Summary*
Add 50 µl of standard/sample
and 50 µl of fluorescent probe per well.
Incubate 20 minutes.
Wash, then add 50 µl of reagent grade water to each well.
Read at an excitation wavelength of 620 nm and an emission wavelength of 660 nm.
Figure 64

Assay Summary
Add 50 µl of standard/sample
and 50 µl of fluorescent probe per well.
Incubate 20 minutes.
Wash, then add 50 µl of reagent grade water to each well.
Read at an excitation wavelength of 488 nm and an emission wavelength of 576 nm.
Figure 65

Assay Summary
Add 50 μl of standard/sample
and 50 μl of fluorescent probe per well.
Incubate 20 minutes.
Wash, then add 50 μl of reagent grade water to each well.
Read at an excitation wavelength of 620 nm and an emission wavelength of 660 nm.
Figure 66

Assay Summary
Add 50 µl of standard/sample
and 50 µl of fluorescent probe per well.
Incubate 20 minutes.
Wash, then add 50 µl of reagent grade water to each well.
Read at an excitation wavelength of 488 nm and an emission wavelength of 576 nm.
Figure 67

Assay Summary
Add 50 μl of standard/sample per well.
Incubate 2 hours.
Wash, then add 50 μl of biotinylated antibody per well.
Incubate 1 hour.
Wash, then add 50 μl of SP per well.
Incubate 30 minutes.
Wash, then add 50 μl of Chromogen Substrate per well.
Incubate 10 minutes.
Add 50 μl of Stop Solution per well.
Read at 450 nm immediately.
Figure 68

Assay Summary
Add 100 µl of standard/sample per well.
Incubate 20 minutes.
Wash, then add 100 µl of fluorescent probe per well.
Incubate 20 minutes.
Wash, then add 50 µl of reagent grade water to each well.
Read at an excitation wavelength of 488 nm and an emission wavelength of 530 nm.
Figure 69

Assay Summary
Add 100 µl of standard/sample per well.
Incubate 20 minutes.
Wash, then add 100 µl of fluorescent probe per well.
Incubate 20 minutes.
Wash, then add 50 µl of reagent grade water to each well.
Read at an excitation wavelength of 594 nm and an emission wavelength of 624 nm.
Figure 70

Assay Summary

Add 100 µl of standard/sample per well.

Incubate 20 minutes.

⇩

Wash, then add 100 µl of fluorescent probe per well.

Incubate 20 minutes.

⇩

Wash, then add 50 µl of reagent grade water to each well.

⇩

Read at an excitation wavelength of 620 nm and an emission wavelength of 661 nm.

Figure 71

Assay Summary
Add 100 μl of standard/sample per well.
Incubate 20 minutes.
Wash, then add 100 μl of fluorescent probe per well.
Incubate 20 minutes.
Wash, then add 50 μl of reagent grade water to each well.
Read at an excitation wavelength of 488 nm and an emission wavelength of 576 nm.
Figure 72

Assay Summary

Add 100 µl of standard/sample per well.

Incubate 20 minutes.

Wash, then add 100 µl of fluorescent probe per well.

Incubate 20 minutes.

Wash, then add 50 µl of reagent grade water to each well.

Read the fluorescence on a microplate reader at an excitation wavelength of 488 nm and an emission wavelength of 530 nm to obtain data for C5. Then, read the fluorescence at an excitation wavelength of 594 nm and an emission wavelength of 624 nm to obtain data for C6.

Figure 73

Assay Summary

Add 100 µl of standard/sample per well.

Incubate 20 minutes.

Wash, then add 100 µl of fluorescent probe per well.

Incubate 20 minutes.

Wash, then add 50 µl of reagent grade water to each well.

Read the fluorescence on a microplate reader at an excitation wavelength of 488 nm and an emission wavelength of 530 nm to obtain data for C6. Then, read the fluorescence at an excitation wavelength of 594 nm and an emission wavelength of 624 nm to obtain data for C5.

Figure 74

Assay Summary

Add 100 µl of standard/sample per well.

Incubate 20 minutes.

Wash, then add 100 µl of fluorescent probe per well.

Incubate 20 minutes.

Wash, then add 50 µl of reagent grade water to each well.

Read the fluorescence on a microplate reader at an excitation wavelength of 488 nm emission wavelength of 576 nm to obtain data for C6 RPE. Then, read the fluorescence at an excitation wavelength of 620 nm emission wavelength of 661 nm to obtain data for C5 APC.

Figure 75

Assay Summary

Add 100 µl of standard/sample per well.

Incubate 20 minutes.

Wash, then add 100 µl of fluorescent probe per well.

Incubate 20 minutes.

Wash, then add 50 µl of reagent grade water to each well.

Read the fluorescence on a microplate reader at an excitation wavelength of 488 nm emission wavelength of 576 nm to obtain data for C5 RPE. Then, read the fluorescence at an excitation wavelength of 620 nm emission wavelength of 661 nm to obtain data for C6 APC.

Figure 76

Assay Summary
Add 50 μl of standard/sample per well.
Incubate 2 hours.
Wash, then add 50 μl of biotinylated antibody per well.
Incubate 1 hour.
Wash, then add 50 μl of SP per well.
Incubate 30 minutes.
Wash, then add 50 μl of Chromogen Substrate per well.
Incubate 10 minutes.
Add 50 μl of Stop Solution per well.
Read at 450 nm immediately.
Figure 77

Assay Summary
Add 100 μl of standard/sample per well.
Incubate 20 minutes.
Wash, then add 100 μl of fluorescent probe per well.
Incubate 20 minutes.
Wash, then add 50 μl of reagent grade water to each well.
Read at an excitation wavelength of 488 nm and an emission wavelength of 530 nm.
Figure 78

Assay Summary
Add 100 µl of standard/sample per well.
Incubate 20 minutes.
Wash, then add 100 µl of fluorescent probe per well.
Incubate 20 minutes.
Wash, then add 50 µl of reagent grade water to each well.
Read at an excitation wavelength of 594 nm and an emission wavelength of 624 nm.
Figure 79

Assay Summary
Add 100 µl of standard/sample per well.
Incubate 20 minutes.
Wash, then add 100 µl of fluorescent probe per well.
Incubate 20 minutes.
Wash, then add 50 µl of reagent grade water to each well.
Read at an excitation wavelength of 620 nm and an emission wavelength of 661 nm.
Figure 80

Assay Summary
Add 100 µl of standard/sample per well.
Incubate 20 minutes.
Wash, then add 100 µl of fluorescent probe per well.
Incubate 20 minutes.
Wash, then add 50 µl of reagent grade water to each well.
Read at an excitation wavelength of 488 nm and an emission wavelength of 576 nm.
Figure 81

Assay Summary

Add 100 µl of standard/sample per well.

Incubate 20 minutes.

Wash, then add 100 µl of fluorescent probe per well.

Incubate 20 minutes.

Wash, then add 50 µl of reagent grade water to each well.

Read the fluorescence on a microplate reader at an excitation wavelength of 488 nm and an emission wavelength of 530 nm to obtain data for C5. Then, read the fluorescence at an excitation wavelength of 594 nm and an emission wavelength of 624 nm to obtain data for C6.

Figure 82

Assay Summary

Add 100 μl of standard/sample per well.

Incubate 20 minutes.

Wash, then add 100 μl of fluorescent probe per well.

Incubate 20 minutes.

Wash, then add 50 μl of reagent grade water to each well.

Read the fluorescence on a microplate reader at an excitation wavelength of 488 nm and an emission wavelength of 530 nm to obtain data for C6. Then, read the fluorescence at an excitation wavelength of 594 nm and an emission wavelength of 624 nm to obtain data for C5.

Figure 83

Assay Summary

Add 100 µl of standard/sample per well.

Incubate 20 minutes.

Wash, then add 100 µl of fluorescent probe per well.

Incubate 20 minutes.

Wash, then add 50 µl of reagent grade water to each well.

Read the fluorescence on a microplate reader at an excitation wavelength of 488 nm emission wavelength of 576 nm to obtain data for C6 RPE. Then, read the fluorescence at an excitation wavelength of 620 nm emission wavelength of 661 nm to obtain data for C5 APC.

Figure 84

Assay Summary

Add 100 µl of standard/sample per well.

Incubate 20 minutes.

Wash, then add 100 µl of fluorescent probe per well.

Incubate 20 minutes.

Wash, then add 50 µl of reagent grade water to each well.

Read the fluorescence on a microplate reader at an excitation wavelength of 488 nm emission wavelength of 576 nm to obtain data for C5 RPE. Then, read the fluorescence at an excitation wavelength of 620 nm emission wavelength of 661 nm to obtain data for C6 APC.

Figure 85

IMMUNOASSAYS USING OVER-LABELED FLUORESCENT PROBES

CROSS-REFERENCE TO RELATED APPLICATIONS

This application claims the benefit of U.S. Provisional Patent Application No. 61/881,255 filed Sep. 23, 2013, U.S. Provisional Patent Application No. 61/889,762 filed Oct. 11, 2013 and U.S. Provisional Patent Application No. 62/029,159 filed Jul. 25, 2014 the entire disclosures of which are incorporated herein by reference.

FIELD OF THE INVENTION

The disclosure relates to immunoassay methods and kits for detecting and quantifying the amount of one or more analytes of interest in a sample.

SUMMARY OF THE INVENTION

In one aspect, the present disclosure provides an immunoassay for detecting or measuring the amount of at least one analyte of interest in a sample, the immunoassay comprising: obtaining a first capture antibody specific for a first analyte, the first capture antibody immobilized on a solid support; contacting the solid support with a blocking solution; contacting the solid support with the sample to form a first mixture comprising at least a complex of the first capture antibody with the first analyte; washing the first mixture to remove any analyte not complexed with a capture antibody to form a second mixture; contacting the second mixture with a first over-labeled fluorescent probe specific for the first analyte to form a third mixture comprising a complex of the first over-labeled fluorescent probe with the first analyte; washing the third mixture to remove any over-labeled fluorescent probe not complexed with an analyte to form a fourth mixture; and detecting a signal from the first over-labeled fluorescent probe, wherein the presence of signal is indicative of the presence of the amount of the first analyte present in the sample. The immunoassay can further comprise obtaining at least a second capture antibody specific for a second analyte, the second capture antibody also immobilized on the solid support; contacting the solid support with the sample to form a first mixture comprising a complex of the first capture antibody with the first analyte and a complex of the second capture antibody with the second analyte; washing the first mixture to remove any analyte not complexed with a capture antibody to form a second mixture; contacting the second mixture with the first over-labeled fluorescent probe and a second over-labeled fluorescent probe specific for a second antibody to form a third mixture comprising a complex of the first over-labeled fluorescent probe with the first analyte and a complex of the second over-labeled fluorescent probe with the second analyte; washing the third mixture to remove any over-labeled fluorescent probe not complexed with an analyte to form a fourth mixture; and detecting a signal from each of the first and second over-labeled fluorescent probes, wherein the presence of signal is indicative of the presence of the amount of the first and second analytes present in the sample. The first and second capture antibodies can be randomly immobilized on the solid support. Optionally, the immunoassay can further comprise obtaining n additional capture antibodies each specific for a different analyte, and all capture antibodies including the first and second and any n capture antibodies can be randomly immobilized on the solid support. The immunoassay may be conducted for a period from about 30 minutes to about 120 minutes.

In another aspect, the present disclosure provides an immunoassay for detecting or measuring the amount of at least one analyte of interest in a sample, the immunoassay comprising: obtaining a first capture antibody specific for a first analyte immobilized on a solid support; contacting the solid support with a blocking solution; contacting the solid support with the sample to form a first mixture comprising a complex of the first capture antibody with the first analyte; contacting the first mixture a first over-labeled fluorescent probe specific for the first capture antibody to form a second mixture comprising a complex of the first capture antibody with the first over-labeled fluorescent probe, wherein the first over-labeled fluorescent probe competes with the first analyte; washing the second mixture to remove any analyte or over-labeled fluorescent probe not complexed with a capture antibody to form a third mixture; and detecting a signal from the first over-labeled fluorescent probe, wherein the signal is inversely proportional to the amount of analyte present in the sample. The immunoassay can further comprise: obtaining at least a second capture antibody specific for a second analyte, the first and second capture antibodies immobilized on the solid support; contacting the solid support with the sample to form a first mixture comprising a complex of the first capture antibody with the first analyte and a complex of the second capture antibody with the second analyte; washing the first mixture to remove any analyte not complexed with a capture antibody to form a second mixture; contacting the second mixture with the first over-labeled fluorescent probe and a second over-labeled fluorescent probe specific for a second antibody to form a third mixture comprising a complex of the first over-labeled fluorescent probe with the first analyte and a complex of the second over-labeled fluorescent probe with the second analyte; washing the third mixture to remove any over-labeled fluorescent probe not complexed with an analyte to form a fourth mixture; and detecting a signal from each of the first and second over-labeled fluorescent probes, wherein the signal from each of the first and second over-labeled fluorescent probes is inversely proportional to the amount of each of the first and second analytes present in the sample. The immunoassay can further comprise obtaining n additional capture antibodies, each n additional capture antibody specific for a different analyte, the first and second and n capture antibodies randomly immobilized on the solid support. The immunoassay may be conducted for a period from about 20 minutes to about 40 minutes.

In another aspect, the present disclosure provides an immunoassay kit for conducting an immunoassay to detect at least one analyte in a sample, the kit comprising: a solid support; at least a first capture antibody specific for a first analyte; and at least a first over-labeled fluorescent probe capable of providing a detectable signal. The immunoassay can further comprise at least a second capture antibody specific for a second analyte and a second over-labeled fluorescent probe. The immunoassay kit can further comprising at least n additional capture antibodies, each n additional capture antibody specific for a different analyte, and n additional over-labeled fluorescent probes. In the immunoassay kit, for example, the first over-labeled fluorescent probe is specific for the first analyte, the second over-labeled fluorescent probe is specific for the second analyte, and any n additional over-labeled fluorescent probes are each specific for an $n^{th}$ additional analyte. Additionally, the first over-labeled fluorescent probe can be specific for the first capture antibody, the second over-labeled fluorescent probe specific for the second capture antibody, and any n additional over-labeled fluorescent probes each specific for an $n^{th}$ capture antibody. In the immunoassay kit, the first, second and any n additional capture antibodies can be randomly immobilized on the solid support.

In any of the immunoassays and immunoassay kits described herein, the sample can be plasma, serum, whole blood, urine, tissue extract, cell culture samples or any other body fluid.

In any of the immunoassays and immunoassay kits described herein, the solid support can be selected a magnetic particle, bead, test tube, microtiter plate, cuvette, membrane, a scaffolding molecule, film, filter paper, disc, and chip.

In any of the immunoassays and immunoassay kits described herein, the first, second and any additional over-labeled fluorescent probes each comprise at least two conjugation moieties and at least two fluorescent moieties, wherein the conjugation moieties are labeled with the fluorescent moieties and are conjugated to the over labeled fluorescent probes. The fluorescent moieties can be selected for example from Li-COR, CF fluorescent dyes, DyLight Dyes, Alexa Fluor, CY dyes, ATTO, Chromis dyes, R-phycocyanins, allophycocyanin, green fluorescent protein, fluorescent cDNA, and any combination of any of the foregoing. The fluorescent moieties can be selected for example from DyLight 350, DyLight 405, DyLight 488, DyLight 594, DyLight 633, DyLight 650, ATTO 390, ATTO 565, ATTO 590, ATTO 430LS, ATTO 490LS, and any combination of any of the foregoing.

In any of the immunoassays and immunoassay kits described herein, the conjugation moieties can be selected from BSA, Ovalbumin (OVA), Keyhole limpet hemocyanin (KLH), KCKCKCKCKCKCKCK (SEQ ID NO: 1), and any combination of any of the foregoing. The conjugation moieties can, for example, be the same for each over-labeled fluorescent probe.

In the immunoassays and immunoassay kits described herein, each over-labeled fluorescent probe is specific for one analyte and has a different fluorescent signal from any other over-labeled fluorescent probes being used in the immunoassay and which is specific for other analytes in the sample.

In the immunoassays and immunoassay kits described herein, an immunoassay can have less than about 10%, or less than about 5% cross-reactivity with any one or more cross-reacting analytes present in the sample. Additionally, for any of the immunoassays and immunoassay kits described herein, at least one signal from the one or more over-labeled fluorescent probes may be detected using a fluorescent intensity reader.

In any of the immunoassays and immunoassay kits described herein, one or more analytes of interest can be selected from: Human alpha1-acid Glycoprotein, Human alpha Fetoprotein, Human alpha1-Microglobulin. Human alpha2-HS-Glycoprotein, Human Adiponectin, Mouse Adiponectin, Rat Adiponectin, Mouse Albumin, Rabbit Albumin, Swine Albumin, Human Pancreatic Amylase, Rat ANP, Human alpha1-antitripsin, Human Apolipoprotein AI, Human Apolipoprotein AII, Human Apolipoprotein B, Human Apolipoprotein CI, Human Apolipoprotein CII, Human Apolipoprotein CIII, Human Apolipoprotein E, Human Apolipoprotein H, Human Antithrombin III, Mouse Antithrombin II, Rat BNP-32, Rat BNP-45, Human Complement C1q, Human Complement C1r, Human Complement C1, Human Complement C2, Human Complement C3, Human Complement C4, Human Complement C5, Human Complement C6, Human Complement C7, Human Complement C8, Human Complement C9, Human Ceruloplasmin, Rat Ceruloplasmin, Human C-Reactive Protein, Rat C-Reactive Protein, Canine C-Reactive Protein, Mouse C-Reactive Protein, Human Elastase (ELA-2), Human Complement Factor B, Human Complement Factor D, Mouse Complement Factor D, Human Complement Factor H, Human Complement Factor I, Human Ferritin, Canine Fibrinogen, Human Fibrinogen, Mouse Fibrinogen, Rat Fibrinogen, Human Fibronectin, Mouse Fibronectin, Human Factor IX, Human Factor V, Human Factor VII, Human Factor X, Human Factor XI, Human Factor XII, Human Factor XIII, Human GC-Globulin, Human GPIIb/IIIa, Bovine Haptoglobulin, Canine Haptoglobulin, Human Haptoglobulin, Swine Haptoglobulin, Rat Haptoglobulin, Human Hemopexin, Human IgA, Human IgD, Human IgG3, Human IgG, Human IgM, Human Kininogen (HMW), Human Lactoferrin, Human Lp(a), Human Lysozyme, Human alpha 2 Macroglobulin, Mouse alpha Macroglobulin, Rat alpha Macroglobulin, Human beta 2-Microglobulin, Rat beta 2-Microglobulin, Human PAI-1, Human PAI-1/tPA, Human Prekallikrein (PK), Bovine Plasminogen, Human Plasminogen, Mouse Plasminogen, Rat Plasminogen, Human Prealbumin, Human Protein C, Human Protein S, Human Protein Z, Human Prothrombin, Swine Prothrombin, Mouse Prothrombin, Human RBP4, Human RBP, Mouse RBP4, Rat RBP4, Canine RBP4, Human Serum Amyloid P, Human TAT Complex, Mouse TAT Complex, Human TF, Human TFPI, Human Thrombin, Human tPA, Human Transferrin, Rat Transferrin, Mouse Transferrin, Human uPA, Human vWF, Human Alpha 1 Antichymotrypsin, Human PSA, Human Total, PSA, Human IgE, Human ApoJ, Human C1qBP, Human Cancer Antigens, Human Cystatin C and combinations thereof.

In any of the immunoassays and immunoassay kits described herein, one or more analytes of interest can be an auto-antibody, an antiviral antibody or an anti-bacterial antibody. For example, at least one analyte can be an auto-antibody, antiviral antibody or antibacterial antibody selected from: Anti Deamidated Gliadin Peptide (DGP), Anti dsDNA, Anti Histone, Anti Jo-1, Anti-*Borrelia burgdorferi*, Anti-Adenovirus, Anti-ANA, anti-Annexin V, Anti-*Ascaris lumbricoides*, Anti-*Bordetella pertussis*, Anti-*Bordetella pertussis* toxin, Anti-*Borrelia burgdorferi*, Anti-*Brucella*, Anti-*Candida albicans*, Anti-Cardiolipin, Anti-Centromere B, Anti-Chagas, Anti-Chikungunya Virus, Anti-*Chlamydia pneumoniae*, Anti-*Chlamydia trachomatis*, Anti-*Clostridium tetani* toxin, Anti-*Corynebacterium diphtheriae* toxin, Anti-*Coxiella burnetii* (Q-Fever) Phase 2, Anti-Cytomegalovirus (CMV), Anti-Dengue virus IgG, Anti-*Echinococcus* IgG, Anti-ENA, Anti-*Entamoeba histolytica*, Anti-Epstein Barr virus (EBV-EBNA), Anti-*Helicobacter pylori*, Anti-Herpes simplex virus Type 1, Anti-HSP60, anti-HSP70, Anti-Influenza virus A, Anti-Influenza virus B, Anti-*Leishmania* Dog, Anti-Malaria, Anti-Measles virus, Anti-MPO (p-ANCA), Anti-Mumps virus, Anti-*Mycoplasma pneumoniae*, Anti-Parainfluenza virus 1,2,3, Anti-Parvovirus B 19, Anti-PR 3 (c-ANCA, Anti-Respiratory syncytial virus (RSV, Anti-Rheumatoid Factor IgM, Anti-RNP/Sm, Anti-RNP70, Anti-Rubella virus, Anti-*Schistosoma mansoni*, Anti-scl70, Anti-Sm, Anti-SS-A, Anti-SS-B, Anti-*Taenia solium*, Anti-Thyroglobulin, Anti-Thyroid Peroxidase, Anti-Tick-borne encephalitis, Anti-*Toxocara canis*, Anti-*Toxoplasma gondii*, Anti-*Treponema pallidum*, Anti-*Trichinella spiralis*, Anti-Varicella-Zoster virus, and Anti-Prothrombin.

Reference to Color Figures

The application file contains at least one photograph executed in color. Copies of this patent application publication with color photographs will be provided by the Office upon request and payment of the necessary fee.

BRIEF DESCRIPTION OF THE FIGURES

FIG. 58 depicts a diagram summarizing an ELISA protocol performed using human albumin in Example 6.

FIG. 59 depicts a diagram summarizing an APC fluorescent protocol performed using human albumin in Example 6.

FIG. 60 depicts a diagram summarizing an RPE fluorescent protocol performed using human albumin in Example 6.

FIG. 61 depicts a diagram summarizing an APC multiplex protocol performed using human albumin in Example 6.

FIG. 62 depicts a diagram summarizing an RPE multiplex protocol performed using human albumin in Example 6.

FIG. 63 depicts a diagram summarizing an ELISA protocol performed using rat albumin in Example 6.

FIG. 64 depicts a diagram summarizing an APC fluorescent protocol performed using rat albumin in Example 6.

FIG. 65 depicts a diagram summarizing an RPE fluorescent protocol performed using rat albumin in Example 6.

FIG. 66 depicts a diagram summarizing an APC multiplex protocol performed using rat albumin in Example 6.

FIG. 67 depicts a diagram summarizing an RPE multiplex protocol performed using rat albumin in Example 6.

FIG. 68 depicts a diagram summarizing an ELISA protocol performed using human Complement C5 in Example 8.

FIG. 69 depicts a diagram summarizing DyLight 488 fluorescent protocol performed using human Complement C5 in Example 8.

FIG. 70 depicts a diagram summarizing ATTO 590 fluorescent protocol performed using human Complement C5 in Example 8.

FIG. 71 depicts a diagram summarizing an APC fluorescent protocol performed using human Complement C5 in Example 8.

FIG. 72 depicts a diagram summarizing an RPE fluorescent protocol performed using human Complement C5 in Example 8.

FIG. 73 depicts a diagram summarizing DyLight 488 multiplex protocol performed using human Complement C5 in Example 8.

FIG. 74 depicts a diagram summarizing ATTO 590 multiplex protocol performed using human Complement C5 in Example 8.

FIG. 75 depicts a diagram summarizing APC multiplex protocol performed using human Complement C5 in Example 8.

FIG. 76 depicts a diagram summarizing RPE multiplex protocol performed using human Complement C5 in Example 8.

FIG. 77 depicts a diagram summarizing an ELISA protocol performed using human Complement C6 in Example 8.

FIG. 78 depicts a diagram summarizing DyLight 488 fluorescent protocol performed using human Complement C6 in Example 8.

FIG. 79 depicts a diagram summarizing ATTO 590 fluorescent protocol performed using human Complement C6 in Example 8.

FIG. 80 depicts a diagram summarizing an APC fluorescent protocol performed using human Complement C6 in Example 8.

FIG. 81 depicts a diagram summarizing an RPE fluorescent protocol performed using human Complement C6 in Example 8.

FIG. 82 depicts a diagram summarizing ATTO 590 multiplex protocol performed using human Complement C6 in Example 8.

FIG. 83 depicts a diagram summarizing DyLight 488 multiplex protocol performed using human Complement C6 in Example 8.

FIG. 84 depicts a diagram summarizing RPE multiplex protocol performed using human Complement C6 in Example 8.

FIG. 85 depicts a diagram summarizing APC multiplex protocol performed using human Complement C6 in Example 8.

DETAILED DESCRIPTION OF THE DISCLOSURE

Figure 1:
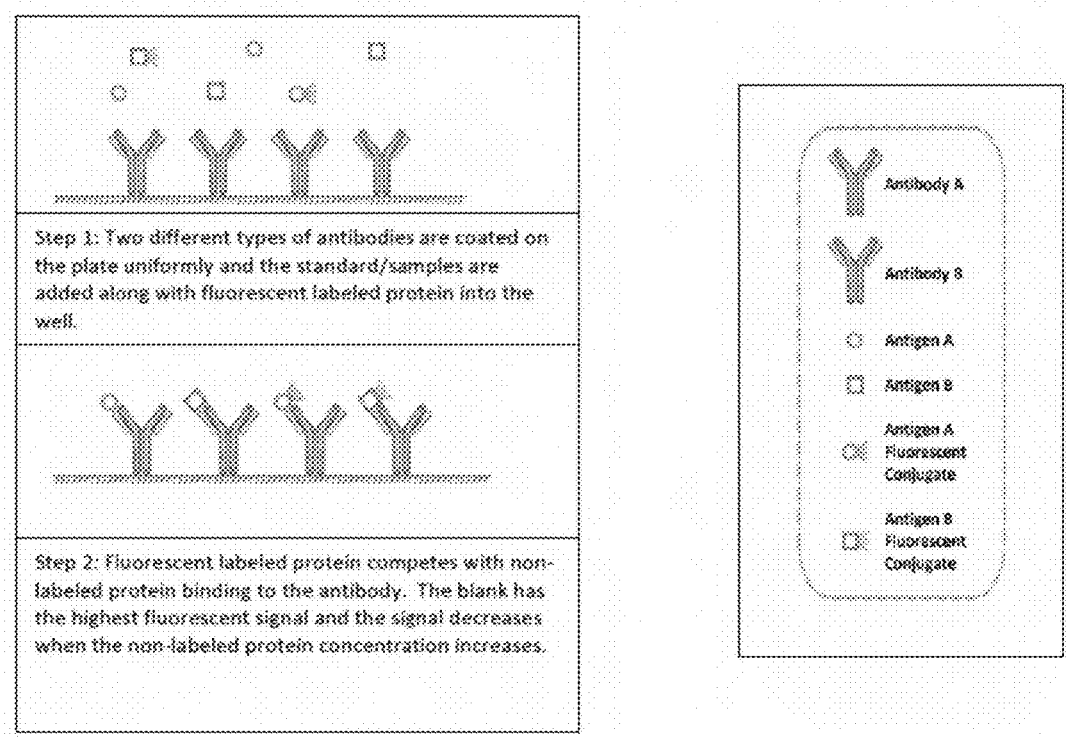
FIG. 1 is a schematic illustration of multiplexing in an endpoint fluorescent competitive immunoassay.

Various methods for labeling biomolecules are known, including the use of fluorescent labels. Recognized advantages of fluorescent labels include their high sensitivity at low concentrations such that a minimal amount of label, e.g. no more than one fluorescent moiety per molecule, can be used so that the label does not negatively impact the structural integrity, folding and specific binding function of the biomolecule. Heavy labeling of biomolecules with more than one fluorescent moiety per biomolecule is not used and has generally not been pursued because of expected negative impact of the additional fluorescent moieties on form and function of the biomolecule. Additionally, fluorescent signal processing has been limited by reliance on flow cytometry or fluorescent image scanners, i.e., image analysis, which are insufficiently sensitive to fluorescent intensity to use it as a measure of fluorescent signal strength.

In contrast, the present disclosure provides a new approach to fluorescent immunoassays utilizing a type of electromagnetic spectroscopy to analyze fluorescence from a sample, and over-labeled fluorescent probes as detailed further herein. Known immunoassays using flow cytometry or fluorescent image scanners, i.e., image analysis, which have sensitivity that is insufficient to use fluorescent intensity as a measure of signal strength. In contrast, the present disclosure provides immunoassays which can use and measure fluorescent intensity, and thus allows the use of certain types of fluorescent readers that provide fast and accurate analysis of sample. This is achieved in part through the use of novel over-labeled fluorescent probes, which for the first time amplify the fluorescent signal, and thus provide sufficient signal strength for fluorescent readers, and thus fluorescent intensity to be used as a measure of specific binding in the assay. Each over-labeled fluorescent probe includes a specific binding agent such as an antibody, and a fluorescent moiety. Pairs and combinations of different fluorescent probes, each with a different specific binding agent, also each include a fluorescent moiety which emits at a different wavelength. Moreover, pairs and combinations of different fluorescent probes are selected such that a low level of cross-reactivity exists among the two or more fluorescent probes, thus allowing improved detection and quantification of multiple target analytes in one multiplex immunoassay.

As used herein, the terms "specific binding" or "specifically binding" characterize an agent which is a protein (such as but not limited to an antibody) or peptide, and refers to the coupling of the protein or peptide with another, second molecule, wherein the coupling is conditioned on the recognition by the protein or peptide of a distinguishing structure of the second molecule. An example of such a structure is an epitope on an antigen. An antibody which specifically binds an antigen recognizes an epitope on the antigen. It should, however, be understood that other proteins and peptides may demonstrate comparable binding capabilities with respect to a second molecule.

As used herein, the term "antibody" encompasses an immunoglobulin molecule or an immunologically active portion thereof, i.e., an antigen-binding portion thereof. Immunologically active portions of immunoglobulin molecules include, for example, F(ab) and F(ab') and F(ab') 2 fragments. Any antibody can be a polyclonal antibody, monoclonal antibody, human antibody, humanized antibody, chimeric antibody, or recombinant antibody. An antibody can be single-chain Fvs ("scFv"), an affinity maturated antibody, a single domain antibody, or a functionally active epitope-binding fragment of any of the foregoing.

As used herein, the term "subject" refers to an animal, including but not limited to a mammal including a human and a non-human primate (for example, a monkey or great ape), a cow, a pig, a cat, a dog, a rat, a mouse, a horse, a goat, a rabbit, a sheep, a hamster, a guinea pig). Preferably, the subject is a human.

As used herein, the term "sample" refers to an amount of biological tissue derived from a subject's body, including but not limited to tissue extract, cell culture samples, serum, plasma, whole blood, lymph, CNS fluid, urine or other bodily fluids of a subject that is being tested for, and/or may be suspected of containing one or more target analyte(s), i.e., analyte(s) of interest. The sample can be prepared using routine techniques known to those skilled in the art.

Unless otherwise defined herein, scientific and technical terms used in connection with the present disclosure shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms as used herein and in the claims shall include pluralities and plural terms shall include the singular.

The use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Generally, nomenclatures used in connection with, and techniques of, cell and tissue culture, molecular biology, immunology, microbiology, genetics and protein and nucleic acid chemistry and hybridization described herein are well known and commonly used in the art. The methods and techniques of the present disclosure are generally performed according to conventional methods well known in the art and as described in various general and more specific references that are cited and discussed throughout the present specification unless otherwise indicated. Any chemical, enzymatic or staining reactions, or purification techniques are performed according to manufacturer's specifications and protocols, as commonly accomplished in the art or as described herein.

The nomenclatures used in connection with, and the laboratory procedures and techniques of, analytical chemistry, synthetic organic chemistry, and medicinal and pharmaceutical chemistry including radiopharmaceutical chemistry described herein are also well known and commonly used in the art. Standard techniques are used for chemical syntheses, chemical analyses, pharmaceutical preparation, formulation, delivery, diagnosis and treatment of all subjects, human and animal.

A. Immunoassays and Immunoassay Kits

As provided herein, immunoassays for detecting at least one or more analytes of interest in a sample use at least one, or more, over-labeled fluorescent probes. An over-labeled fluorescent probe comprises a specific binding agent such as an antibody capable of specifically binding a target antigen, at least one conjugation moiety, and at least two or more fluorescent moieties. Alternatively, an over-labeled fluorescent probe may comprise the specific binding agent, at least two conjugation moieties, and at least two or more fluorescent moieties. The fluorescent moiety may be dye or a peptide or fluorescent protein as detailed further herein below. An over-labeled fluorescent probe can comprise 2 to as many as 150, or even more, fluorescent moieties. Surprisingly, the inventor has found that such high levels of labeling, as described herein, do not interfere with the specific binding capabilities of the specific binding agent. For example, depending on the conjugation approach used, an over-labeled fluorescent probe can comprise 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 120, 130, 140, 150, or 160 fluorescent moieties. It should be understood that depending on the conjugation approach used, any over-labeled fluorescent probe described herein can comprise any whole number of fluorescent moieties from 2 to about 160.

In one such over-labeled fluorescent probe, a specific binding agent such as an antibody itself provides the conjugation moiety in the form of free primary amines. Usually, for example, an antibody has about 20 free primary amine groups. The fluorescent moiety thus can be covalently bound directly to 2, 3, 4, 5, 6, 7, 8, 9, 10, 11, 12, 13, 14, 15, 16, 17, 18, 19 or 20 free primary amines on the antibody.

Alternatively, an over-labeled fluorescent probe can further comprise another peptide or protein as the conjugation moiety. Any peptide or protein capable of covalently binding to a free amine group on the specific binding agent and also to a fluorescent moiety can be used. In non-limiting example, a conjugation moiety can be selected from Bovine Serum Albumin (BSA), Ovalbumin (OVA), Keyhole limpet hemocyanin (KLH), a peptide having the amino acid sequence of SEQ. ID NO: 1 (KCKCKCKCKCKCKCK), and any combination of any of the foregoing.

When such a protein or peptide is the conjugation moiety, the conjugation moiety itself can be covalently bound to multiple fluorescent moieties. For example, Bovine Serum Albumin, which itself has up to or about 40 free primary amines, can be covalently bound to multiple, and as many as about 40 fluorescent moieties. Multiple such proteins or peptides, each bearing multiple fluorescent moieties, can be conjugated to the specific binding agent. Thus it can be appreciated that such proteins or peptides can be used to amplify the fluorescent signal generated by a given over-labeled fluorescent probe, by greatly increasing the number of fluorescent moieties that can be conjugated to the specific binding agent. For example, using the example of BSA as described above, BSA can be bound to as many as 40 fluorescent moieties. Such a labeled BSA molecule can then be bound to 2, 3, 4 or more free primary amines on the specific binding agent (e.g. antibody), and thus provide an over-labeled fluorescent probe having 80, 120, 160 or potentially even more fluorescent moieties.

As detailed further herein below, immunoassays may use two or more different over-labeled fluorescent probes to detect and quantify two, three, four, five, six or more different analytes in a sample in the same assay, i.e., to provide multiplexing capability. Each different fluorescent probe has a different specific binding agent selected to minimize cross-reactivity with the other over-labeled fluorescent probes being used, and a different fluorescent moiety selected for minimal cross-reactivity with the other fluorescent moieties being used, and minimal interference with the fluorescent signal generated by the other fluorescent probes being used. It should be understood that while the specific binding agent and fluorescent moieties for each over-labeled probe will be different from each of the other over-labeled fluorescent probes being used, the conjugation moiety used for each probe can be the same as or different from the conjugation moiety used in any of the other probes.

The fluorescent moiety can be any fluorescent compound including a dye or a peptide or fluorescent proteins, as known in the art, such as but not limited to Li-COR, CF fluorescent dyes, DyLight Dyes, Alexa Fluor, CY dyes, ATTO, Chromis dyes, R-phycocyanins, allophycocyanin, green fluorescent protein, fluorescent cDNA, and any combination of any of the foregoing. In some fluorescent probes, the fluorescent moiety is selected for example from DyLight 350, DyLight 405, DyLight 488, DyLight 594, DyLight 633, DyLight 650, ATTO 390, ATTO 565, ATTO 590, ATTO 430LS, ATTO 490LS, and any combination of any of the foregoing. As noted herein above, when multiple over-labeled fluorescent probes are being used for a multiplex immunoassay, the different fluorescent moiety for each probe is selected for minimal cross-reactivity with the other fluorescent moieties being used, and minimal interference with the fluorescent signal generated by the other fluorescent probe(s) being used. It will be understood that certain pairings and combinations of fluorescent moieties will provide enhanced ability to discriminate among the different fluorescent signals.

The immunoassays described herein can be better and further understood with reference to existing immunoassay methodology. Competitive immunoassays are based on the principles set forth in FIG. 1. For example, at least one capture antibody or two different capture antibodies are uniformly coated on a solid support such as a multiwell plate, and a standard and sample added along with fluorescent labeled protein into the wells. It will be understood that each antibody is a specific binding agent, capable of specifically binding a target analyte, which is a protein. The fluorescent labeled protein competes with non-labeled protein binding to the antibody. A blank sample has the highest fluorescent signal, and the fluorescent signal decreases when the non-labeled protein concentration increases.

Figure 2:
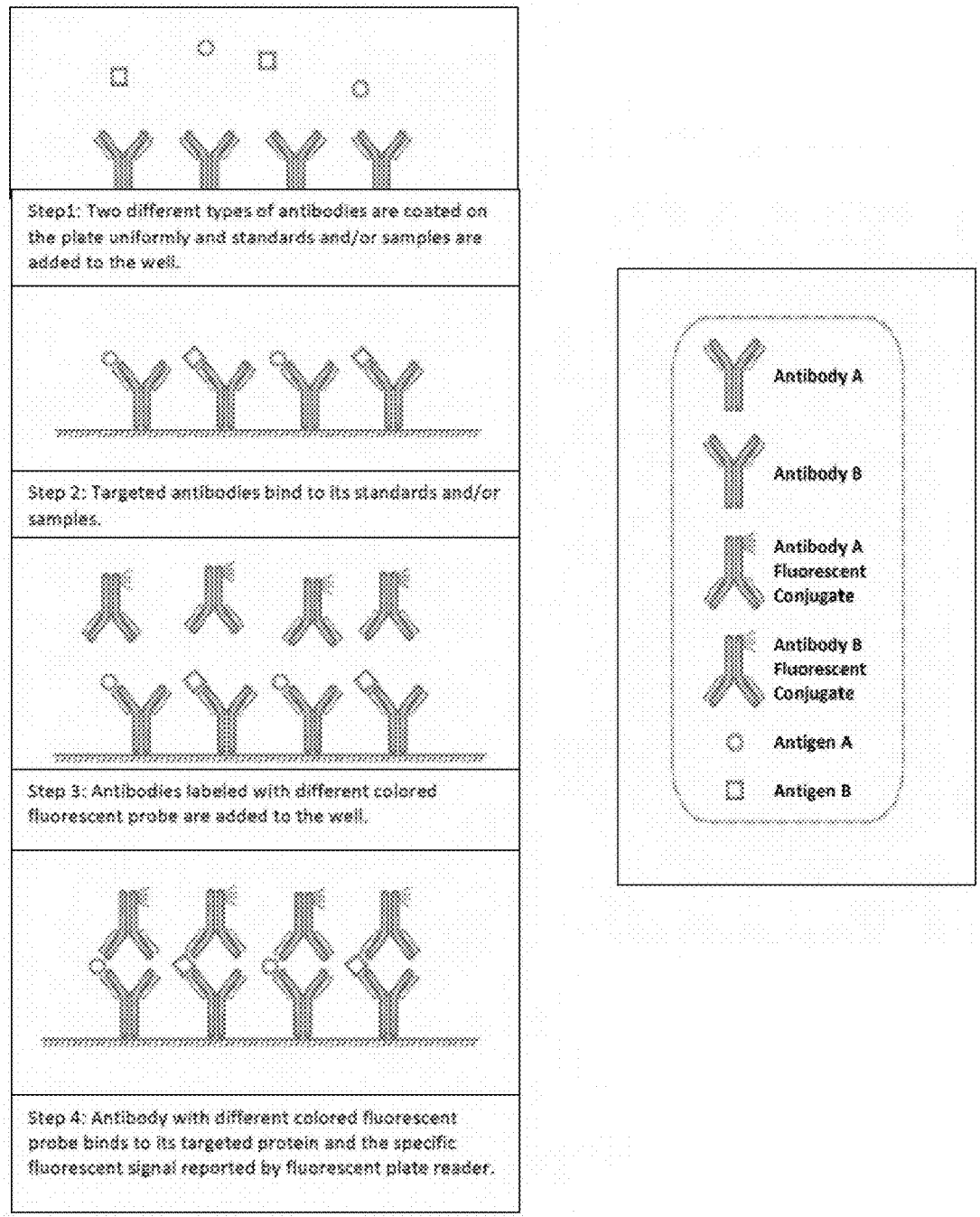
FIG. 2 is a schematic illustration of multiplexing in an endpoint fluorescent sandwich immunoassay.

Current sandwich immunoassays take a different approach, as shown in FIG. 2. A solid surface is coated with a known quantity of one or more capture antibodies. Non-specific binding sites on the surface are blocked, and the sample containing the target analyte is applied to the plate. Following a wash to remove unbound analyte, a second antibody specific for each target analyte is added, forming a "sandwich" consisting of each analyte between the two analyte-specific antibodies. Enzyme-linked secondary antibodies, i.e., detection antibodies which bind to the antibody's Fc region, are then introduced. For multiple target analytes, the detection antibodies are labeled with different labels, e.g. different fluorescent labels. Following a wash to remove the unbound antibody-enzyme conjugates, a reagent is added which is converted by the enzyme to a molecule providing a detectable signal such as a spectral, fluorescent or electrochemical signal. The signal from plate wells is then measured to determine the presence and quantity of antigen. For example, a specific fluorescent signal can be reported by a fluorescent plate reader.

Current competitive and sandwich immunoassay provide some limited multiplexing capability, only by spatially segregating each different capture antibody on the solid support(s). A problem faced by such multiplex immunoassays lies in the non-specific binding by the target analyte (protein) to other proteins, for example cytokines, that are commonly found in biological samples such as blood. Other proteins commonly found in blood plasma and other bodily fluids, which bind non-specifically to each other and can bind non-specifically to target analytes in a sample include PAI-1, PAI-1/tPA complex, and PAI-uPA complex.

Figure 3:
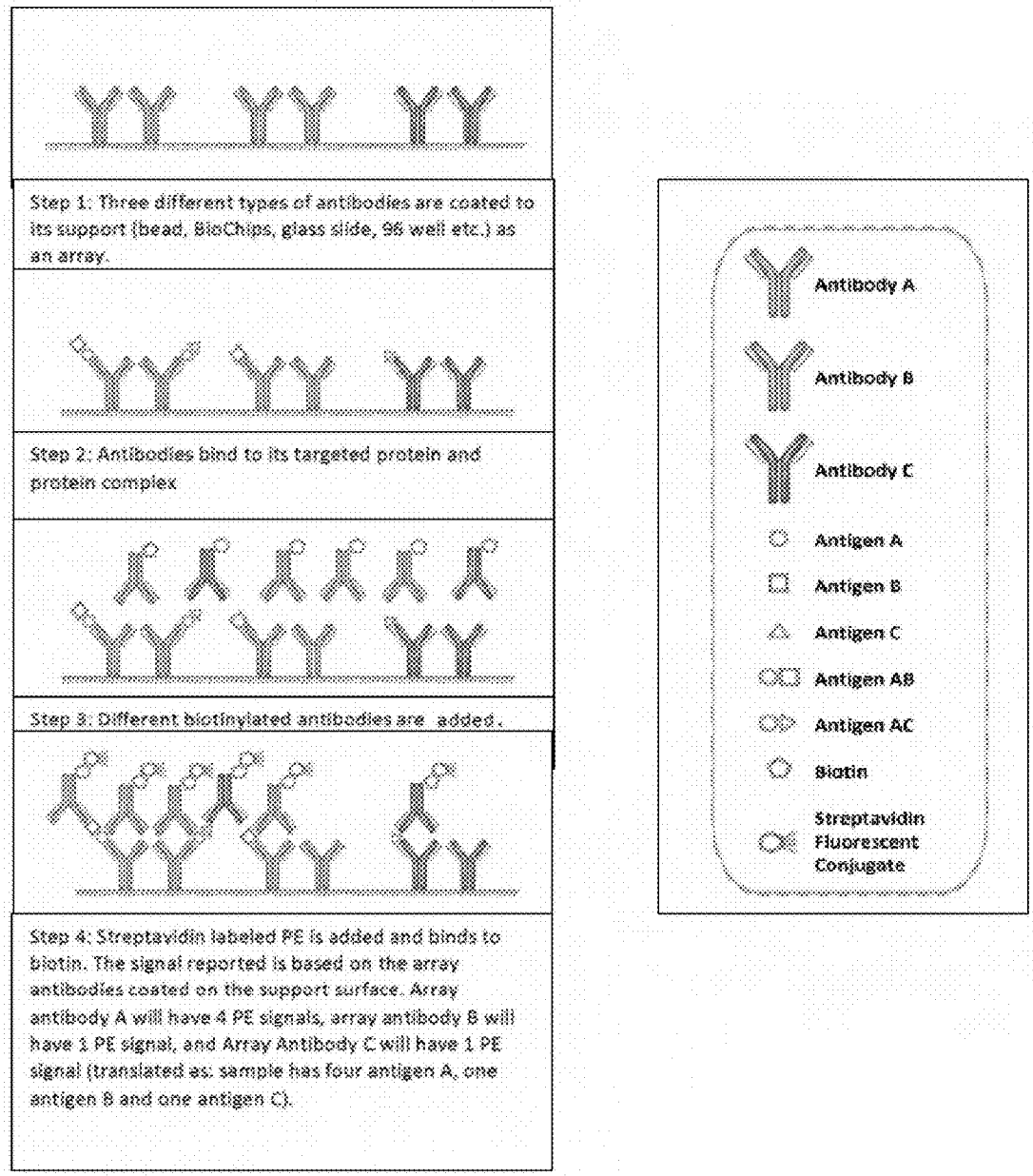
FIG. 3 is a schematic illustration of multiplexing in an immunoassay using a streptavidin fluorescent conjugate and biotinylated antibodies, which demonstrates the limitations of current immunoassay techniques in dealing with protein complexes.

The biotin-streptavidin approach has been used to amplify signal from an analyte, taking advantage of the strong, non-covalent bonds that form between streptavidin and multiple biotin molecules. FIG. 3 summarizes the biotin-streptavidin approach. Streptavidin is typically coated on a solid substrate. The antibody is both labeled with a fluorescent label and biotinylated, i.e., conjugated to biotin. Multiple biotinylated antibody molecules can bind to the streptavidin, thereby amplifying the fluorescent signal. Importantly, while this approach can provide good images using image scanners, it is not quantitative. Additionally, multiplexing capability is provided only by spatially segregating the different antibodies.

In contrast to current multiplex immunoassays, the immunoassays described herein do not require any spatial segregation of capture antibodies across an array or otherwise on a solid support, so that multiple capture antibodies can be randomly spatially distributed in an array or on a solid support. Put another way, multiple capture antibodies can be mixed. Additionally, using the over-labeled fluorescent probes described herein, the fluorescent reader is not an absorbance reader, flow cytometry system, chemiluminescence scanner or fluorescent image scanner but rather for the first time, a fluorescent intensity reader, i.e., universal plate reader such as the BioTek FLx800 or the Molecular Devices Gemini XPS reader. Moreover, the assay results are rapid, being obtainable in an hour or less, and can be provided in as little as about 20 minutes, rather than the 4-6 hours required with known immunoassays. The immunoassays described herein can also be adapted for use in a variety of automated and semi-automated systems as known in the art.

The disclosed ELISA assay and multiplex assays demonstrate similar performance in determining the amount of the target analyte in a sample, but differ in some ways. The singleplex and multiplex assay formats perform similarly in terms of determining the amount of the target analyte in a sample. For example, the intra coefficients of variability and inter coefficients of variability obtained using the ELISA format and the multiplex assay format are comparable. The coefficients of variability can be different for ELISA and multiplex formats however, because for the ELISA format it will be determined by the selected antibody pairs, while for the multiplex assay the coefficients of variability can vary by both the selected antibody pairs and the relative performance of the selected dyes. It should be understood that the multiplex assay format increases the complexity of the assays, but also provides a much greater dynamic assay range. Recent comparative testing of selected multiplex assay formats also provided greater reproducibility than the ELISA format tested (data not shown). In comparison, the ELISA format demonstrates greater sensitivity than the multiplex assay format, but with a reduced dynamic range for both the standard and samples. For example, the multiplex assay format can be very useful for measuring abundant protein such as blood proteins with less dilution and more accuracy.

Accordingly, in any of the immunoassays and immunoassay kits described herein, analytes of interest may be any molecule, the presence of which in a sample, and/or the amount of which is present in a sample, is indicative of a disease or condition or is otherwise of interest as an indicator of the biologic state of a subject, such as a human or animal subject. Diseases, conditions and biologic states of a subject that can be identified according to the immunoassays described herein include, but are not limited to: aging/mortality risk; anemia including hemolytic anemia and iron deficiency anemia; antithrombin deficiency; arthritis; ataxia telangiectasia; attention deficit hyperactivity disorder (ADHD); atransferrinemia; autoimmune disease including rheumatoid arthritis; cancer, including breast cancer, leukemia, lymphoma, lung cancer, ovarian cancer, pancreatic cancer, prostate cancer, and colorectal cancer; coronary disease; coronary heart disease risk; fetal developmental abnormalities including omphalocele, neural tube defects and yolk sac tumor; gall bladder infection; germ cell tumor; HDL deficiencies including Tangier disease; hyperlipoproteinemia including type IB; inflammation; liver disease; malnutrition; Menkes disease; metabolic diseases including diabetes (Type I and Type II); myocardial infarction; nephrotic syndrome; neurodegenerative diseases including Alzheimer's disease and Parkinson's disease; neuropathic amyloidosis; pancreatitis; proteinuria; sclerosis including amyotrophic lateral sclerosis (ALS) and multiple sclerosis; sepsis; sickle cell disease; systemic lupus erythematosus; vascular disease including atherosclerosis; and Wilson disease. Non-limiting examples of analytes of interest according to the present disclosure include: Human alpha1-acid Glycoprotein, Human alpha Fetoprotein, Human alpha1-Microglobulin, Human alpha2-HS-Glycoprotein, Human Adiponectin, Mouse Adiponectin, Rat Adiponectin, Mouse Albumin, Rabbit Albumin, Swine Albumin, Human Pancreatic Amylase, Rat ANP, Human alpha1-antitripsin, Human Apolipoprotein AI, Human Apolipoprotein AII, Human Apolipoprotein B, Human Apolipoprotein CI, Human Apolipoprotein CII, Human Apolipoprotein CIII, Human Apolipoprotein E, Human Apolipoprotein H, Human Antithrombin III, Mouse Antithrombin II, Rat BNP-32, Rat BNP-45, Human Complement C1q, Human Complement C1r, Human Complement C1, Human Complement C2, Human Complement C3, Human Complement C4, Human Complement C5, Human Complement C6, Human Complement C7, Human Complement C8, Human Complement C9, Human Ceruloplasmin, Rat Ceruloplasmin, Human C-Reactive Protein, Rat C-Reactive Protein, Canine C-Reactive Protein, Mouse C-Reactive Protein, Human Elastase (ELA-2), Human Complement Factor B, Human Complement Factor D, Mouse Complement Factor D, Human Complement Factor H, Human Complement Factor I, Human Ferritin, Canine Fibrinogen, Human Fibrinogen, Mouse Fibrinogen, Rat Fibrinogen, Human Fibronectin, Mouse Fibronectin, Human Factor IX, Human Factor V, Human Factor VII, Human Factor X, Human Factor XI, Human Factor XII, Human Factor XIII, Human GC-Globulin, Human GPIIb/IIIa, Bovine Haptoglobulin, Canine Haptoglobulin, Human Haptoglobulin, Swine Haptoglobulin, Rat Haptoglobulin, Human Hemopexin, Human IgA, Human IgD, Human IgG3, Human IgG, Human IgM, Human Kininogen (HMW), Human Lactoferrin, Human Lp(a), Human Lysozyme, Human alpha 2 Macroglobulin, Mouse alpha Macroglobulin, Rat alpha Macroglobulin, Human beta 2-Microglobulin, Rat beta 2-Microglobulin, Human PAI-1, Human PAI-1/tPA, Human Prekallikrein (PK), Bovine Plasminogen, Human Plasminogen, Mouse Plasminogen, Rat Plasminogen, Human Prealbumin, Human Protein C, Human Protein S, Human Protein Z, Human Prothrombin, Swine Prothrombin, Mouse Prothrombin, Human RBP4, Human RBP, Mouse RBP4, Rat RBP4, Canine RBP4, Human Serum Amyloid P, Human TAT Complex, Mouse TAT Complex, Human TF, Human TFPI, Human Thrombin, Human tPA, Human Transferrin, Rat Transferrin, Mouse Transferrin, Human uPA, Human vWF, Human Alpha 1 Antichymotrypsin, Human PSA, Human Total PSA, Human IgE, Human ApoJ, Human C1qBP, Human Cancer Antigens, Human Cystatin C and combinations thereof. It should be understood that the immunoassays described herein can be equally well applied to the detection and measurement of any other biomarker(s) indicating a disease, condition or biologic state of a subject. It should be further be understood that the multiplexing capability of the immunoassays described herein can be usefully applied to the detection and measurement of combinations of biomarker(s) which in combination indicate a disease, condition or biologic state of a subject.

An immunoassay using at least one over-labeled fluorescent probe as described herein can be used for detecting or measuring the amount of at least one analyte of interest in a sample. An immunoassay can comprise, for example, obtaining a first capture antibody specific for a first analyte, the first capture antibody immobilized on a solid support; contacting the solid support with a blocking solution; contacting the solid support with the sample to form a first mixture comprising at least a complex of the first capture antibody with the first analyte; washing the first mixture to remove any analyte not complexed with a capture antibody to form a second mixture; contacting the second mixture with a first over-labeled fluorescent probe specific for the first analyte to form a third mixture comprising a complex of the first over-labeled fluorescent probe with the first analyte; washing the third mixture to remove any over-labeled fluorescent probe not complexed with an analyte to form a fourth mixture; and detecting a signal from the first over-labeled fluorescent probe, wherein the presence of signal is indicative of the presence of the amount of the first analyte present in the sample. The immunoassay can further comprise obtaining at least a second capture antibody specific for a second analyte, the second capture antibody also immobilized on the solid support; contacting the solid support with the sample to form a first mixture comprising a complex of the first capture antibody with the first analyte and a complex of the second capture antibody with the second analyte; washing the first mixture to remove any analyte not complexed with a capture antibody to form a second mixture; contacting the second mixture with the first over-labeled fluorescent probe and a second over-labeled fluorescent probe specific for a second antibody to form a third mixture comprising a complex of the first over-labeled fluorescent probe with the first analyte and a complex of the second over-labeled fluorescent probe with the second analyte; washing the third mixture to remove any over-labeled fluorescent probe not complexed with an analyte to form a fourth mixture; and detecting a signal from each of the first and second over-labeled fluorescent probes, wherein the presence of signal is indicative of the presence of the amount of the first and second analytes present in the sample. The first and second capture antibodies can be randomly immobilized on the solid support. The immunoassay may be conducted for a period from about 30 minutes to about 120 minutes.

Optionally, the immunoassay can further comprise obtaining n additional capture antibodies each specific for a different analyte, and all capture antibodies including the first and second and any n capture antibodies can be randomly immobilized on the solid support.

Alternatively, an immunoassay for detecting or measuring the amount of at least one analyte of interest in a sample can comprise: obtaining a first capture antibody specific for a first analyte immobilized on a solid support; contacting the solid support with a blocking solution; contacting the solid support with the sample to form a first mixture comprising a complex of the first capture antibody with the first analyte; contacting the first mixture a first over-labeled fluorescent probe specific for the first capture antibody to form a second mixture comprising a complex of the first capture antibody with the first over-labeled fluorescent probe, wherein the first over-labeled fluorescent probe competes with the first analyte; washing the second mixture to remove any analyte or over-labeled fluorescent probe not complexed with a capture antibody to form a third mixture; and detecting a signal from the first over-labeled fluorescent probe, wherein the signal is inversely proportional to the amount of analyte present in the sample. The immunoassay can further comprise: obtaining at least a second capture antibody specific for a second analyte, the first and second capture antibodies immobilized on the solid support; contacting the solid support with the sample to form a first mixture comprising a complex of the first capture antibody with the first analyte and a complex of the second capture antibody with the second analyte; washing the first mixture to remove any analyte not complexed with a capture antibody to form a second mixture; contacting the second mixture with the first over-labeled fluorescent probe and a second over-labeled fluorescent probe specific for a second antibody to form a third mixture comprising a complex of the first over-labeled fluorescent probe with the first analyte and a complex of the second over-labeled fluorescent probe with the second analyte; washing the third mixture to remove any over-labeled fluorescent probe not complexed with an analyte to form a fourth mixture; and detecting a signal from each of the first and second over-labeled fluorescent probes, wherein the signal from each of the first and second over-labeled fluorescent probes is inversely proportional to the amount of each of the first and second analytes present in the sample. The immunoassay can further comprise obtaining n additional capture antibodies, each n additional capture antibody specific for a different analyte, the first and second and n capture antibodies randomly immobilized on the solid support. The immunoassay may be conducted for a period from about 20 minutes to about 40 minutes.

In any of the immunoassays described herein, and as described in further detail in the examples provided below, the signal from each over-labeled fluorescent probe is a fluorescent intensity signal which is detectable with a universal plate reader such as the BioTek FLx800, BioTek Synergy H1 (BioTek U.S., Winooski, Vt.) or Molecular Devices Gemini XPS (Molecular Devices, LLC, Sunnyvale, Calif.).

The immunoassays and kits described herein can be adapted to measurement and/or detection of an autoantibody, i.e., the analyte of interest may be an autoantibody. Any autoantibody or set of antibodies, including but not limited to immunoglobulin (IgA, IgG, or IgM) autoantibodies, can be measured or detected in a multiplex assay as described herein. Additionally, a multiplex assay as described herein can be used to measure or detect an antibody that a subject may generate against a virus or bacterium, either simultaneously with measurement or detection of one or more autoantibodies, or with measurement or detection of one or more other analyte(s) of interest. The immunoassays and kits described herein can therefore be used to detect or monitor a disease or disease progression, wherein the disease is an autoimmune disease, a viral disease or a bacterial disease.

Currently, any effort to detect multiple antibody types that may be involved in a particular disease or set of diseases requires that a separate enzyme immunoassay be run for each target auto-antibody, anti-viral or antibacterial antibody, each of which can detect a single antibody type in a sample. Additionally, current immunoassay methods are limited in ability to accurately quantify each antibody type in the sample. In contrast, the multiplex immunoassays described herein can measure and/or detect multiple analytes, e.g. multiple auto-antibodies (and/or any other antibodies) in a single assay, and can accurately quantify the analytes as well. The multiplex assay described herein can also be used to measure and/or detect antibodies generated against a virus and/or a bacterium.

Human proteins that are known to generate an autoimmune response in humans include but are not limited to Beta 2-glycoprotein 1, Thrombin, Prothrombin, Myeloperoxidase, HSP60, HSP70, Annexin V, lactoferin, ribonucleoproteins including Ribonucleoprotein, histidine-tRNA ligase, snRNP core proteins, Type I topoisomerase, nucleoporin, sp100 nuclear antigen, actin, cyclic citrullinated protein, nicotinic acetylcholine receptor, muscle-specific kinase, voltage-gated calcium channel, voltage-gated potassium channels, thyroid peroxidase, TSH receptor, amphiphysin, N-methyl-D-aspartate receptor, glutamic acid decarboxylase, aquaporin-4 and proteins in neutrophil cytoplasm. Cell and tissue elements are also known to elicit autoantibody formation, including smooth muscle, mitochondria, centromeres, and signal recognition particles. In any of the immunoassays and immunoassay kits described herein, an analyte of interest can be an antibody generated against any of the foregoing, or an antibody against a virus or a bacterium.

For example, in any of the immunoassays and immunoassay kits described herein, an analyte of interest can be selected from: Anti Deamidated Gliadin Peptide (DGP), Anti dsDNA, Anti Histone, Anti Jo-1, Anti-*Borrelia burgdorferi*, Anti-Adenovirus, Anti-ANA, Anti-Annexin V, Anti-*Ascaris lumbricoides*, Anti-*Bordetella pertussis*, Anti-*Bordetella pertussis* toxin, Anti-*Borrelia burgdorferi*, Anti-*Brucella*, Anti-*Candida albicans*, Anti-Cardiolipin, Anti-Centromere B, Anti-Chagas, Anti-Chikungunya Virus, Anti-*Chlamydia pneumoniae*, Anti-*Chlamydia trachomatis*, Anti-*Clostridium tetani* toxin, Anti-*Corynebacterium diphtheriae* toxin, Anti-*Coxiella burnetii* (Q-Fever) Phase 2, Anti-Cytomegalovirus (CMV), Anti-Dengue virus IgG, Anti-*Echinococcus* IgG, Anti-ENA, Anti-*Entamoeba histolytica*, Anti-Epstein Barr virus (EBV-EBNA), Anti-*Helicobacter pylori*, Anti-Herpes simplex virus Type 1, Anti-HSP60, anti-HSP70, Anti-Influenza virus A, Anti-influenza virus B, Anti-*Leishmania* Dog, Anti-Malaria, Anti-Measles virus, Anti-MPO (p-ANCA), Anti-Mumps virus, Anti-*Mycoplasma pneumoniae*, Anti-Parainfluenza virus 1,2,3, Anti-Parvovirus B 19, Anti-PR 3 (c-ANCA, Anti-Respiratory syncytial virus (RSV, Anti-Rheumatoid Factor IgM, Anti-RNP/Sm, Anti-RNP70, Anti-Rubella virus, Anti-*Schistosoma mansoni*, Anti-scl70, Anti-Sm, Anti-SS-A, Anti-SS-B, Anti-*Taenia solium*, Anti-Thyroglobulin, Anti-Thyroid Peroxidase, Anti-Tick-borne encephalitis, Anti-*Toxocara canis*, Anti-*Toxoplasma gondii*, Anti-*Treponema pallidum*, Anti-*Trichinella spiralis*, Anti-Varicella-Zoster virus, Anti-Prothrombin.

The present disclosure also encompasses kits for detecting or quantifying at least one analyte in a sample. For example, a kit can comprise a solid support, at least a first capture antibody specific for a first analyte, and at least a first over-labeled fluorescent probe as described herein above. The kit can further comprise at least a second capture antibody specific for a second analyte and a second over-labeled fluorescent probe. Still further, the kit can further comprise at least n additional capture antibodies, each n additional capture antibody specific for a different analyte, and n additional over-labeled fluorescent probes. It will be understood according to well-known principles of immunoassay methodology that a first over-labeled fluorescent probe is specific for the first analyte, the second over-labeled fluorescent probe is specific for the second analyte, and any n additional over-labeled fluorescent probes are each specific for an $n^{th}$ additional analyte. Additionally, the first over-labeled fluorescent probe can be specific for the first capture antibody, the second over-labeled fluorescent probe specific for the second capture antibody, and any n additional over-labeled fluorescent probes each specific for an $n^{th}$ capture antibody. In the immunoassay kit, the first, second and any n additional capture antibodies can be randomly immobilized on the solid support.

More specifically, a kit containing an over-labeled fluorescent probe can contain (1) at least one capture and detection antibody that binds the target analyte or fragment thereof, and together exhibit reduced cross-reactivity with other proteins potentially in the sample, and (2) one or more instructions for performing the immunoassay. The kit can also contain at least one calibrator or control. For example, a kit for detecting or quantifying the amount of Target Analyte A in a sample can include a calibrator or control containing Target Analyte A. A kit can also include quality control reagents (e.g., sensitivity panels or positive controls). Such quality control reagents can be prepared using known and/or varying amount of one or more target analytes, according to methods well known in the art, for example by preparing a solution using a buffer.

A kit can include reagents for preparing the over-labeled fluorescent probes which can be provided in separate containers or otherwise pre-loaded into an appropriate assay support such as a microwell plate.

A kit optionally additionally includes an amount of at least one additional reagent useful in the chemistry involved in conducting an immunoassay or to provide quality control, including one or more reagents useful for generating and/or measuring a signal from the over-labeled fluorescent probes. Kits can optionally include other reagents required to conduct a diagnostic assay or facilitate quality control evaluations, such as for example buffers, reducing agents, antioxidants, a chelating agent, salts, enzymes, enzyme co-factors, substrates, and so on. Kit can also include other components, such as reagents, buffers and solutions, for pretreating a sample. It should be understood that any such additional reagents can be provided in any form or packaging as routinely used in the art, including for example lyophilized reagents, in which case the kit may also include one or more reagents for reconstituting any lyophilized components. Any one or more components of the kit including any reagents may be contained in separate containers such as vials. The contents of each container may be combined and mixed as needed prior to performance of the immunoassay. Other optionally included components of a kit are, for example, reaction vessels, mixing vessels, and instruments and vessels adapted to obtain a sample, such as a syringe, a cotton swab, a pipette, a forceps, a spoon, a paddle, or the like. A kit can further include one or more containers for holding or storing a sample.

The kit further can optionally include instructions for use, which may be provided in a hard copy form or in a computer-readable form, such as written onto a disc, CD, DVD or the like.

In any of the immunoassays and immunoassay kits, the solid support can be a microtiter or microwell plate, a magnetic particle, a bead, a test tube, a cuvette, a film, a filter paper, a membrane, a scaffolding molecule, a disc or a chip.

B. Examples

The following examples are included to demonstrate the disclosure. It should be appreciated by those of skill in the art that the techniques disclosed in the following examples represent techniques discovered by the inventors to function well in the practice of the disclosure. Those of skill in the art should, however, in light of the present disclosure, appreciate that many changes could be made in the disclosure and still obtain a like or similar result without departing from the spirit and scope of the disclosure, therefore all matter set forth is to be interpreted as illustrative and not in a limiting sense.

Example 1: Immunoassays Using Over-Labeled Fluorescent Probes

Figure 4:
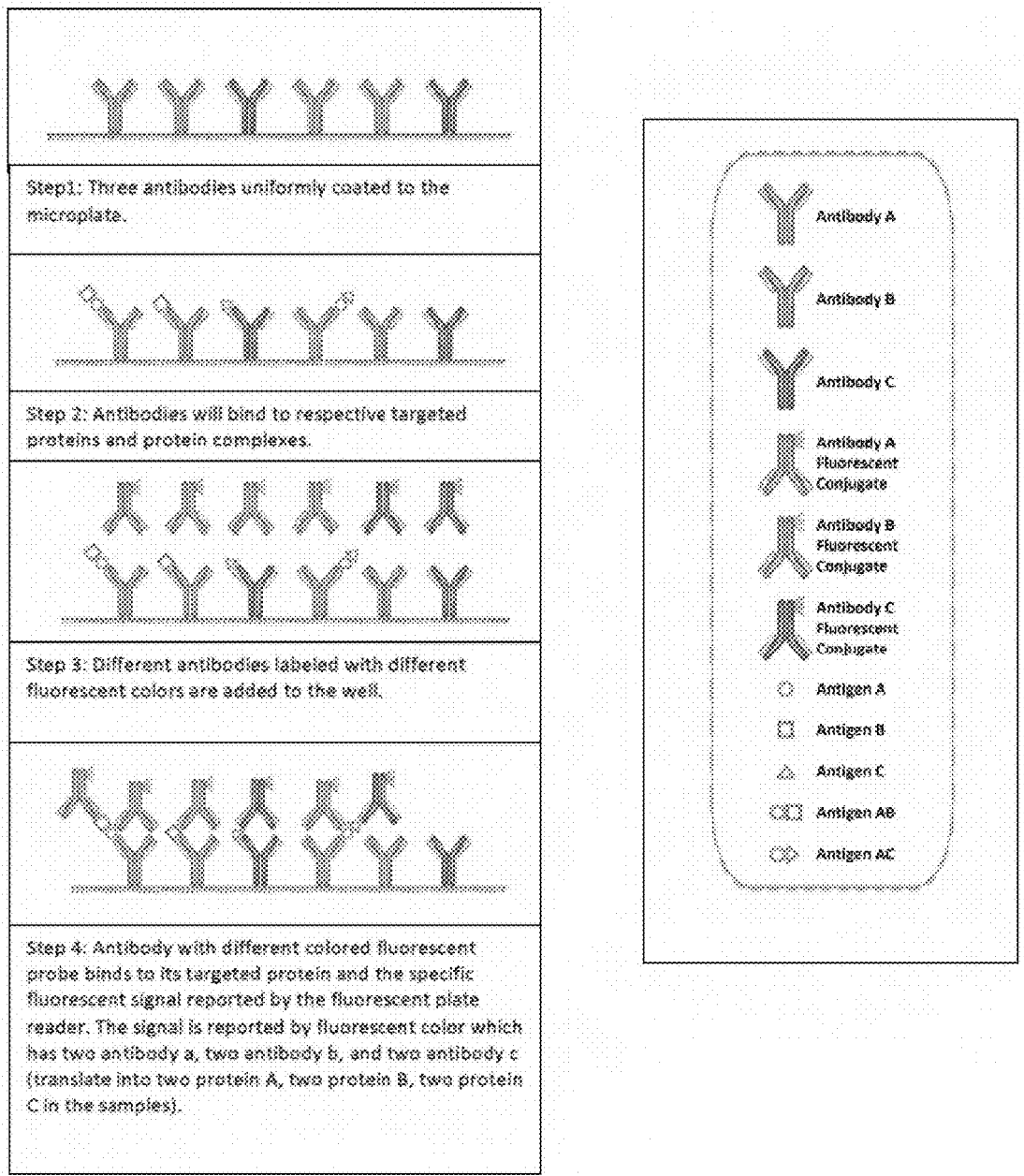
FIG. 4 is a schematic illustration of multiplexing an endpoint fluorescent competitive immunoassay, which demonstrates sufficient resolution to accurately analyze samples including protein complexes.

FIG. 4 is a schematic diagram of immunoassays described herein. In the immunoassays, at least two or more antibodies, each specific for a different target analyte, are coated onto a solid support. As shown in FIG. 4, three different antibodies are used, and these are coated onto a microplate, with no spatial segregation. This can be achieved for example by simply preparing an antibody solution containing a mixture of all the antibodies and contacting the microplate with the solution, leaving the antibodies to adhere to the plate in a random distribution. The plate is then contacted with a sample which may contain multiple target analytes. As shown in Step 2 in FIG. 4, each antibody binds specifically to its corresponding analyte, including instances where the target analyte is non-specifically bound to another antigen or protein in the sample. The three different over-labeled fluorescent probes are then introduced. Each over-labeled fluorescent probe includes the antibody specific for one of the analytes, at least one conjugation moiety, and at least two or more fluorescent moieties. For each different fluorescent probe, the fluorescent moieties are different and provide a fluorescent signal that is distinguishable from that of the fluorescent moieties used in each of the other over-labeled fluorescent probes. As shown in Step 4, each over-labeled fluorescent probe specifically binds to its targeted analyte, and the specific fluorescent signal is reported by a fluorescent plate reader. As shown in this example, the signal is fluorescence generated by the over-labeled fluorescent probes bound to the matching target analyte. For example, as shown in FIG. 4, signal "A" is generated by two "Antibody A's" bound to Antigen A, signal "B" is generated by two "Antibody B's" bound to Antigen B, and signal "C" is generated by two "Antibody C's" bound to Antigen C in the sample.

Example 2: Multiplex Competitive Immunoassays Using Over-Labeled Fluorescent Probes Two multiplex assays based on competitive immunoassay principles and using over-labeled fluorescent probes have been developed: Human/Rat Albumin Fluorescent Multiplex Assay. The multiplex is comprised two of the following assays: a first assay with a first over-labeled fluorescent probe comprising a fluorescent moiety EX488/EM576 (using R-PE1 from phycoerythrins family); a second assay with a second over-labeled fluorescent probe comprising a fluorescent moiety EX620/EM661 (using allophycocyanin); a third assay with a third over-labeled fluorescent probe comprising a fluorescent moiety EX488/EM530 (Thermo Scientific DyLight 488); and a fourth assay with a fourth over-labeled fluorescent probe comprising a fluorescent moiety EX594/EM624 (ATTO 590 from ATTO-TEC GmbH). An assay utilizing a unique fluorescent probe from those mentioned above specific to human albumin is paired with an assay utilizing a different unique fluorescent probe from those mentioned above specific to rat albumin to form a multiplex. Performance is demonstrably equal to or better than a comparable ELISA. The multiplex assay performs the same as the single fluorescence assay.

These assays provide multiplex capability, and can provide quantitative results in about 20 minutes total assay time.

The assays use a 96 strip well plate with removable strips. Three plate readers are used to read the plate: BioTek FLx800, BioTek Synergy H1, and Molecular Devices Gemini XPS.

Example 3: Multiplex Sandwich Immunoassays Using Over-Labeled Fluorescent Probes Two multiplex assays based on sandwich immunoassay principles and using over-labeled fluorescent probes have been developed: Human Complement C5/Complement C6 Fluorescent Multiplex. The multiplex is comprised of two the following assays: a first assay with a first over-labeled fluorescent probe comprising a fluorescent moiety EX488/EM576 (using R-PE1 from phycoerythrins family); a second assay with a second over-labeled fluorescent probe comprising a fluorescent moiety EX620/EM661 (using allophycocyanin); a third assay with a third over-labeled fluorescent probe comprising a fluorescent moiety EX488/EM530 (Thermo Scientific DyLight 488); and a fourth assay with a fourth over-labeled fluorescent probe comprising a fluorescent moiety EX594/EM624 (ATTO 590 from ATTO-TEC GmbH). An assay utilizing a unique fluorescent probe from those mentioned above specific to human complement C5 is paired with an assay utilizing a different unique fluorescent probe from those mentioned above specific to human complement C6 to form a multiplex. Performance is demonstrably equal to or better than a comparable ELISA. These assays provide multiplex capability, and can provide quantitative results in about 40 minutes total assay time. Rather than using array type solid support for multiplexing such as beads, chips, glass slides etc., the immunoassays use a 96 strip well plate with removable strips. Three plate readers are used to read the plate: BioTek FLx800, BioTek Synergy H1, and Molecular Devices Gemini XPS. The assay provides long dynamic range.

Example 4: Antibody and Protein Conjugation

Over-labeled fluorescent probes were prepared by conjugating each specific binding agent to a fluorescence protein or dye or fluorescent peptide.

Materials used include the following:
Human Albumin (Sigma Cat# A9511)
Rat Albumin (Sigma Cat# A6272)
R-Phycocyanins I (R-PE1) (Phyco-Biotech Cat #RPE1)
Dithiothreitol (DTT) (Thermo Scientific Cat #20290)
Allophycocyanin (APC) (Phyco-Biotech Cat #APC)
ATTO 590 EX594/EM624 (ATTO-TEC GmbH Cat # AD 590-35)
DyLight 488 NHS Ester (Thermo Scientific Cat #46403)
DyLight 488 NHS Ester (Thermo Scientific Cat #46402)
Traut's Reagent (2-Iminothiolane.HCl) (Thermo Scientific Cat #26101)
TCEP.HCl, Tris(2-carboxyethyl) phosphine hydrochloride (Thermo Scientific Cat #20490)
Sodium meta-Periodate ((Thermo Scientific Cat #20504)
Sulfo-SMCC (Thermo Scientific Cat #22322)
Sodium azide (Sigma # S2002)
KCKCKCKCKCKCKCK Peptide (custom synthesized by Selleck Chemicals)
2-Mercaptoethanol (Thermo Scientific Cat #. 35600)
Zeba Spin Desalting Columns (Thermo Scientific Cat #89891)
Sulfo-LC-SPDP (Thermo Scientific Cat #21650)
20× Borate Buffer (Thermo Scientific Cat #28341)
Ethylenediaminetetraacetic acid (EDTA)(Sigma Cat # E9884)
Human Albumin Polyclonal Antibody (in house rabbit antibody raised against ultra-pure human albumin purified from human serum)
Rat Albumin Polyclonal Antibody (in house rabbit antibody raised against ultra-pure rat albumin purified from rat serum)
Human Complement C5 Polyclonal Antibody (in house rabbit antibody raised against purified protein from human plasma purchased from The Binding Site Group Ltd, UK)
Human Complement C6 Polyclonal Antibody (in house rabbit antibody raised against purified protein from human plasma purchased from The Binding Site Group Ltd, UK)

Buffers:
PBS (NaCl 137 mM, KCl 2.7 mM, Na2HPO4.2H2O 10 mM, KH2PO4 2.0 mM, pH 7.4)
PBS with 5 mM EDTA pH 8.0
MES buffer: 0.1M MES, 0.5M NaCl, pH 6.0
Coupling Buffer: 50 mL, 0.1M NaHCO3, 0.9% NaCl, pH 9.5

Conjugation of the specific binding agent to a fluorescent protein was achieved using the Sulfo-SDPD method as follows. Equilibrate the vial of SPDP Reagent to room temperature before opening. Dissolve 2 mg reagent in 200 µL of ultrapure water to produce 20 mM stock. Add 25 µL of the 20 mM SPDP solution to 2-5 mg protein (Human albumin, rat albumin, antibody IgG, and fluorescent proteins) dissolved in 1.0 mL of PBS-EDTA. Incubate for 30-60 minutes at room temperature with rotation. Remove nonreacted SPDP reagent using Zeba Spin Desalting Columns follow manufacturer instruction. Modified fluorescence proteins treat with 50 mM DTT in PBS-EDTA buffer for 30 minutes at room temperature with rotation. Remove nonreacted DTT reagent using Zeba Spin Desalting Columns follow manufacturer instruction. Mix modified protein or antibodies with fluorescent proteins for 18 hours at 4 degree with rotation. Labeled protein or antibody is ready to use.

Alternatively, the Sulfo-SMCC and TCEP reagent method was used, as follows. Fluorescent protein 4-5 mg in PBS-EDTA buffer, add 10 mM TCEP in PBS pH 7.4 to the protein in solution and incubate 30 minutes at room temperature. Remove TCEP reagent using Zeba Spin Desalting Columns follow manufacturer instruction. At the same time dissolve protein (Human albumin or rat albumin) or antibody in PBS-EDTA buffer add 50 mole excess to protein or antibody of 2 mg/ml sulfo-smcc. Incubate the reaction for 30 minutes at room temperature with rotation. Remove nonreacted Sulfo-SMCC reagent using Zeba Spin Desalting Columns follow manufacturer instruction. Mix modified protein or antibody with modified fluorescent protein and incubate for 1 hours at room temperature. The conjugate can be further affinity purify with protein A/G column. Labeled protein or antibody is ready to use.

Alternatively, add 10 mM of Sodium meta-Periodate into 5 mg/ml of Fluorescent protein or peptide in PBS buffer for 30 minutes at room temperature. Remove Sodium meta-Periodate reagent using Zeba Spin Desalting Columns follow manufacturer instruction. Make 1 mg/ml IgG in coupling buffer. Mix Fluorescent protein and IgG for reaction at room temperature for 2 hours with rotation. Add 20 mg of lysine to quench the reaction for 2 hours. The conjugate can be further affinity purify with protein A/G column. Labeled protein or antibody is ready to use.

Alternatively, the Sulfo-SMCC and Traut reagent method was used, as follows. Fluorescent protein 4-5 mg in PBS-EDTA buffer, add 20-fold molar excess of Traut's Reagent to the protein in solution and incubate 1 hour at room temperature. Remove nonreacted Traut reagent using Zeba Spin Desalting Columns follow manufacturer instruction. At the same time dissolve protein (Human albumin or rat albumin) or antibody in PBS-EDTA buffer add 50 mole excess to protein or antibody of 2 mg/ml sulfo-smcc. Incubate the reaction for 30 minutes at room temperature with rotation. Remove nonreacted Sulfo-SMCC reagent using Zeba Spin Desalting Columns follow manufacturer instruction. Mix modified protein or antibody with modified fluorescent protein and incubate for 3 hours at room temperature. The conjugate can be further affinity purify with protein A/G column. Labeled protein or antibody is ready to use.

Example 5: Evaluation of Fluorescent Dyes

The performance in the immunoassays of different, readily commercially available fluorescent dyes was compared. Candidate dyes included LI-COR, CF fluorescent dyes, DyLight Dyes, Alexa™ Fluor, CY dyes, ATTO and Chromis dye.

The table below summarizes the performance of the dyes that have been evaluated.

TABLE 2

Dye performance

| Dye Name | Direct conjugation | Indirect conjugation[1] | Peptide conjugation[2] |
|---|---|---|---|
| DyLight 350 | Did not work | Not evaluated | Not evaluated |
| DyLight 405 | Worked poorly | Not evaluated | Not evaluated |
| DyLight 488 | Excellent | Worked well | Worked well |
| DyLight 594 | Did not work | Not evaluated | Not evaluated |
| DyLight 633 | Worked poorly | Not evaluated | Not evaluated |
| DyLight 650 | Did not work | Not evaluated | Not evaluated |
| ATTO 390 | Worked slightly | Worked | Worked |
| ATTO 425 | Did not work | Did not work | Did not work |
| ATTO 495 | Did not work | Did not work | Did not work |
| ATTO Rho6G | Did not work | Did not work | Did not work |
| ATTO 565 | Worked slightly | Worked | Not evaluated |
| ATTO 590 | Worked slightly | Worked | Not evaluated |
| ATTO 620 | Did not work | Did not work | Not evaluated |
| ATTO 430LS | Worked slightly | Worked | Not evaluated |
| ATTO 490LS | Worked slightly | Worked | Not evaluated |

Note:
[1]Indirect conjugation: Make BSA as fluorescent protein and then conjugate fluorescent BSA to targeted protein or antibody
[2]Peptide conjugation: special peptide KCKCKCKCKCKCKCK has been developed and label lysine with dyes and conjugate the peptide to protein or antibody through the cystein-sh group.

DyLight dyes and Atto dyes were further evaluated, as follows. Chromis dye can also be comparably prepared.

Figure 5:
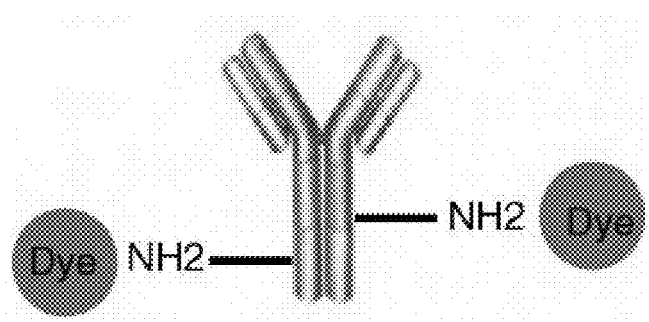
FIG. 5 is a schematic illustration of dye conjugation to an antibody to produce an antibody-based over-labeled fluorescent probe.

DyLight 488 NHS Ester Protocol:

Direct label Pierce DyLight 488 (Cat #46403) add 250 μl of DMSF (Sigma # D5879), antibody at concentration of 1 mg/ml with 1× borate buffer and then add 50 μl of dye to the antibody and react with 2 hours at room temperature and then dialysis using spectra/por tubing (cat #132706) to dialysis with PBS pH 7.4 at 4 degree in the dark for two days. See FIG. 5.

Figure 6:
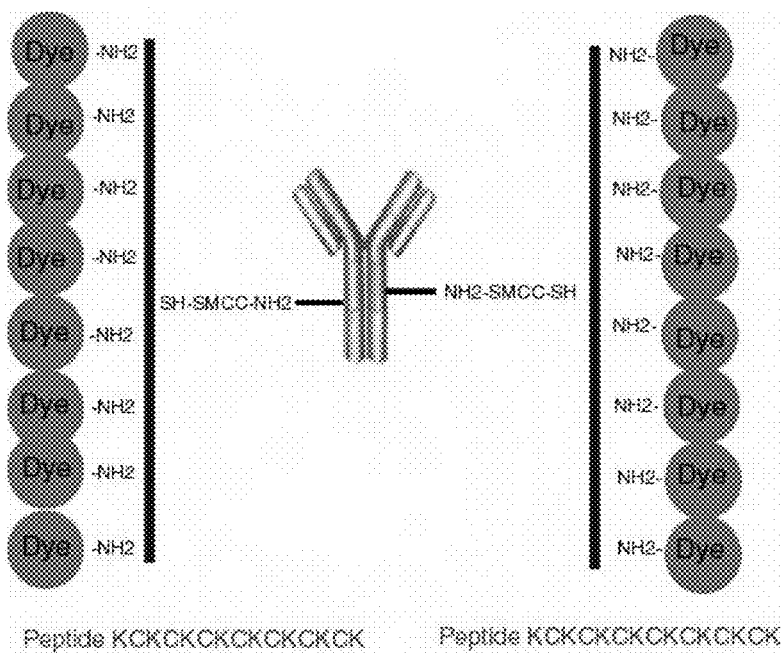
FIG. 6 is a schematic illustration of fluorescent peptide conjugation to an antibody using Protocol A.

Fluorescent Peptide Conjugation Method:

This is a unique approach to the conjugation in which a peptide is labeled with a fluorescent dye to form a fluorescent peptide which is then conjugated to the protein or antibody. This was achieved as follows:

Protocol A:

Dissolved 1 mg peptide KCKCKCKCKCKCKCK in PBS-EDTA buffer and add 100 ug dyes in DMSF to the peptide solution and react 1 hour at room temperature with rotation. Dialysis: the reaction used spectra/por tubing (cat #132625) against PBS-EDTA with stir at room temperature for 4 hours. At the same time dissolve protein (Human albumin or rat albumin) or antibody in PBS-EDTA buffer add 50 mole excess to protein or antibody of 2 mg/ml sulfo-smcc. Incubate the reaction for 30 minutes at room temperature with rotation. Remove nonreacted Sulfo-SMCC reagent using Zeba Spin Desalting Columns follow manufacturer instruction. Mix Maleimide activated protein or antibody with peptides and then incubates for 2 hours at room temperature. Conjugation is ready to use. See FIG. 6.

Protocol B:

Materials:
Sodium meta-periodate (Thermo Scientific cat#. 20504)
Oxidation Buffer: 0.1M sodium acetate, pH 5.5

Dissolved 1 mg peptide KCKCKCKCKCKCKCK in PBS-EDTA buffer and add 100 ug dyes in DMSF to the peptide solution and react 1 hour at room temperature with rotation. Dialysis the reaction used spectra/por tubing (cat #132625) against PBS-EDTA with stir at room temperature for 2 hours.

Add 1 ml DMSF to 3 mg BMPH to become 10 mM solution. Add 20-fold molar excess of reagent over fluorescent peptide in PBS-EDTA. Incubate reaction mixture for 2 hours at room temperature. Remove nonreacted BMPH reagent using Zeba Spin Desalting Columns follow manufacturer instruction.

Figure 7:
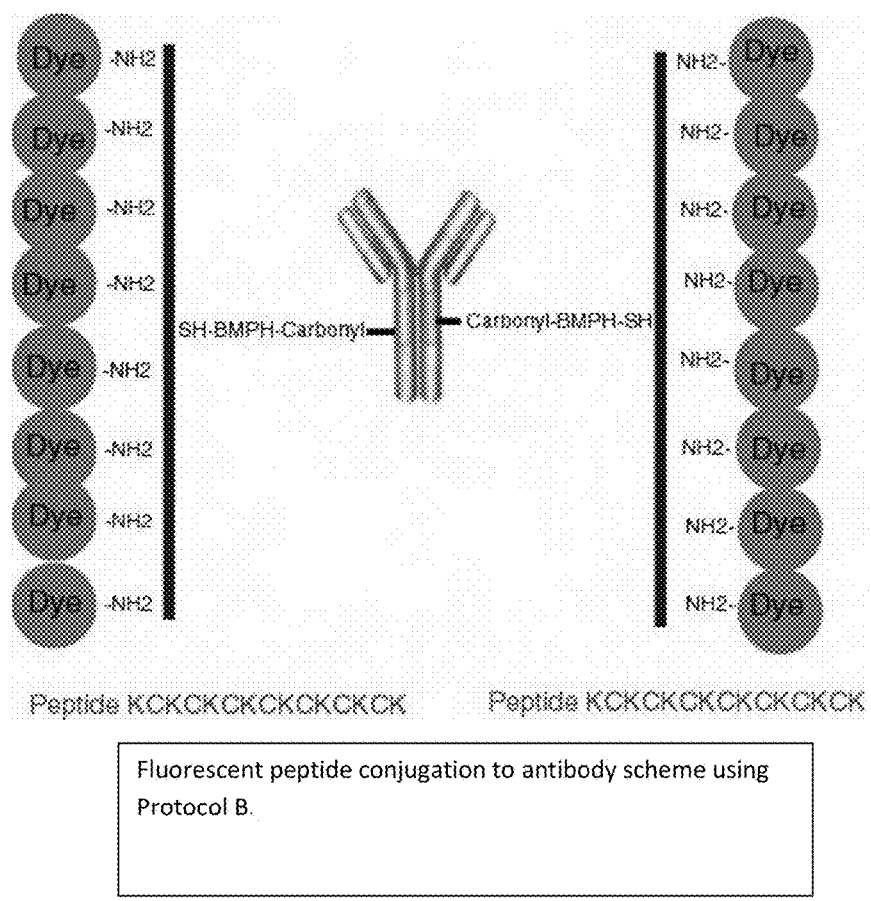
FIG. 7 is a schematic illustration of fluorescent peptide conjugation to an antibody using Protocol B.

At the same time, prepare 20 mM periodate solution by dissolving 4.3 mg of sodium meta-periodate per milliliter of Oxidation Buffer. Prepare a volume equal to the volume of protein or IgG solution. Keep solution on ice and protect it from light. Add 1 mL of cold sodium meta-periodate solution to 1 mL of the protein or IgG solution and mix well. Allow the oxidation reaction to proceed for 30 minutes in the dark on ice or at 4° C. Remove nonreacted periodate reagent using Zeba Spin Desalting Columns follow manufacturer instruction. Mix BMPH modified fluorescent peptide with oxidized protein or IgG together and incubate reaction mixture for 2 hours at room temperature. The conjugate is ready to use. See FIG. 7.

Dye Label Protein to Become Fluorescent Proteins to Conjugate Antibody or Protein:

Protocol A:

Dissolve 1 mg ATTO 590 dye in 250 μl DMSF and add 100 μl to 5 mg/ml BSA in PBS to incubate for 2 hours and then dialysis overnight in MES buffer at 4 degree.

Figure 8:
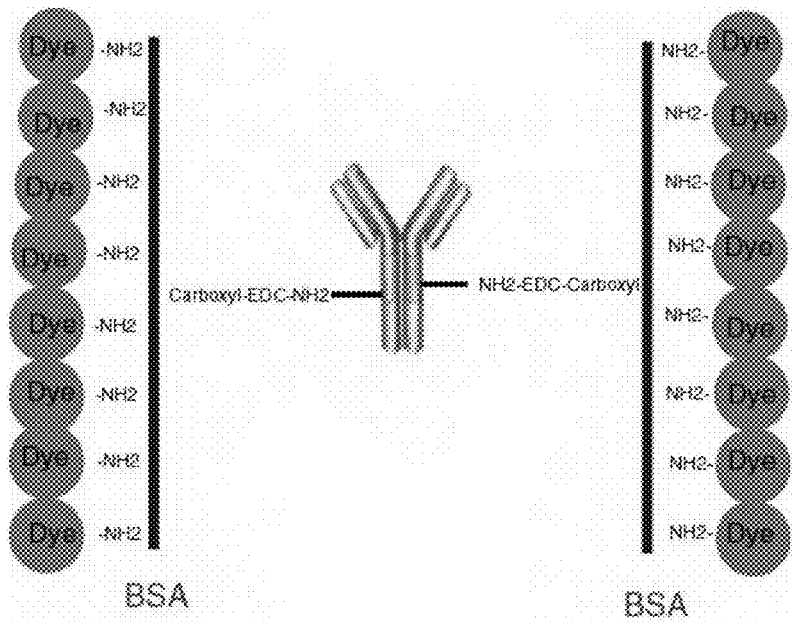
FIG. 8 is a schematic illustration of fluorescent BSA conjugation to an antibody using Protocol A.

Add 0.4 mg EDC (~2 mM) and 1.1 mg of sulfo-NHS (~5 mM) to 1 mL of fluorescent BSA 5 mg/ml solution and react for 15 minutes at room temperature. Add 1.4 μL of 2-mercaptoethanol (final concentration of 20 mM) to quench the EDC. Remove nonreacted EDC and 2-mercaptoethanol reagent using Zeba Spin Desalting Columns follow manufacturer instruction. Mix fluorescent BSA 5 mg/ml to 1 mg/ml IgG and react for 1 hour at room temperature with rotation. Labeled antibody is ready to use. See FIG. 8.

Protocol B:

Dissolve 1 mg ATTO 590 dye in 250 μl DMSF and add 100 μl to 5 mg/ml BSA in PBS to incubate for 2 hours and then dialysis overnight in PBS buffer at 4 degree.

Add 4 mM of DTT to 1 mL of fluorescent BSA 5 mg/ml in PBS-EDTA buffer and react for 2 hours at 37 degree. Remove DTT using Zeba Spin Desalting Columns follow manufacturer instruction.

Add 1 ml DMSF to 3 mg BMPH to become 10 mM solution. Add 20-fold molar excess of reagent over fluorescent protein in PBS-EDTA. Incubate reaction mixture for 2 hours at room temperature. Remove nonreacted BMPH reagent using Zeba Spin Desalting Columns follow manufacturer instruction. At the same time, prepare 20 mM periodate solution by dissolving 4.3 mg of sodium meta-periodate per milliliter of Oxidation Buffer. Prepare a volume equal to the volume of protein or IgG solution. Keep solution on ice and protect it from light.

Figure 9:
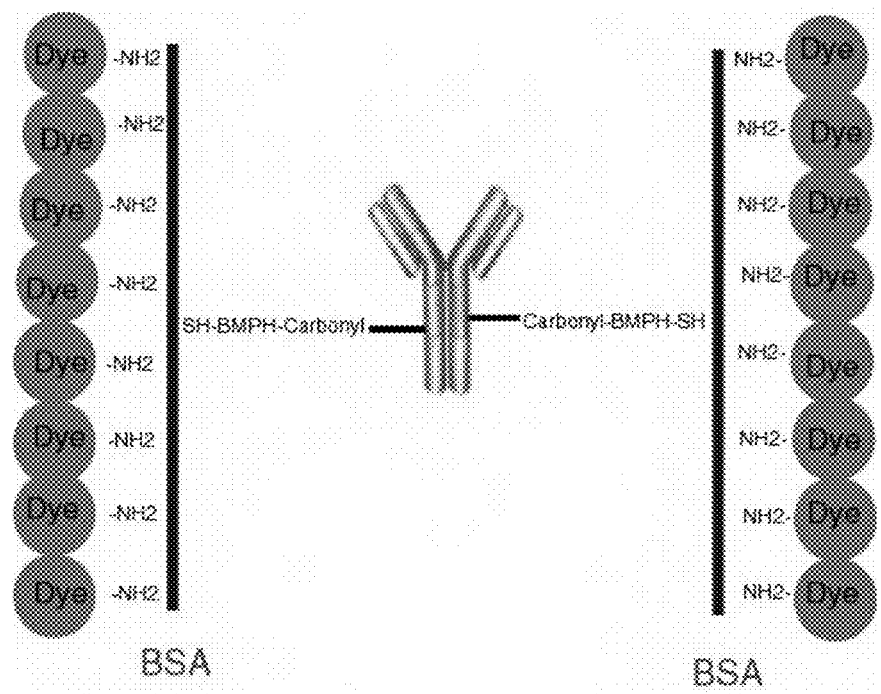
FIG. 9 is a schematic illustration of fluorescent BSA conjugation to an antibody using Protocol B.

At the same time, add 1 mL of cold sodium meta-periodate solution to 1 mL of the protein or IgG solution and mix well. Allow the oxidation reaction to proceed for 30 minutes in the dark on ice or at 4° C. Remove nonreacted periodate reagent using Zeba Spin Desalting Columns follow manufacturer instruction. Mix BMPH modified fluorescent BSA with oxidized protein or IgG together and incubate reaction mixture for 2 hours at room temperature. The conjugate is ready to use. See FIG. 9.

Protocol C:
Materials:
Sodium meta-periodate (available from Thermo Scientific, cat. #20504)
Coupling Buffer: 50 mL, 0.1M NaHCO3, 0.9% NaCl, pH 9.5

Dissolve 1 mg ATTO 590 dye in 250 µl DMSF and add 100 µl to 5 mg/ml BSA in PBS to incubate for 2 hours and then dialysis overnight in PBS pH 7.4 at 4 degree.

Add Sodium meta-periodate to 1 mL of fluorescent BSA 5 mg/ml in PBS pH 7.4 to be 10 mM final Sodium meta-periodate and reaction at room temperature for 30 minutes with rotation. Remove Sodium meta-Periodate reagent using Zeba Spin Desalting Columns follow manufacturer instruction.

Figure 9A:
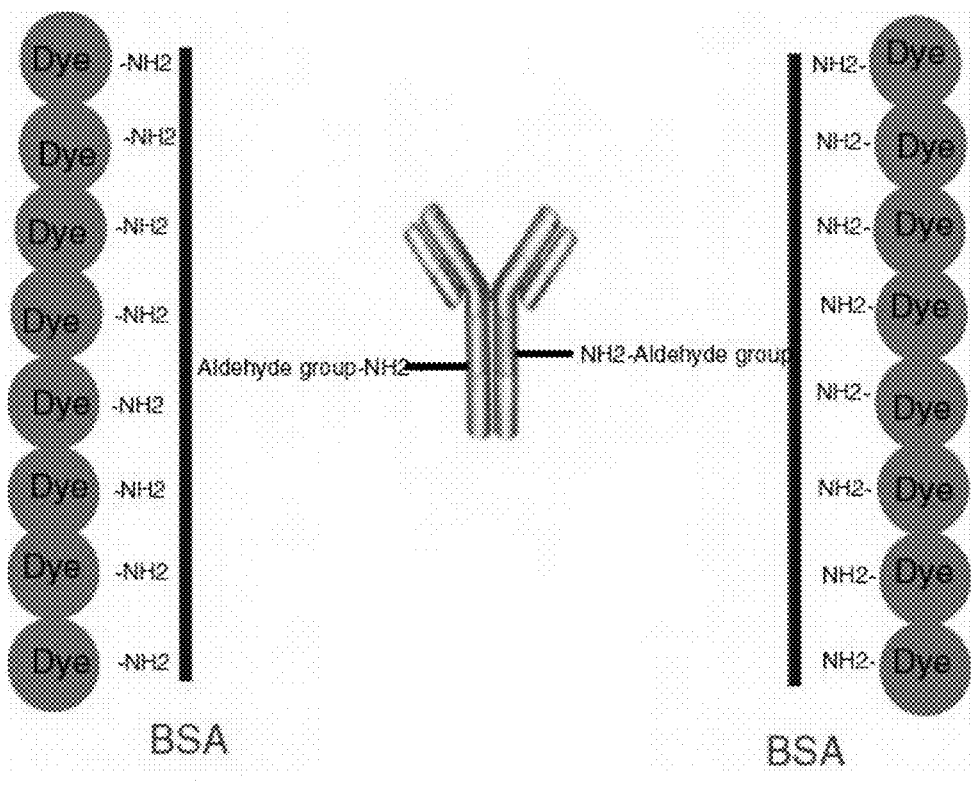

Make 1 mg/ml of IgG in Coupling Buffer, Add activated fluorescent BSA to the antibody and incubate for 2 hours at room temperature. Add 20 mg of lysine to quench the reaction for 2 hours. The conjugate can be further affinity purify with protein A/G column. Labeled protein or antibody is ready to use. See FIG. 9*a*.

Example 6: Comparison of Immunoassays

Human Albumin Assays-Materials.
Human Albumin (Sigma Cat# A9511)
Sulfo-SMCC (Thermo Scientific Cat #22322)
20× Borate Buffer (Thermo Scientific Cat #28341)
Ethylenediaminetetraacetic acid (EDTA)(Sigma Cat # E9884)
Human Albumin Polyclonal Antibody (in house rabbit antibody raised against ultra-pure human albumin purified from human serum)
Buffers:
PBS—NaCl 137 mM, KCl 2.7 mM, Na2HPO4.2H2O 10 mM, KH2PO4 2.0 mM, pH 7.4
FAB—PBS with 0.02% BSA and 0.02% Sodium Azide
Wash—PBS with 0.1% TWEEN®-20 and 0.02% Sodium Azide
SuperBlock Blocking Buffer in PBS (Thermo Scientific Cat#37518)
Current ELISA Protocol:
The microplate is coated with a polyclonal antibody specific for Human Albumin at a concentration of 5 µg/ml. The plate is then blocked with 300 pl of blocking buffer for 4 minutes. The lyophilized Human Albumin protein is prepared by reconstituting it with 1 ml FAB. Duplicate standard points are prepared by serially diluting the standard (200 µg/ml) 1:4 with FAB to generate 50, 12.5, 3.125, and 0.781 µg/ml solutions. FAB serves as the zero standard (0 µg/ml).

A biotinylated protein specific for Human Albumin is reconstituted with 4 ml FAB to create an 8-fold stock solution. The protein is then further diluted 1:8 with FAB.

A Streptavidin-peroxidase conjugate is diluted 1:100 with FAB.

A ready-to-use stabilized peroxidase chromogen substrate tetramethylbenzidine (TMB) is used at 1×.

Lastly, 0.5 N hydrochloric acid is used to stop the chromogen substrate reaction.

Human plasma and serum are diluted 1:10000 in FAB by two 1:100 serial dilutions, the Common Reference is reconstituted with 1 ml of FAB and further diluted 1:500 in FAB, and the Fixed Reference is reconstituted with 1 ml of FAB and used as 1×. The ELISA assay was performed as diagrammed in FIG. 58.

Current APC Fluorescent Protocol:
The microplate is coated with a polyclonal antibody specific for Human Albumin at a concentration of 5 µg/ml. The plate is then blocked with 300 µl of blocking buffer for 4 minutes. The lyophilized Human Albumin protein is prepared by reconstituting it with 1 ml FAB. Duplicate standard points are prepared by serially diluting the standard (200 µg/ml) 1:4 with FAB to generate 50, 12.5, 3.125, and 0.781 µg/ml solutions. FAB serves as the zero standard (0 µg/ml).

An APC fluorescent probe specific for Human Albumin is diluted 1:20 with FAB.

Human plasma and serum are diluted 1:10000 in FAB by two 100× serial dilutions, the Common Reference is reconstituted with 1 ml of FAB and further diluted 1:500 in FAB, and the Fixed Reference is reconstituted with 1 ml of FAB and loaded as 1×. The APC assay was performed as diagrammed in FIG. 59.

Current RPE Fluorescent Protocol:
The microplate is coated with a polyclonal antibody specific for Human Albumin at a concentration of 5 µg/ml. The plate is then blocked with 300 µl of blocking buffer for 4 minutes. The lyophilized Human Albumin protein is prepared by reconstituting it with 1 ml FAB. Duplicate standard points are prepared by serially diluting the standard (200 µg/ml) 1:4 with FAB to generate 50, 12.5, 3.125, and 0.781 µg/ml solutions. FAB serves as the zero standard (0 pg/ml).

A RPE fluorescent probe specific for Human Albumin is diluted 1:100 with FAB.

Human plasma and serum are diluted 1:10000 in FAB by two 100× serial dilutions, the Common Reference is reconstituted with 1 ml of FAB and further diluted 1:500 in FAB, and the Fixed Reference is reconstituted with 1 ml of FAB and loaded as 1×. The RPE assay was performed as diagrammed in FIG. 60.

Current APC Multiplex Protocol:
The microplate is coated with a polyclonal antibody specific for Human Albumin at a concentration of 6 µg/ml and 8.4 µ/ml Ratbumin. The plate is then blocked with 300 µl of blocking buffer for 4 minutes. The lyophilized Human Albumin protein is prepared by reconstituting it with 0.5 ml Fluorescent Assay Buffer (FAB). The Rat Albumin Standard (20 mg/ml) is diluted 1:50 with FAB. The Human Albumin (400 µg/ml) and the Rat Albumin standards are then mixed together in a v/v ratio creating a single 200 µg/ml Human, 200 µg/ml Rat Albumin working solution. Duplicate standard points are prepared by serially diluting the standard (Human/Rat 200 µg/ml) 1:4 with FAB to generate 50, 12.5, 3.125, and 0.781 µg/ml solutions. FAB serves as the zero standard (0 µg/ml).

An APC fluorescent probe specific for Human Albumin is diluted 1:10 with FAB. An RPE fluorescent probe specific for Rat Albumin is diluted 1:10 with FAB.

Human and Rat plasma and serum are diluted 1:10000 in FAB by two 100× serial dilutions, Human and Rat Urine samples are diluted 1:2 in FAB, the Human Common Reference reconstituted with 1 ml of FAB and further diluted 1:500 in FAB, and the Human Fixed Reference and the Human Urine Reference are reconstituted with 1 ml of FAB and loaded as 1×. The Rat Common Reference is reconstituted with 1 ml FAB and further diluted 1:600 in FAB. The APC multiplex assay was performed as diagrammed in FIG. 61.

Current RPE Multiplex Protocol:

The microplate is coated with a polyclonal antibody specific for Human Albumin at a concentration of 6 µg/ml and 8.4 µ/ml Rat Albumin. The plate is then blocked with 300 µl of blocking buffer for 4 minutes. The lyophilized Human Albumin protein is prepared by reconstituting it with 0.5 ml Fluorescent Assay Buffer (FAB). The Rat Albumin Standard (20 mg/ml) is diluted 1:50 with FAB. The Human Albumin (400 µg/ml) and the Rat Albumin standards are then mixed together in a v/v ratio creating a single 200 µg/ml Human, 200 µg/ml Rat Albumin working solution. Duplicate standard points are prepared by serially diluting the standard (Human/Rat 200 µg/ml) 1:4 with FAB to generate 50, 12.5, 3.125, and 0.781 µg/ml solutions. FAB serves as the zero standard (0 µg/ml).

An RPE fluorescent probe specific for Human Albumin is diluted 1:50 with FAB. An APC fluorescent probe specific for Rat Albumin is diluted 1:10 with FAB.

Human and Rat plasma and serum are diluted 1:10000 in FAB by two 100× serial dilutions, Human and Rat Urine samples are diluted 1:2 in FAB, the Human Common Reference reconstituted with 1 ml of FAB and further diluted 1:500 in FAB, and the Human Fixed Reference and the Human Urine Reference are reconstituted with 1 ml of FAB and loaded as 1×. The Rat Common Reference is reconstituted with 1 ml FAB and further diluted 1:600 in FAB. The RPE multiplex assay was performed as diagrammed in FIG. 62.

The Human Albumin assay as described above demonstrated that the new assay system described herein using an over-labeled fluorescent probe performs similarly to the ELISA system.

Figure 10:
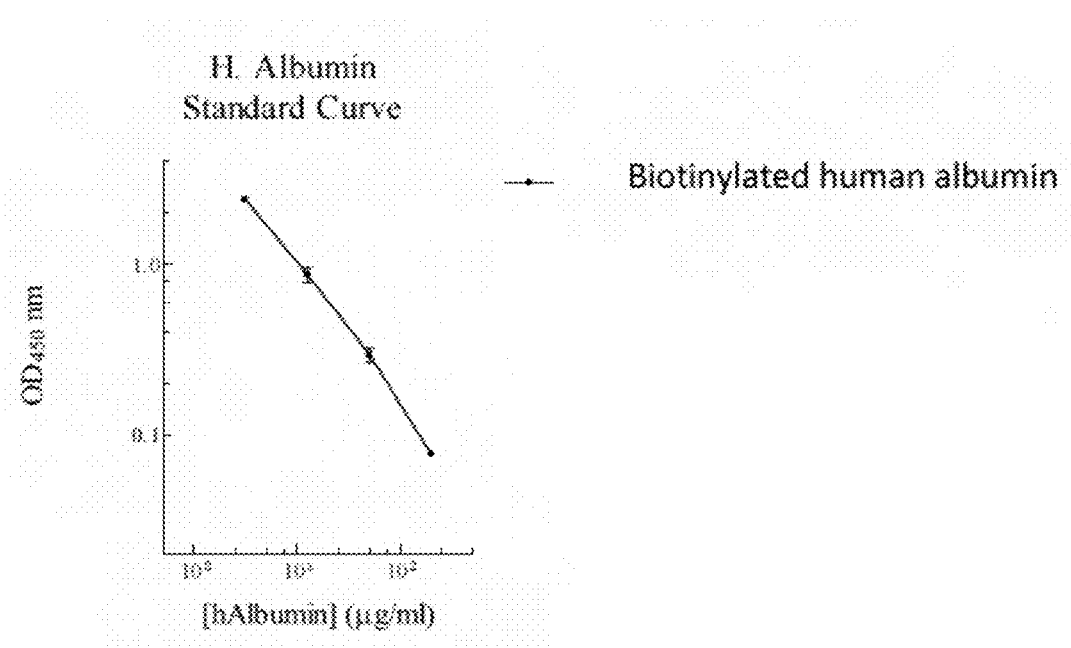
FIG. 10 is a standard curve generated from data obtained using an ELISA system and a biotinylated human albumin, using competitive immunoassay techniques and reading with the Molecular Devices SpectraMax 340PC microplate reader.
Figure 11:
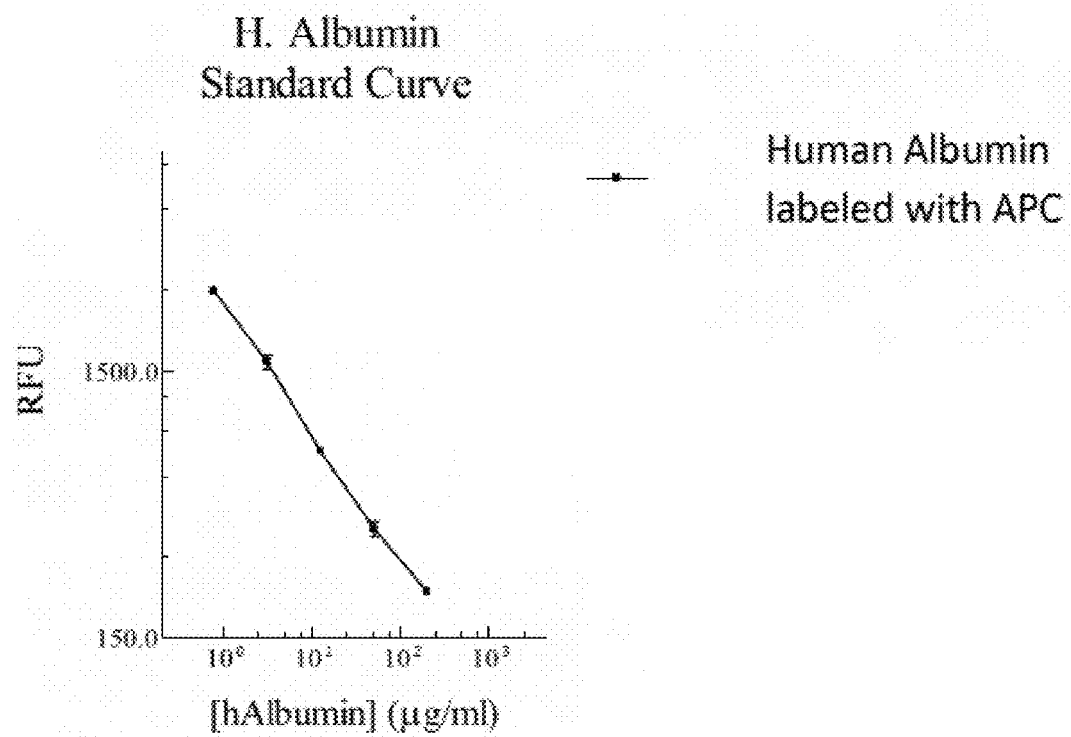
FIG. 11 is a standard curve generated from data obtained using the disclosed assay technique using a human albumin over-labeled with APC, evaluated by reading with the BioTek FLx800 microplate reader.
Figure 12:
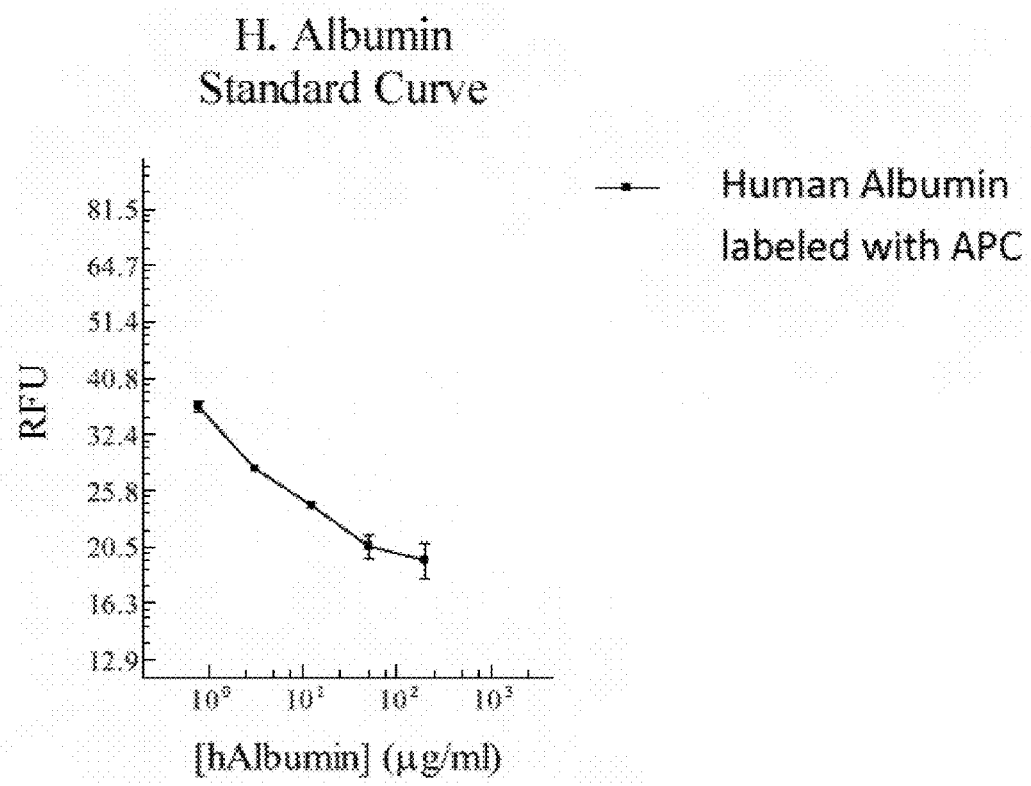
FIG. 12 is a standard curve generated from data obtained using the disclosed assay technique performed using a human albumin over-labeled with APC, evaluated by reading with the Molecular Devices Gemini XPS microplate reader.
Figure 13:
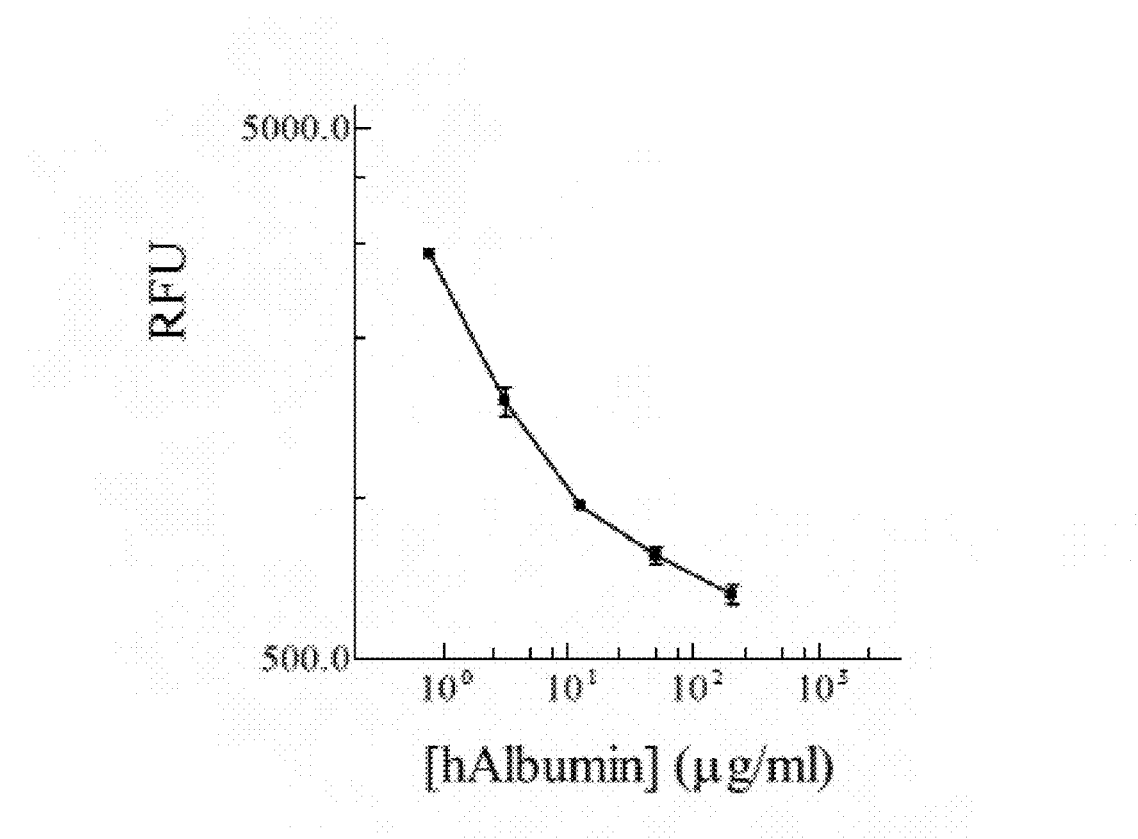
FIG. 13 is a standard curve generated from data obtained using the disclosed assay technique using a human albumin over-labeled with RPE1, evaluated by reading with the BioTek FLx800 microplate reader.
Figure 14:
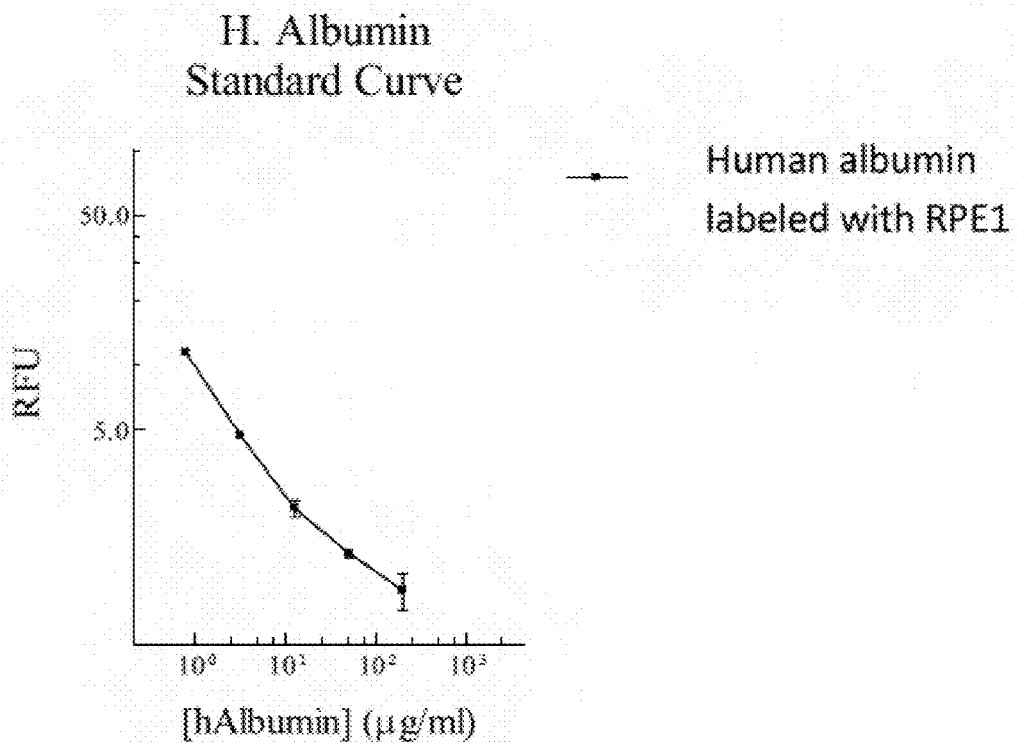
FIG. 14 is a standard curve generated from data obtained using the disclosed assay technique performed using a human albumin over-labeled with RPE1, evaluated by reading with the Molecular Devices Gemini XPS microplate reader.

Human albumin ELISA system performance using competitive immunoassay techniques and reading with Molecular Devices SpectraMax 340PC microplate reader has been evaluated (FIG. 10). The new human albumin assay system using APC or RPE1 labeled protein as the tracer to perform competitive immunoassay was evaluated by reading with the BioTek FLx800 microplate reader (FIG. 11, 13) and Molecular Devices Gemini XPS microplate reader (FIG. 12, 14). The results show that the performance of the new system in human albumin determination is similar to that of an ELISA kit. The performance characterization is summarized in Table 3 below:

TABLE 3

ELISA performance vs. new assay system in the competitive immunoassay system to determine human albumin

| | ELISA System | APC/Gemini XPS | APC/FLx800 | RPE1/Gemini XPS | RPE1/FLx800 |
|---|---|---|---|---|---|
| Standard Range | 200-3.125 µg/ml | 200-0.781 µg/ml | 200-0.781 µg/ml | 200-0.781 µg/ml | 200-0.781 µg/ml |
| Intra-assay CV | 3.7 | 3.0 | 7.2 | 5.7 | 10.6 |
| Inter-assay CV | 12.2 | 15.0 | 16.4 | 16.9 | 14.1 |
| Sample value | 52069.1 µg/ml | 50320.8 µg/ml | 52017.6 µg/ml | 53432.3 µg/ml | 50983.8 µg/ml |
| Sensitivity | 3.125 µg/ml | 0.781 µg/ml | 0.781 µg/ml | 0.781 µg/ml | 0.781 µg/ml |

Human albumin assays were used to demonstrate the performance similarity of the ELISA and new multiplex series assays using over-labeled fluorescent probes.

To demonstrate the multiplex capability, a rat albumin assay system has been developed and characterized against the ELISA system.

Rat Albumin Assays:
Materials:
Rat Albumin (Sigma Cat# A6272)
Rat Albumin Polyclonal Antibody (in house rabbit antibody raised against ultra-pure rat albumin purified from rat serum)
Buffers:
PBS—NaCl 137 mM, KCl 2.7 mM, Na2HPO4.2H2O 10 mM, KH2PO4 2.0 mM, pH 7.4
FAB—PBS with 0.02% BSA and 0.02% Sodium Azide
Wash—PBS with 0.1% TWEEN®-20 and 0.02% Sodium Azide
SuperBlock Blocking Buffer in PBS (Thermo Scientific Cat#37518)

Current ELISA Protocol:
The microplate is coated with a polyclonal antibody specific for Rat Albumin at 7 µg/ml. The plate is then blocked with 300 µl of blocking buffer for 4 minutes. The Rat Albumin protein is prepared in duplicate standard points by serially diluting the standard (10 mg/ml) 1:50 to produce the first standard point of 200 µg/ml, and then 1:4 with FAB to generate 50, 12.5, 3.13, 0.78 µg/ml solutions. FAB serves as the zero standard (0 µg/ml).

Biotinylated Rat Albumin is reconstituted with 5 ml FAB to produce a 2-fold stock solution. The stock solution is further diluted 1:4 with FAB.

The Streptavidin-Peroxidase Conjugate is spun down briefly and diluted to the desired amount of conjugate 1:100 with FAB.

A ready-to-use stabilized peroxidase chromogen substrate tetramethylbenzidine (TMB) is used at 1×.

Lastly, 0.5 N hydrochloric acid is used to stop the chromogen substrate reaction.

Rat plasma and serum are diluted 1:10000 in FAB, rat urine is diluted 1:2 in FAB, and rat reference is reconstituted with 1 ml of FAB and further diluted 1:600 in FAB. The ELISA assay was performed as diagrammed in FIG. 63.

Current APC Fluorescent Protocol:

The microplate is coated with a polyclonal antibody specific for Rat Albumin at 7 µg/ml. The plate is then blocked with 300 µl of blocking buffer for 4 minutes. The Rat Albumin protein is prepared in duplicate standard points by serially diluting the standard (10 mg/ml) 1:50 to produce the first standard point of 200 µg/ml, and then 1:4 with fluorescent assay buffer (FAB) to generate 50, 12.5, 3.13, 0.78 µg/ml solutions. FAB serves as the zero standard (0 µg/ml).

A fluorescent protein specific to Rat Albumin is diluted 1:20 with FAB.

Rat plasma and serum are diluted 1:10000 in FAB, rat urine is diluted 1:2 in FAB, and rat reference is reconstituted with 1 ml of FAB and further diluted 1:600 in FAB. The APC assay was performed as diagrammed in FIG. 64.

Current RPE Fluorescent Protocol:

The microplate is coated with a polyclonal antibody specific for Rat Albumin at 7 µg/ml. The plate is then blocked with 300 µl of blocking buffer for 4 minutes. The Rat Albumin protein is prepared in duplicate standard points by serially diluting the standard (10 mg/ml) 1:50 to produce the first standard point of 200 µg/ml, and then 1:4 with fluorescent assay buffer (FAB) to generate 50, 12.5, 3.13, 0.78 µg/ml solutions. FAB serves as the zero standard (0 µg/ml).

A fluorescent protein specific to Rat Albumin is diluted 1:20 with FAB.

Rat plasma and serum are diluted 1:10000 in FAB, rat urine is diluted 1:2 in FAB, and rat reference is reconstituted with 1 ml of FAB and further diluted 1:600 in FAB. The RPE assay was performed as diagrammed in FIG. 65.

Current APC Multiplex Protocol:

The microplate is coated with two polyclonal antibodies specific for Rat Albumin at 8.4 µg/ml and Human Albumin at 6 µg/ml. The plate is then blocked with 300 µl of blocking buffer for 4 minutes. The Rat Albumin standard protein is diluted 1:25 from 10 mg/ml to a concentration of 100 µg/ml and Human Albumin standard protein is reconstituted with 0.5 ml of FAB to a concentration of 200 µg/ml. Both Rat Albumin and Human Albumin are then combined into a 1:2 dilution to make the first standard point and then 1:4 with fluorescent assay buffer (FAB) to generate 50, 12.5, 3.13, 0.78 µg/ml solutions. FAB serves as the zero standard (0 µg/ml).

Next, Human RPE fluorescent protein is diluted 1:50 with FAB, and Rat APC is diluted 1:10 with FAB. Once these dilutions are prepared the Human RPE and Rat APC fluorescent proteins are combined together as one solution.

Rat plasma and serum are diluted 1:10000 in FAB, rat urine is diluted 1:2 in FAB, and rat reference is reconstituted with 1 ml of FAB and further diluted 1:600 in FAB. The APC multiplex assay was performed as diagrammed in FIG. 66.

Current RPE Multiplex Protocol:

The microplate is coated with two polyclonal antibodies specific for Rat Albumin at 8.4 µg/ml and Human Albumin at 6 µg/ml. The plate is then blocked with 300 µl of blocking buffer for 4 minutes. The Rat Albumin standard protein is diluted 1:25 from 10 mg/ml to a concentration of 100 µg/ml and Human Albumin standard protein is reconstituted with 0.5 ml of FAB to a concentration of 200 µg/ml. Both Rat Albumin and Human Albumin are then combined into a 1:2 dilution to make the first standard point and then 1:4 with fluorescent assay buffer (FAB) to generate 50, 12.5, 3.13, 0.78 µg/ml solutions. FAB serves as the zero standard (0 µg/ml).

Next, Human APC fluorescent protein is diluted 1:10 with FAB and Rat RPE fluorescent protein is diluted 1:10 with FAB. Once these dilutions are prepared the Human APC and Rat RPE fluorescent proteins are combined together as one solution.

Rat plasma and serum are diluted 1:10000 in FAB, rat urine is diluted 1:2 in FAB, and rat reference is reconstituted with 1 ml of FAB and further diluted 1:600 in FAB. The RPE multiplex assay was performed as diagrammed in FIG. 67.

Figure 15:
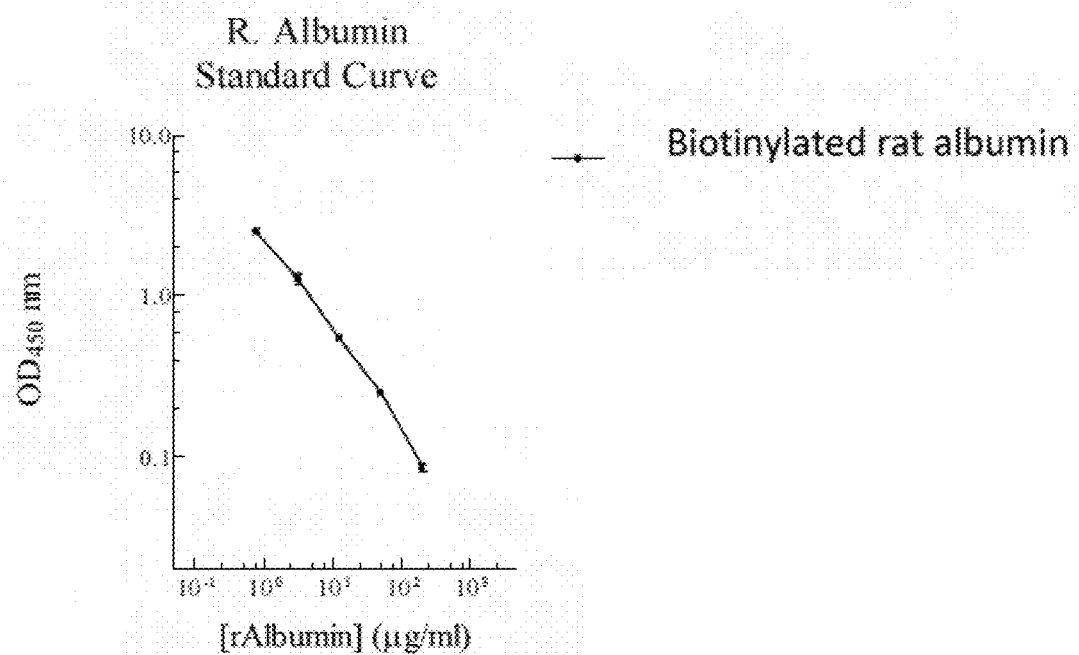
FIG. 15 is a standard curve generated from data obtained using an ELISA system and a biotinylated rat albumin, using competitive immunoassay techniques and reading with Molecular Devices SpectraMax 340PC microplate reader.
Figure 16:
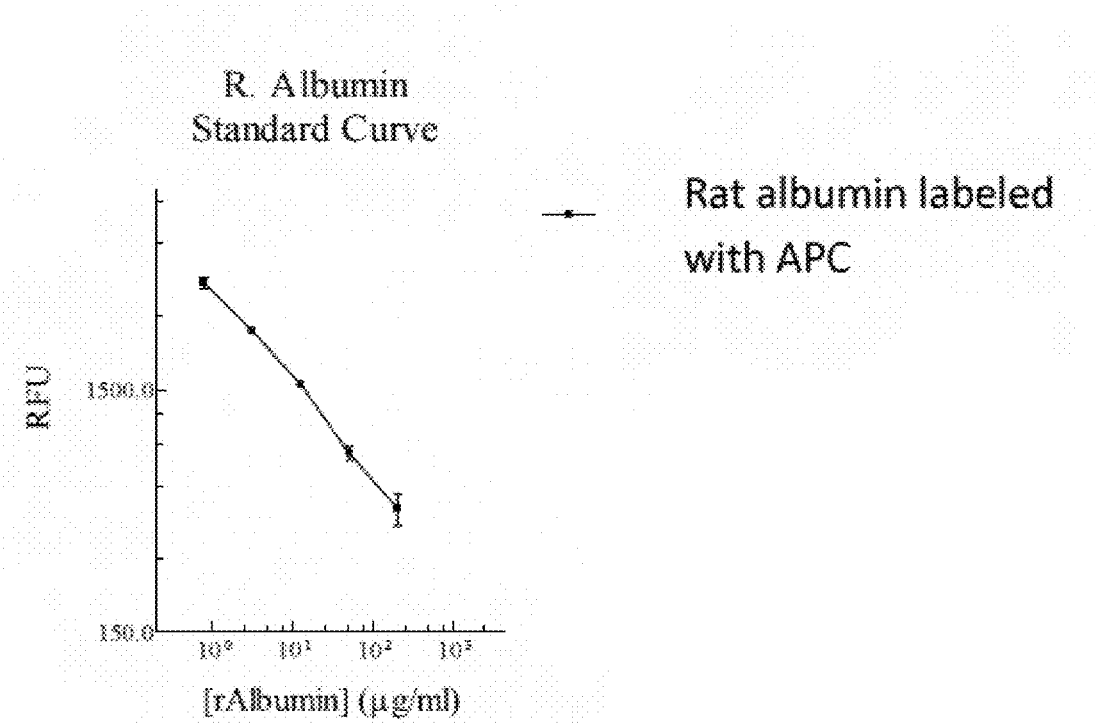
FIG. 16 is a standard curve generated from data obtained using the disclosed assay technique using a rat albumin over-labeled with APC, evaluated by reading with the BioTek FLx800 microplate reader.
Figure 17:
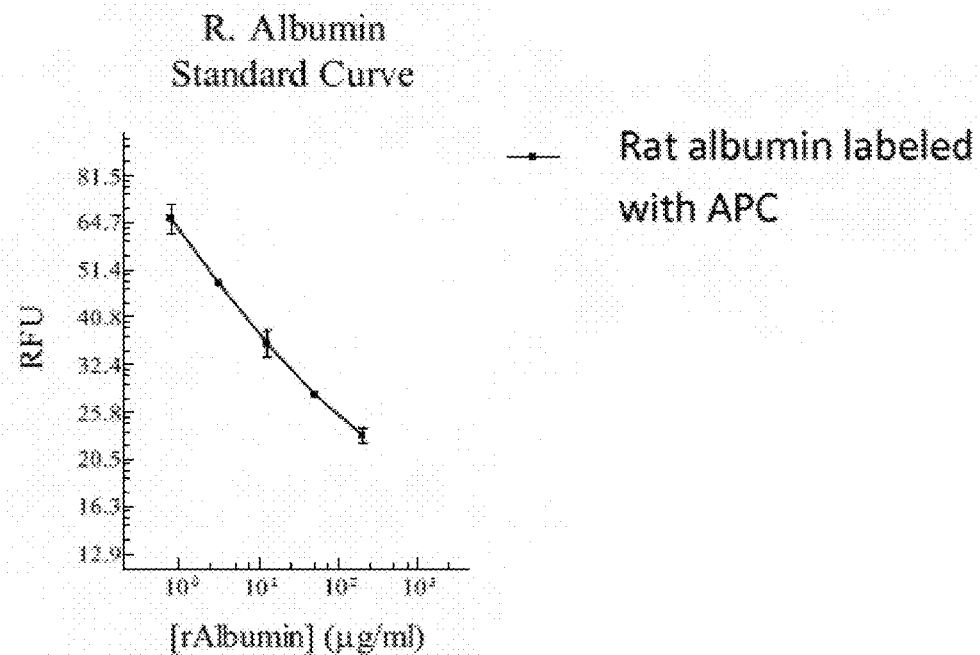
FIG. 17 is a standard curve generated from data obtained using the disclosed assay technique performed using a rat albumin over-labeled with APC, evaluated by reading with the Molecular Devices Gemini XPS microplate reader.
Figure 18:
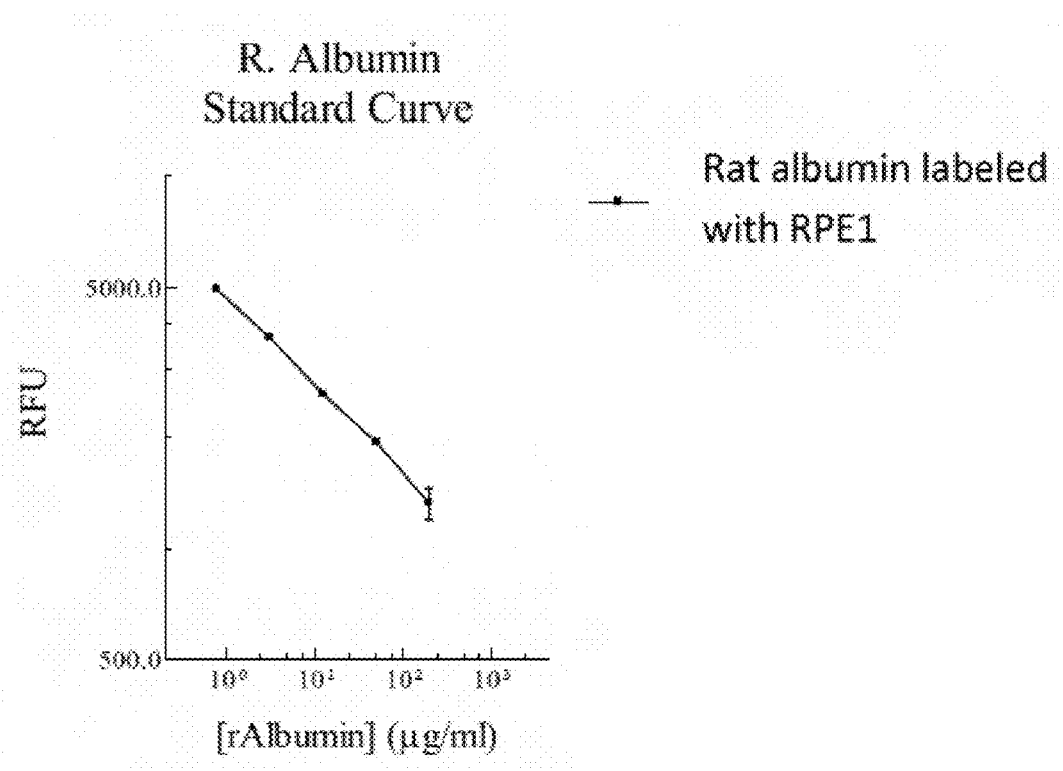
FIG. 18 is a standard curve generated from data obtained using the disclosed assay technique using a rat albumin over-labeled with RPE1, evaluated by reading with the BioTek FLx800 microplate reader.
Figure 19:
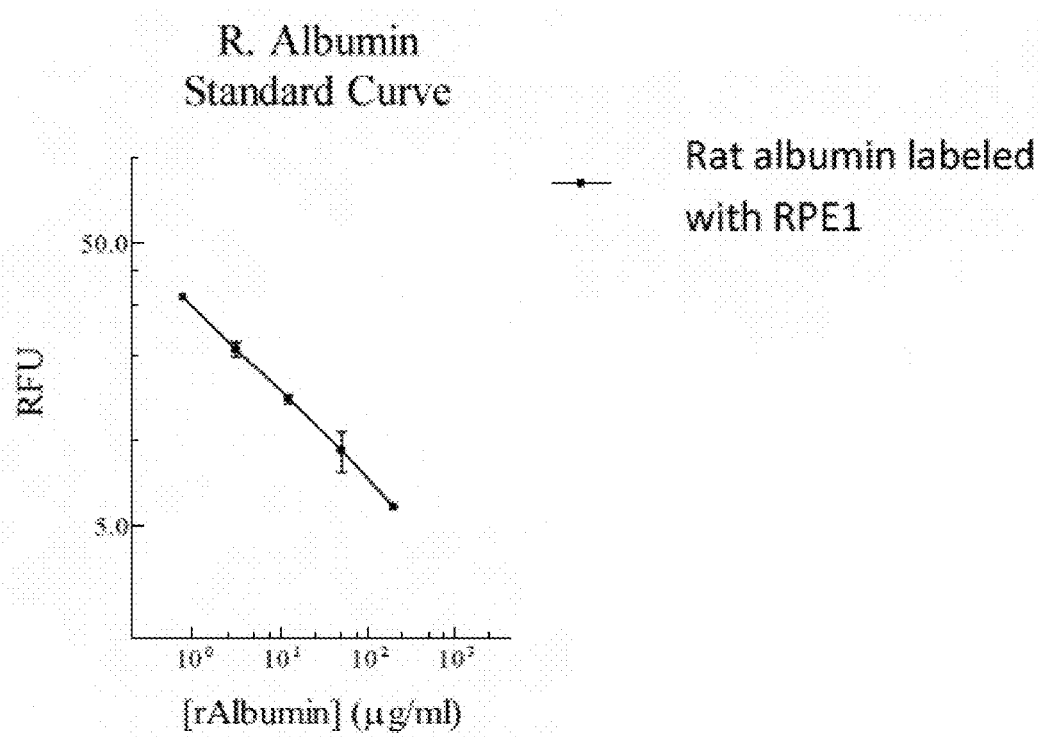
FIG. 19 is a standard curve generated from data obtained using the disclosed assay technique performed using a rat albumin over-labeled with RPE1, evaluated by reading with the Molecular Devices Gemini XPS microplate reader.

Rat albumin ELISA system performance using competitive immunoassay techniques and reading with Molecular Devices SpectraMax 340PC microplate reader has been evaluated (FIG. 15). Rat albumin new assay system using APC or RPE1 labeled protein as the tracer to perform competitive immunoassay and read with BioTek FLx800 microplate reader (FIGS. 16, 18) and Molecular Devices Gemini XPS microplate reader (FIGS. 17, 19).

The data demonstrates that the performance of the new system in rat albumin determination is similar to that of the ELISA kit. The performance characterization is summarized in Table 4.

TABLE 4

| | ELISA performance vs. new assay system in the competitive immunoassay system to determine Rat Albumin | | | | |
|---|---|---|---|---|---|
| | ELISA System | APC/Gemini XPS | APC/ FLx800 | RPE1/Gemini XPS | RPE1/ FLx800 |
| Standard Range | 200-0.391 µg/ml | 200-0.781 µg/ml | 200-0.781 µg/ml | 200-0.781 µg/ml | 200-0.781 µg/ml |
| Intra-assay CV | 7.7 | 5.1 | 5.8 | 6.3 | 6.1 |
| Inter-assay CV | 15.2 | 18.1 | 11.4 | 12.4 | 10.3 |
| Sample value | 41582.8 µg/ml | 42853.7 µg/ml | 41436.5 µg/ml | 38982.0 µg/ml | 39521.6 µg/ml |
| Sensitivity | 0.391 µg/ml | 0.781 µg/ml | 0.781 µg/ml | 0.781 µg/ml | 0.781 µg/ml |

Rat Albumin assays were used to demonstrate the performance similarity of ELISA and the new immunoassays described herein.

The new Human and Rat Albumin assays described herein have demonstrated similar performance to the ELISA system.

Example 7: Human and Rat Albumin Multiplex

Figure 20:
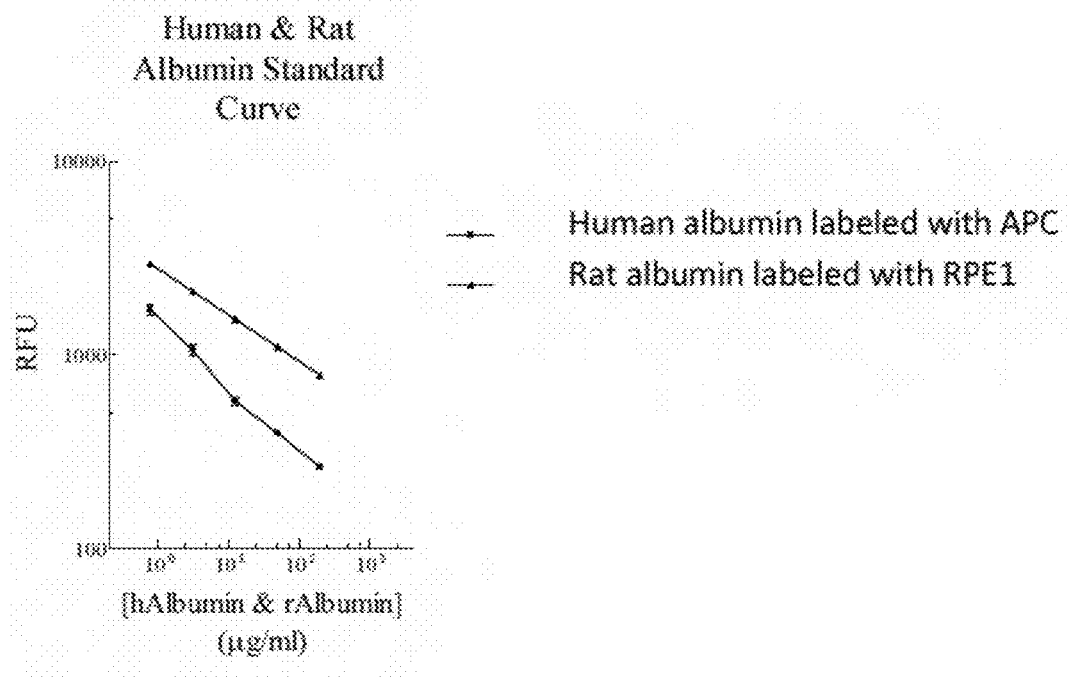
FIG. 20 is a standard curve generated using human albumin over-labeled with APC and rat Albumin over-labeled with RPE1 read using the BioTek FLx800 microplate reader.
Figure 21:
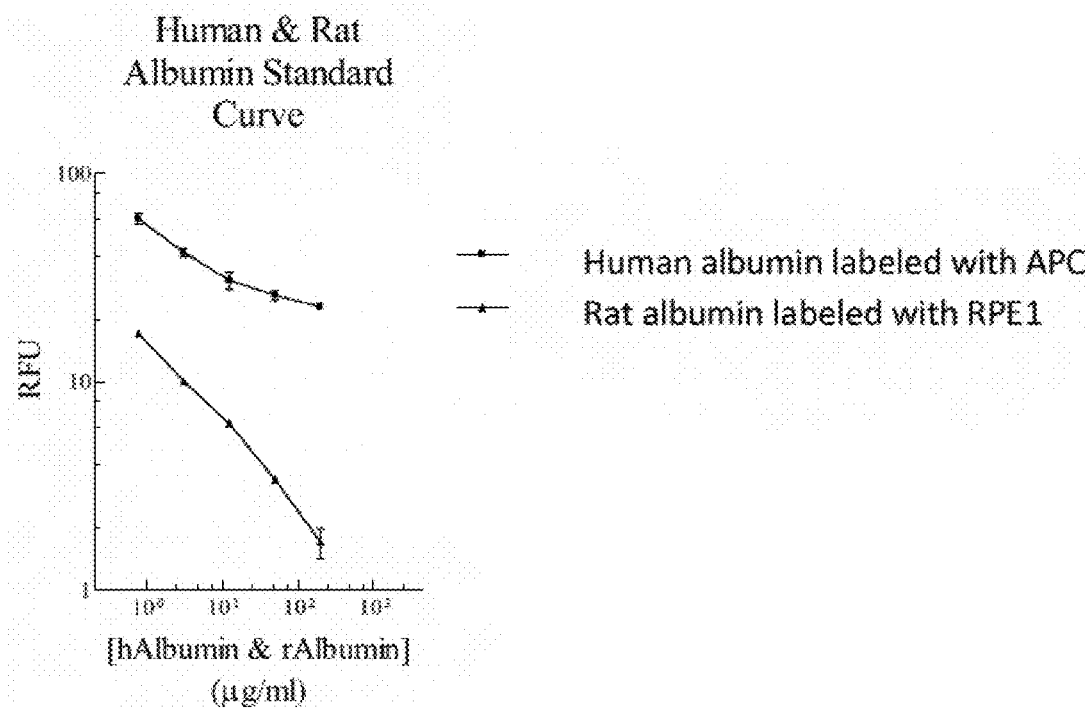
FIG. 21 is a standard curve generated using human albumin over-labeled with APC and rat Albumin I over-labeled with RPE1 read using the Molecular Devices Gemini XPS reader.
Figure 22:
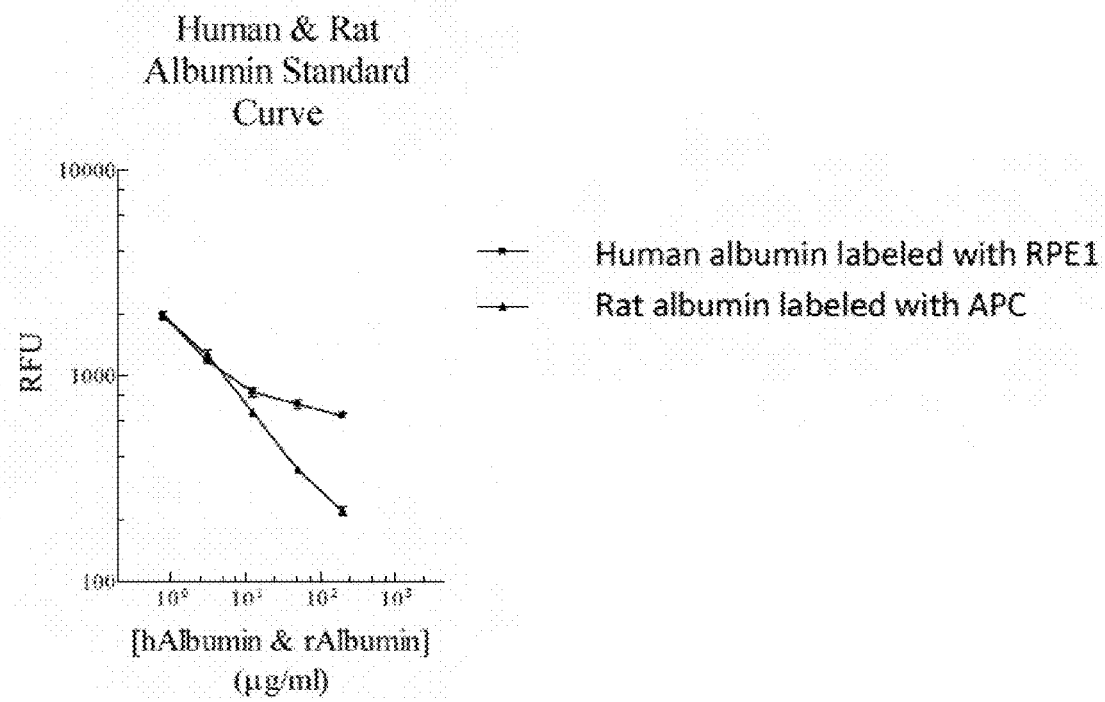
FIG. 22 is a standard curve generated using human Albumin over-labeled with RPE1 and Rat Albumin over-labeled with APC using the BioTek FLx800 microplate reader.
Figure 23:
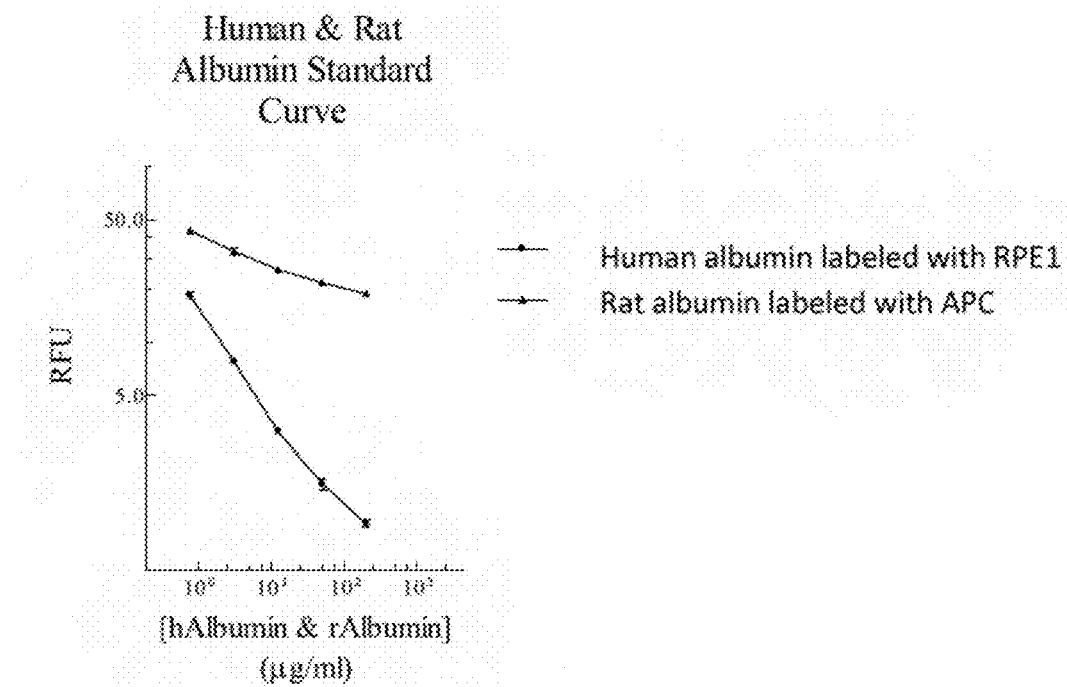
FIG. 23 is a standard curve generated using human Albumin over-labeled with RPE1 and Rat Albumin over-labeled with APC using the Molecular Devices Gemini XPS reader.

Next, the performance similarities between the ELISA and the new multiplex assays of human and rat albumin were investigated, using different fluorescent proteins. RPE1 and APC labeled human albumin multiplexed with APC and RPE1 labeled rat albumin have been tested, and results are as follows.
1. Human albumin labeled with APC and rat Albumin labeled with RPE1 read using BioTek FLx800 microplate reader (FIG. 20) and Molecular Devices Gemini XPS reader (FIG. 21).
2. Human Albumin labeled with RPE1 and Rat Albumin labeled with APC BioTek FLx800 microplate reader (FIG. 22) and Molecular Devices Gemini XPS reader (FIG. 23).

The performance of the human and rat albumin multiplex assays versus that of the ELISA is summarized below.

TABLE 5a

ELISA performance vs. new assay system in the competitive immunoassay system to determine human albumin

|  | ELISA | Human Albumin APC labeled multiplex (Gemini XPS) | Human Albumin APC labeled multiplex (FLx800) | Human Albumin RPE1 labeled multiplex (Gemini XPS) | Human Albumin RPE1 labeled multiplex (FLx800) |
|---|---|---|---|---|---|
| Standard Range | 200-3.125 µg/ml | 200-0.781 µg/ml | 200-0.781 µg/ml | 200-0.781 µg/ml | 200-0.781 µg/ml |
| Intra-assay CV | 3.7 | 2.8 | 11.3 | 2.9 | 5.9 |
| Inter-assay CV | 12.2 | 15.7 | 13.0 | 11.5 | 7.3 |
| Sample value | 52069.1 µg/ml | 55401.6 µg/ml | 53386.9 µg/ml | 54628.1 µg/ml | 53853.9 µg/ml |
| Sensitivity | 3.125 µg/ml | 0.781 µg/ml | 0.781 µg/ml | 0.781 µg/ml | 0.781 µg/ml |

TABLE 5b

ELISA performance vs. new assay system in the competitive immunoassay system to determine rat albumin

|  | ELISA | Rat Albumin APC labeled multiplex (Gemini XPS) | Rat Albumin APC labeled multiplex (FLx800) | Rat Albumin RPE1 labeled multiplex (Gemini XPS) | Rat Albumin RPE1 labeled multiplex (FLx800) |
|---|---|---|---|---|---|
| Standard Range | 200-0.391 µg/ml | 200-0.781 µg/ml | 200-0.781 µg/ml | 200-0.781 µg/ml | 200-0.781 µg/ml |
| Intra-assay CV | 7.7 | 2.7 | 8.6 | 6.1 | 8.8 |
| Inter-assay CV | 15.2 | 14.7 | 15.5 | 6.4 | 8.3 |
| Sample value | 41582.8 µg/ml | 39224.7 µg/ml | 36339.0 µg/ml | 18372.4 µg/ml | 14875.0 µg/ml |
| Sensitivity | 0.391 µg/ml | 0.781 µg/ml | 0.781 µg/ml | 0.781 µg/ml | 0.781 µg/ml |

Example 8: Sandwich Immunoassay Series

We have developed two sandwich immunoassays using two different dyes (Atto 590 & Pierce DyLight 488) and two different fluorescent proteins (APC & RPE1) to label antibodies to be used as secondary antibodies to report signals.
Human Complement C5 Assays:
  Materials:
    Human C5 (Complement Technology, Inc. Cat#A120)
    Human Complement C5 Polyclonal Antibody (in house rabbit antibody raised against purified protein from human plasma purchased from The Binding Site Group Ltd, UK)
    DyLight 488 NHS Ester (Thermo Scientific Cat #46402)
    ATTO 590 EX594/EM624 (ATTO-TEC GmbH Cat # AD 590-35
    R-Phycocyanins I (R-PE1) (Phyco-Biotech Cat #RPE1)
    Allophycocyanin (APC) (Phyco-Biotech Cat #APC)
  Buffers:
    PBS—NaCl 137 mM, KCl 2.7 mM, Na2HPO4.2H2O 10 mM, KH2PO4 2.0 mM, pH 7.4
    FAB—PBS with 0.02% BSA and 0.02% Sodium Azide
    Wash—PBS with 0.1% TWEEN®-20 and 0.02% Sodium Azide
    SuperBlock Blocking Buffer in PBS (Thermo Scientific Cat#37518
  Current ELISA Protocol:

The microplate is coated with a polyclonal antibody specific for Human Complement C5 at 4 µg/ml. The plate is then blocked with 300 µl of blocking buffer for 4 minutes. The Human Complement C5 protein is prepared in duplicate standard points by serially diluting the standard (1 mg/ml) 1:100000 to produce the first standard point of 10 ng/ml, and then 1:2 with FAB to generate 5, 2.5, 1.25, 0.625, 0.313, and 0.156 ng/ml solutions. FAB serves as the zero standard (0 ng/ml).

A biotinylated polyclonal antibody specific for C5 is diluted 1:50 with FAB.

The Streptavidin-Peroxidase Conjugate is spun down briefly and the desired amount of conjugate is diluted 1:100 with FAB.

A ready-to-use stabilized peroxidase chromogen substrate tetramethylbenzidine (TMB) is used at 1x.

Lastly, 0.5 N hydrochloric acid is used to stop the chromogen substrate reaction.

Human plasma and serum are diluted 1:20000 in FAB, the Common Reference is diluted 1:2000 in FAB, and the Fixed Reference is diluted 1:250 in FAB. The ELISA assay was performed as diagrammed in FIG. 68.

Current DyLight 488 Fluorescent Protocol:

The microplate is coated with a polyclonal antibody specific for Human Complement C5 at a concentration of 7 µg/ml. The plate is then blocked with 300 µl of blocking buffer for 4 minutes. The Human Complement C5 protein is prepared in duplicate standard points by serially diluting the standard (1 mg/ml) 1:100 to produce the first standard point of 10 µg/ml, and then 1:4 with FAB to generate 2.5, 0.625, 0.156, and 0.039 µg/ml solutions. FAB serves as the zero standard (0 µg/ml).

A DyLight 488 fluorescent probe specific for C5 is diluted 1:80 with FAB.

Human plasma and serum are diluted 1:100 in FAB, the Common Reference reconstituted with 1 ml of FAB and further diluted 1:10 in FAB, and the Fixed Reference is reconstituted with 1 ml of FAB and loaded as 1x. The DyLight 488 assay was performed as diagrammed in FIG. 69.

Current ATTO 590 Fluorescent Protocol:

The microplate is coated with a polyclonal antibody specific for Human Complement C5 at a concentration of 7 µg/ml. The plate is then blocked with 300 µl of blocking buffer for 4 minutes. The Human Complement C5 protein is prepared in duplicate standard points by serially diluting the standard (1 mg/ml) 1:100 to produce the first standard point of 10 µg/ml, and then 1:4 with FAB to generate 2.5, 0.625, 0.156, and 0.039 µg/ml solutions. FAB serves as the zero standard (0 µg/ml).

An ATTO 590 fluorescent probe specific for C5 is diluted 1:20 with FAB.

Human plasma and serum are diluted 1:100 in FAB, the Common Reference reconstituted with 1 ml of FAB and further diluted 1:10 in FAB, and the Fixed Reference is reconstituted with 1 ml of FAB and loaded as 1x. The ATTO 590 assay was performed as diagrammed in FIG. 70.

Current APC Fluorescent Protocol:

The microplate is coated with a polyclonal antibody specific for Human Complement C5 at a concentration of 7 µg/ml. The plate is then blocked with 300 µl of blocking buffer for 4 minutes. The Human Complement C5 protein is prepared in duplicate standard points by serially diluting the standard (1 mg/ml) 1:100 to produce the first standard point of 10 µg/ml, and then 1:4 with FAB to generate 2.5, 0.625, 0.156, and 0.039 µg/ml solutions. FAB serves as the zero standard (0 µg/ml).

An APC fluorescent probe specific for C5 is diluted 1:20 with FAB.

Human plasma and serum are diluted 1:100 in FAB, the Common Reference reconstituted with 1 ml of FAB and further diluted 1:10 in FAB, and the Fixed Reference is reconstituted with 1 ml of FAB and loaded as 1x. The APC fluorescent assay was performed as diagrammed in FIG. 71.

Current RPE Fluorescent Protocol:

The microplate is coated with a polyclonal antibody specific for Human Complement C5 at a concentration of 7 µg/ml. The plate is then blocked with 300 µl of blocking buffer for 4 minutes. The Human Complement C5 protein is prepared in duplicate standard points by serially diluting the standard (1 mg/ml) 1:100 to produce the first standard point of 10 µg/ml, and then 1:4 with FAB to generate 2.5, 0.625, 0.156, and 0.039 µg/ml solutions. FAB serves as the zero standard (0 µg/ml).

A RPE fluorescent probe specific for C5 is diluted 1:30 with FAB.

Human plasma and serum are diluted 1:100 in FAB, the Common Reference reconstituted with 1 ml of FAB and further diluted 1:10 in FAB, and the Fixed Reference is reconstituted with 1 ml of FAB and loaded as 1x. The RPE fluorescent assay was performed as diagrammed in FIG. 72.

Current DyLight 488 Multiplex Protocol:

The microplate is coated with two polyclonal antibodies, one specific for Human Complement C5 and another specific for Human Complement C6, each at a concentration of 7 µg/ml. The plate is then blocked with 300 µl of blocking buffer for 4 minutes. The Human Complement C5 protein (1 mg/ml) is diluted 1:50 to generate a stock solution of 20 µg/ml. The Human Complement C5 protein (1 mg/ml) is diluted 1:50 to generate a stock solution of 20 µg/ml. The 20 µg/ml solutions are combined in equal parts to generate a solution that consists of 10 µg/ml of Human Complement C5 and C6. This will act as the standard. A standard curve is prepared in duplicate standard points by serially diluting the standard (10 µg/ml C5/C6) 1:4 with FAB to generate 2.5, 0.625, 0.156, and 0.039 µg/ml solutions. FAB serves as the zero standard (0 µg/ml).

A DyLight 488 fluorescent probe specific for C5 is diluted 1:40 with FAB. An ATTO 590 fluorescent probe specific for C6 is diluted 1:5 with FAB. The diluted fluorescent probe solutions are then combined in equal parts.

Human plasma and serum are diluted 1:100 in FAB, the Common Reference reconstituted with 1 ml of FAB and further diluted 1:10 in FAB, and the Fixed Reference is reconstituted with 1 ml of FAB and loaded as 1x. The DyLight 488 multiplex assay was performed as diagrammed in FIG. 73.

Current ATTO 590 Multiplex Protocol:

The microplate is coated with two polyclonal antibodies, one specific for Human Complement C5 and another specific for Human Complement C6, each at a concentration of 7 µg/ml. The plate is then blocked with 300 µl of blocking buffer for 4 minutes. The Human Complement C5 protein (1 mg/ml) is diluted 1:50 to generate a stock solution of 20 µg/ml. The Human Complement C5 protein (1 mg/ml) is diluted 1:50 to generate a stock solution of 20 µg/ml. The 20 µg/ml solutions are combined in equal parts to generate a solution that consists of 10 µg/ml of Human Complement C5 and C6. This will act as the standard. A standard curve is prepared in duplicate standard points by serially diluting the standard (10 µg/ml C5/C6) 1:4 with FAB to generate 2.5, 0.625, 0.156, and 0.039 µg/ml solutions. FAB serves as the zero standard (0 µg/ml).

A DyLight 488 fluorescent probe specific for C6 is diluted 1:40 with FAB. An ATTO 590 fluorescent probe specific for C5 is diluted 1:10 with FAB. The diluted fluorescent probe solutions are then combined in equal parts.

Human plasma and serum are diluted 1:100 in FAB, the Common Reference reconstituted with 1 ml of FAB and further diluted 1:10 in FAB, and the Fixed Reference is reconstituted with 1 ml of FAB and loaded as 1x. The ATTO 590 multiplex assay was performed as diagrammed in FIG. 74.

Current APC Multiplex Protocol:

The microplate is coated with two polyclonal antibodies, one specific for Human Complement C5 and another specific for Human Complement C6, each at a concentration of 7 µg/ml. The plate is then blocked with 300 µl of blocking buffer for 4 minutes. The Human Complement C5 protein (1 mg/ml) is diluted 1:50 to generate a stock solution of 20 µg/ml. The Human Complement C5 protein (1 mg/ml) is diluted 1:50 to generate a stock solution of 20 µg/ml. The 20 µg/ml solutions are combined in equal parts to generate a solution that consists of 10 µg/ml of Human Complement C5 and C6. This will act as the standard. A standard curve is prepared in duplicate standard points by serially diluting the standard (10 µg/ml C5/C6) 1:4 with FAB to generate 2.5, 0.625, 0.156, and 0.039 µg/ml solutions. FAB serves as the zero standard (0 µg/ml).

A RPE fluorescent probe specific for C6 is diluted 1:10 with FAB. An APC fluorescent probe specific for C5 is diluted 1:5 with FAB. The diluted fluorescent probe solutions are then combined in equal parts.

Human plasma and serum are diluted 1:100 in FAB, the Common Reference reconstituted with 1 ml of FAB and further diluted 1:10 in FAB, and the Fixed Reference is reconstituted with 1 ml of FAB and loaded as 1×. The APC multiplex assay was performed as diagrammed in FIG. 75.

Current RPE Multiplex Protocol:

The microplate is coated with two polyclonal antibodies, one specific for Human Complement C5 and another specific for Human Complement C6, each at a concentration of 7 µg/ml. The plate is then blocked with 300 µl of blocking buffer for 4 minutes. The Human Complement C5 protein (1 mg/ml) is diluted 1:50 to generate a stock solution of 20 µg/ml. The Human Complement C5 protein (1 mg/ml) is diluted 1:50 to generate a stock solution of 20 µg/ml. The 20 µg/ml solutions are combined in equal parts to generate a solution that consists of 10 µg/ml of Human Complement C5 and C6. This will act as the standard. A standard curve is prepared in duplicate standard points by serially diluting the standard (10 µg/ml C5/C6) 1:4 with FAB to generate 2.5, 0.625, 0.156, and 0.039 µg/ml solutions. FAB serves as the zero standard (0 µg/ml).

A RPE fluorescent probe specific for C5 is diluted 1:15 with FAB. An APC fluorescent probe specific for C6 is diluted 1:5 with FAB. The diluted fluorescent probe solutions are then combined in equal parts.

Human plasma and serum are diluted 1:100 in FAB, the Common Reference reconstituted with 1 ml of FAB and further diluted 1:10 in FAB, and the Fixed Reference is reconstituted with 1 ml of FAB and loaded as 1×. The RPE multiplex assay was performed as diagrammed in FIG. 76.

The Human Complement C5 assay was developed to demonstrate that the new assay system performs similarly to the ELISA system.

Figure 24A:
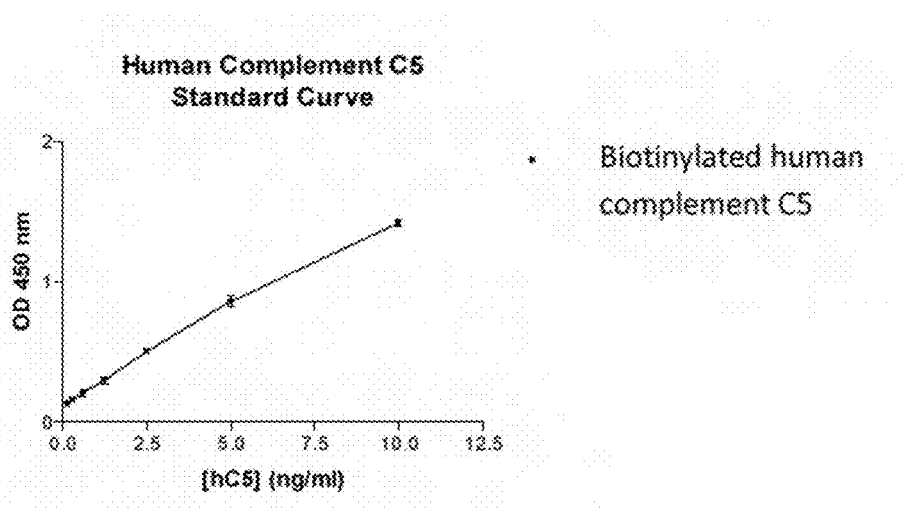
FIG. 24 (*a*) and (*b*) are a standard curve generated from data obtained using a biotinylated human Complement C5 ELISA system using a sandwich immunoassay technique and read using the Molecular Devices SpectraMax 340PC microplate reader.
Figure 24B:
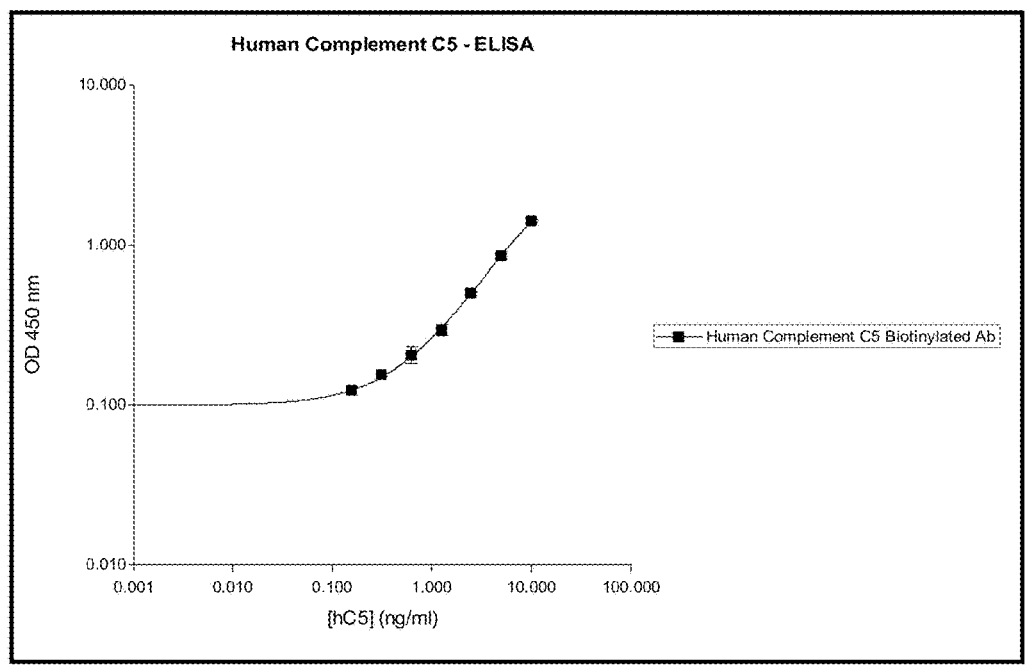
Figure 25A:
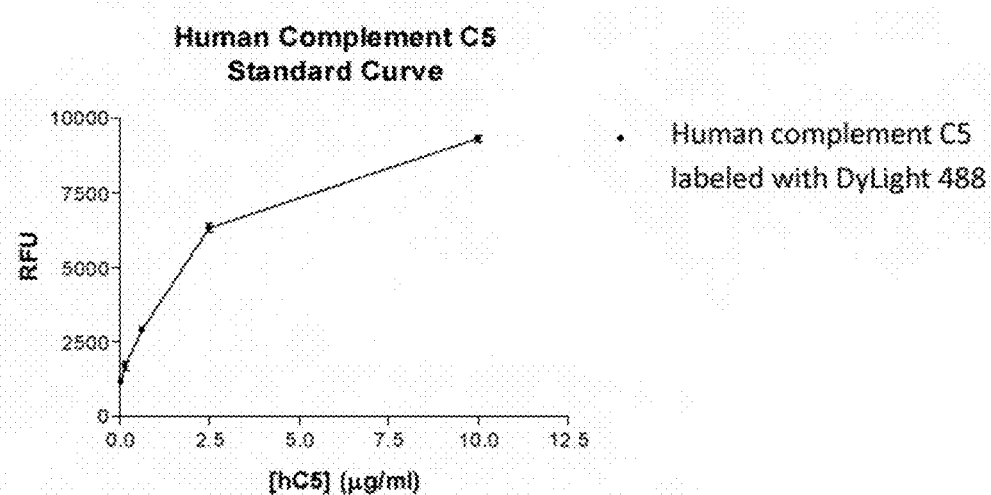
FIG. 25 (*a*) and (*b*) are standard curves generated using the disclosed assay system to perform sandwich immunoassays using Human Complement C5 over-labeled with DyLight 488 using the BioTek FLx800 microplate reader.
Figure 25B:
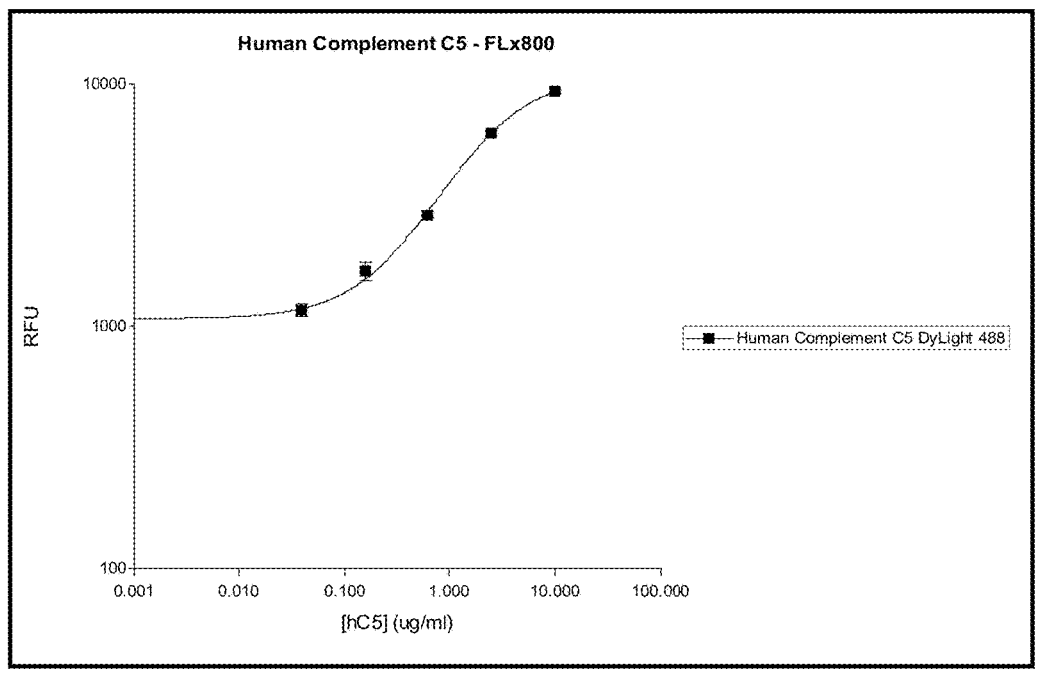
Figure 26A:
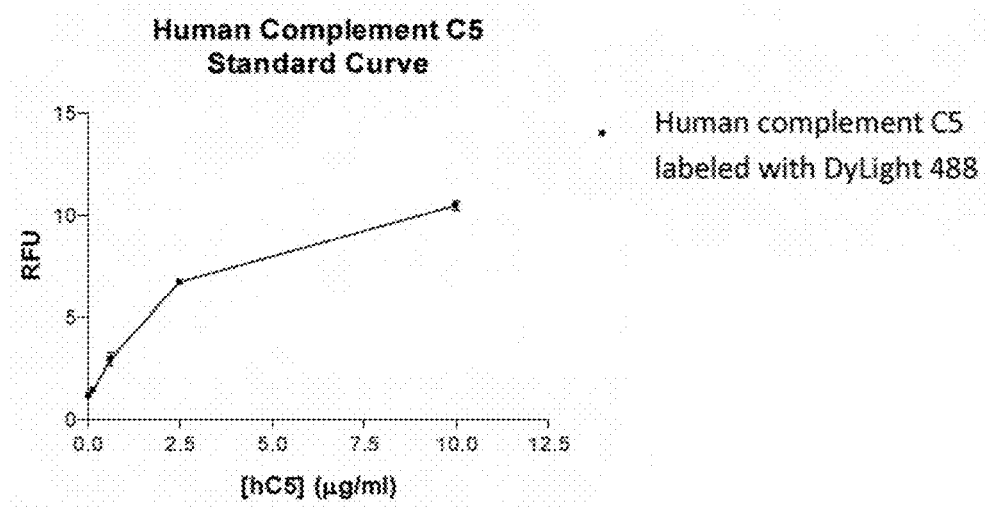
FIG. 26 (*a*) and (*b*) are standard curves generated using the disclosed assay system to perform sandwich immunoassays using Human Complement C5 over-labeled with DyLight 488 using the Molecular Devices Gemini XPS microplate reader.
Figure 26B:
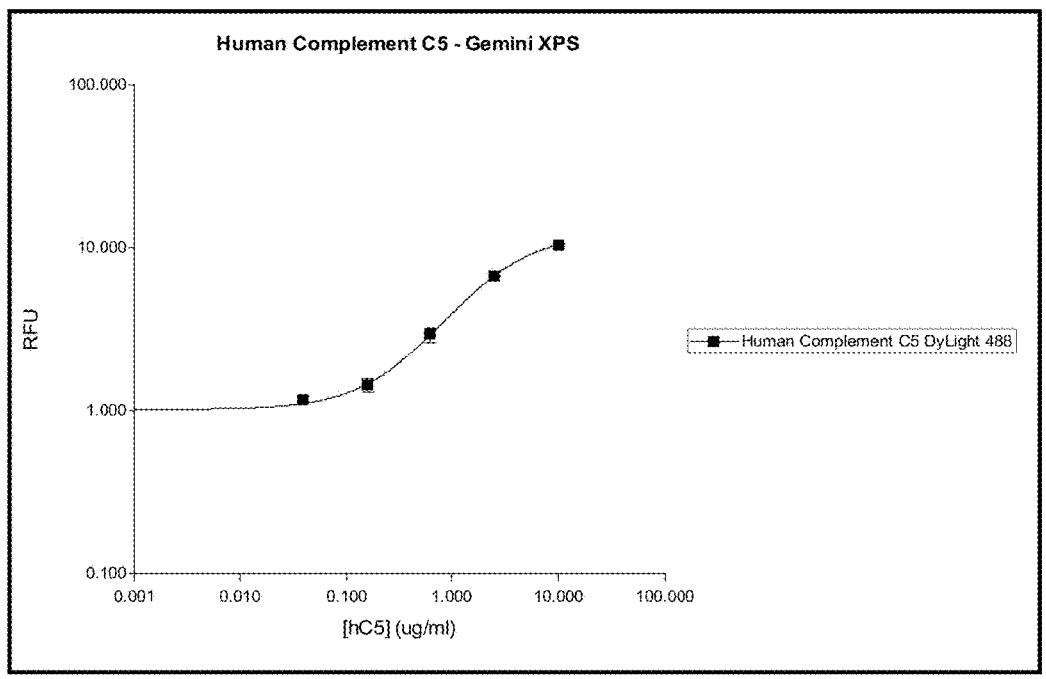
Figure 27A:
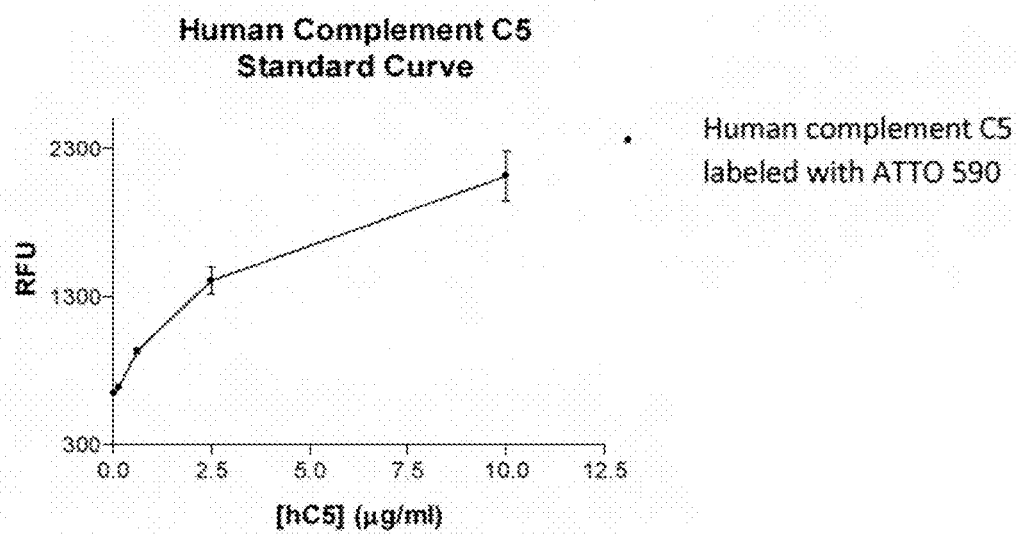
FIG. 27 (*a*) and (*b*) are standard curves generated using the disclosed assay system to perform sandwich immunoassays using Human Complement C5 over-labeled with ATTO 590 using the BioTek FLx800 microplate reader.
Figure 27B:
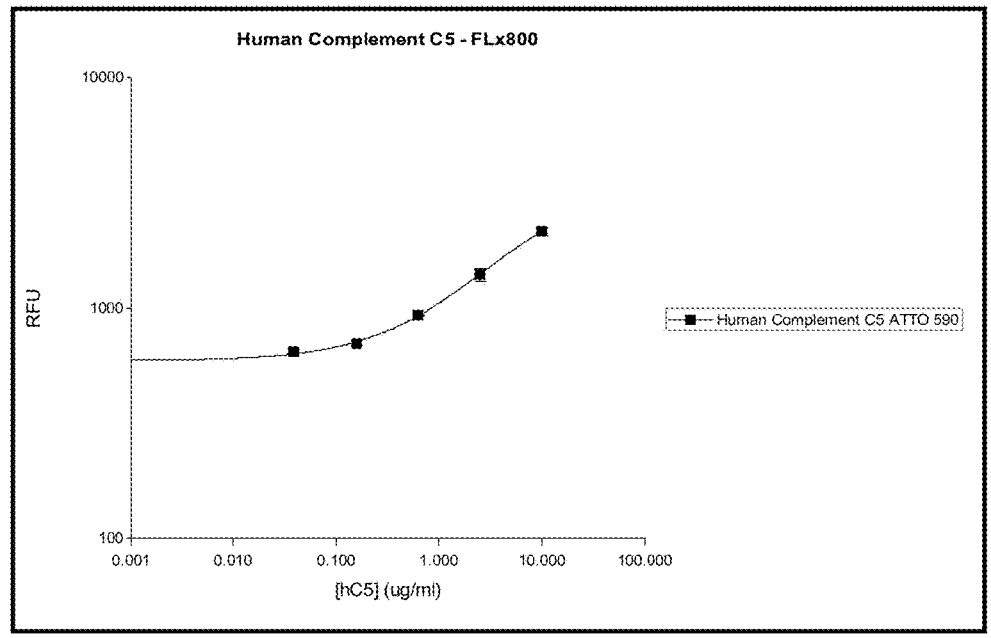
Figure 28A:
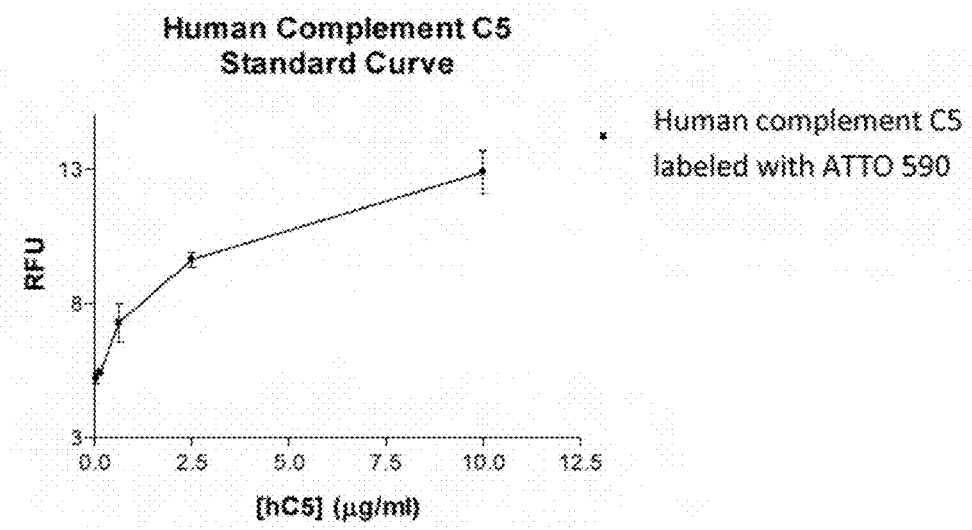
FIG. 28 (*a*) and (*b*) are standard curves generated using the disclosed assay system to perform sandwich immunoassays using Human Complement C5 over-labeled with ATTO 590 using the Molecular Devices Gemini XPS microplate reader.
Figure 28B:
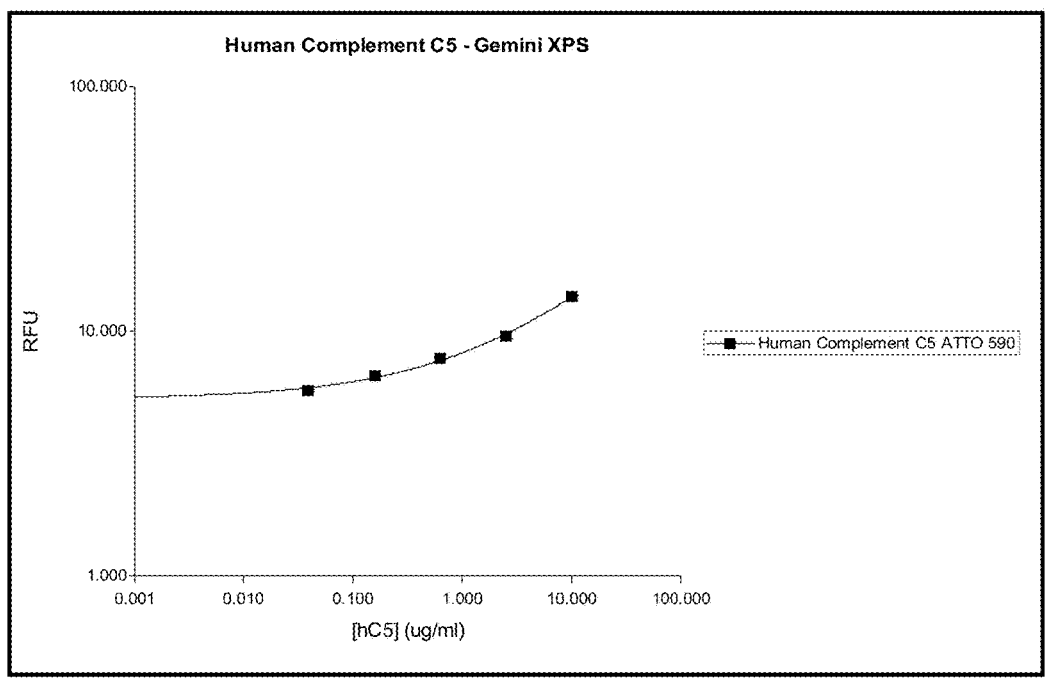
Figure 29A:
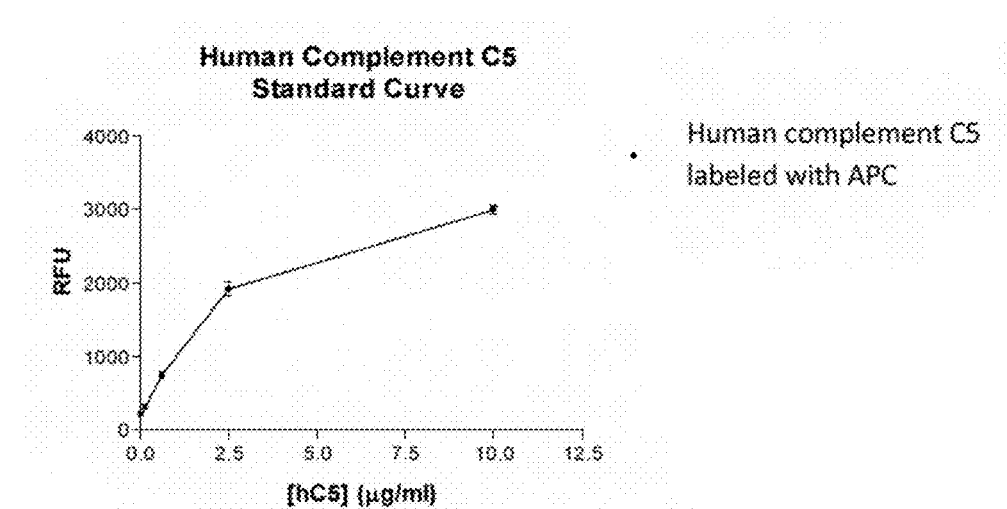
FIG. 29 (*a*) and (*b*) are standard curves generated using the disclosed assay system to perform sandwich immunoassays using Human Complement C5 over-labeled with APC using the BioTek FLx800 microplate reader.
Figure 29B:
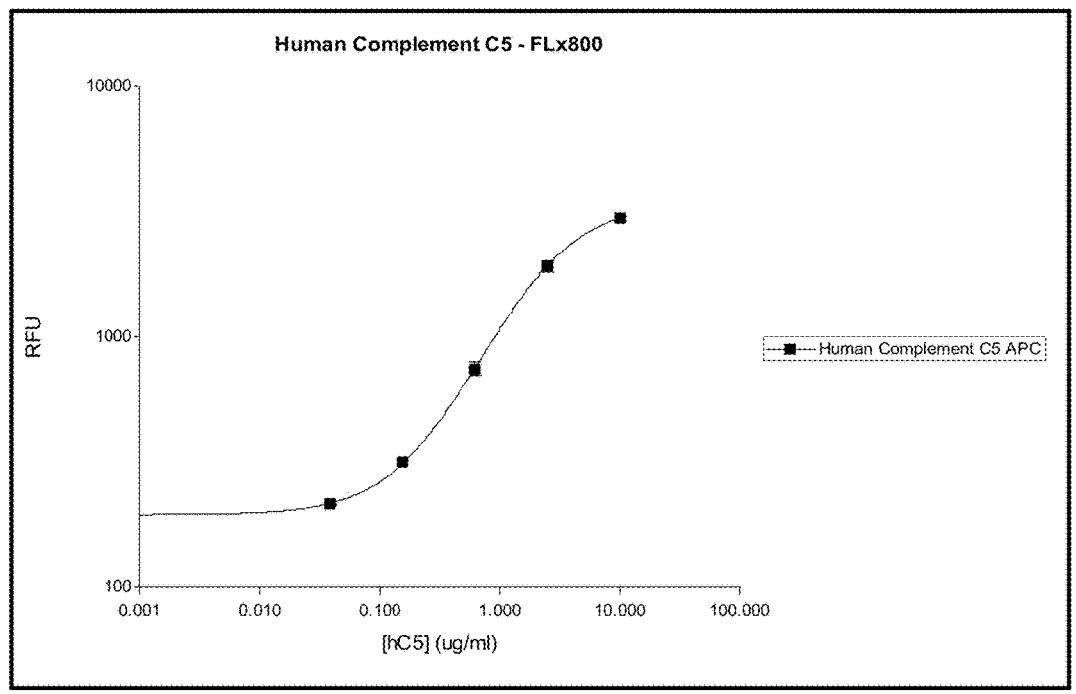
Figure 30A:
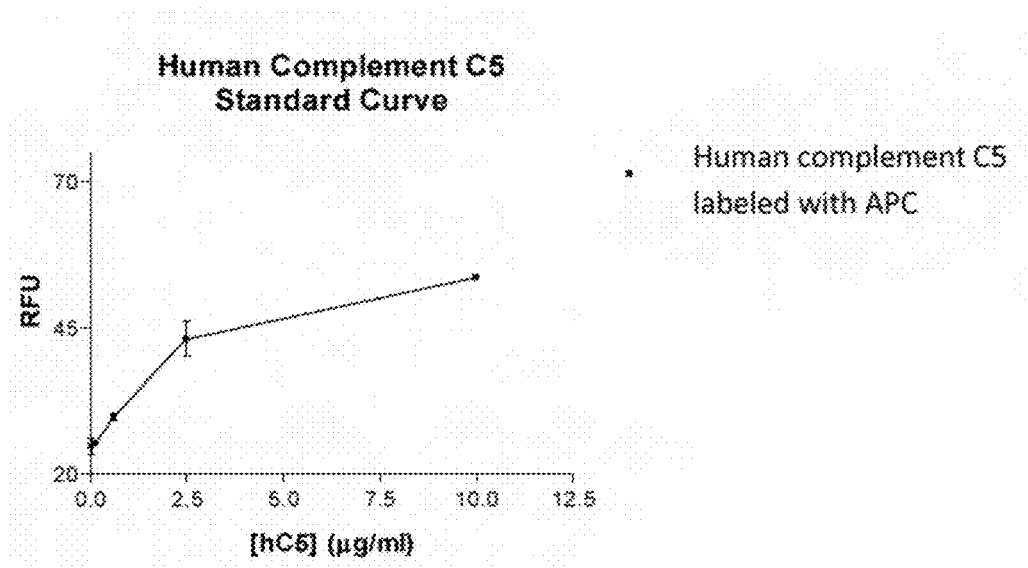
FIG. 30 (*a*) and (*b*) are standard curves generated using the disclosed assay system to perform sandwich immunoassays using Human Complement C5 over-labeled with APC using the Molecular Devices Gemini XPS microplate reader.
Figure 30B:
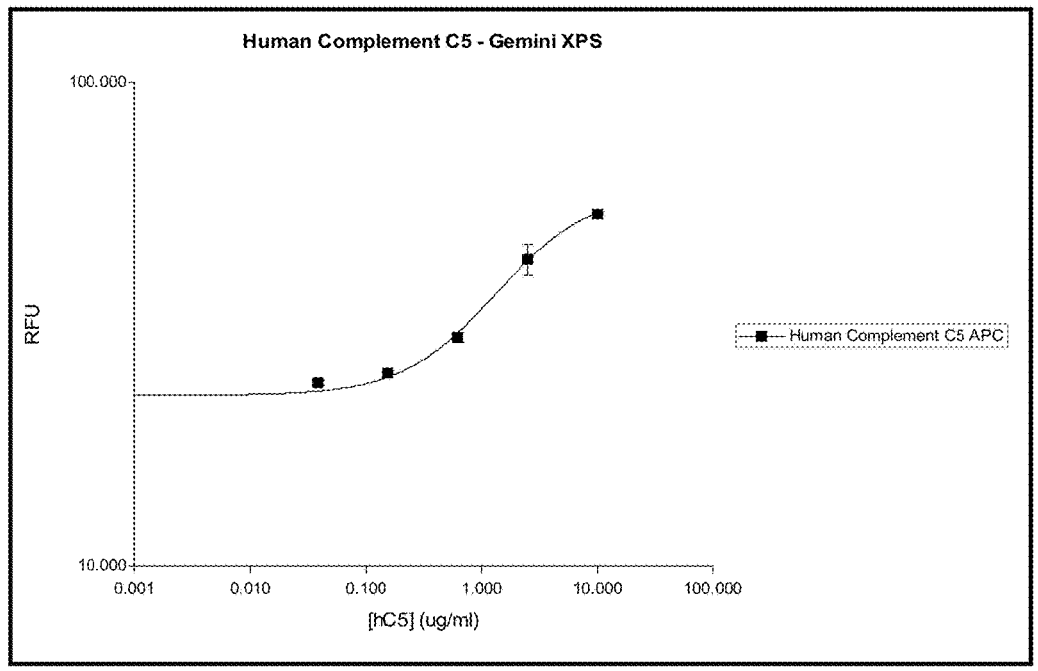
Figure 31A:
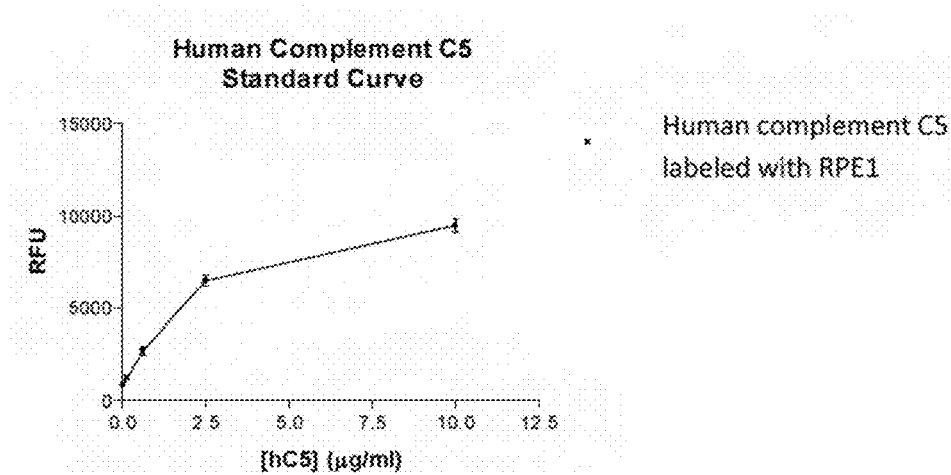
FIG. 31 (*a*) and (*b*) are standard curves generated using the disclosed assay system to perform sandwich immunoassays using Human Complement C5 over-labeled with RPE1 using the BioTek FLx800 microplate reader.
Figure 31B:
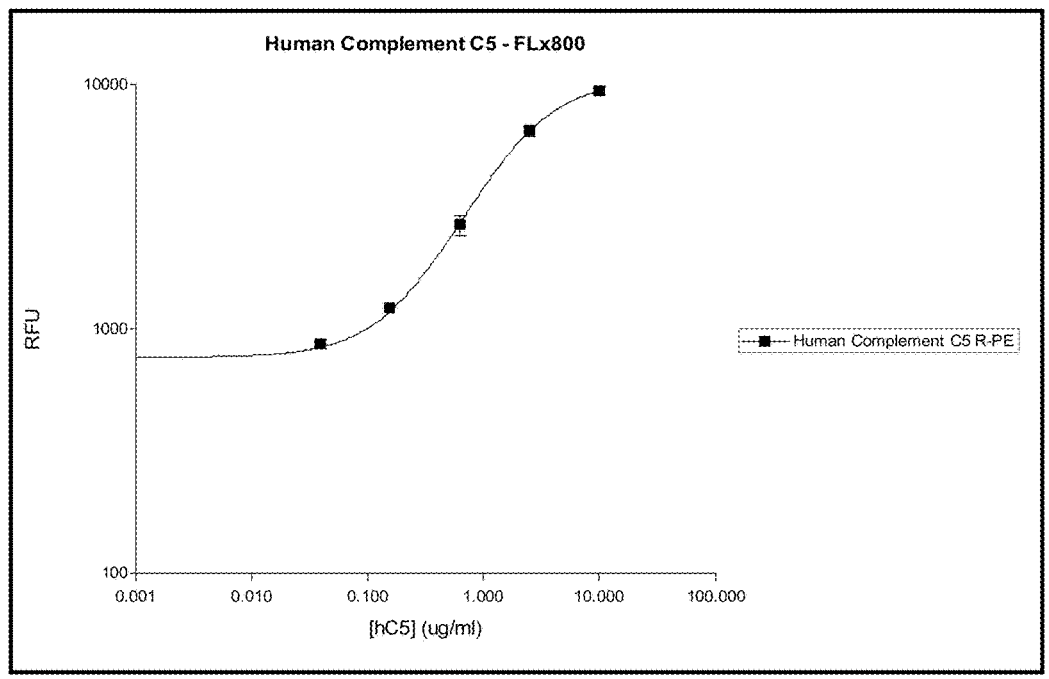
Figure 32A:
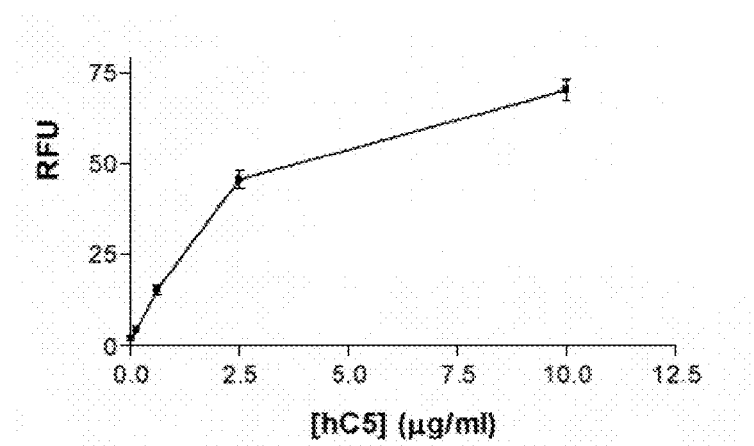
FIG. 32 (*a*) and (*b*) are standard curves generated using the disclosed assay system to perform sandwich immunoassays using Human Complement C5 over-labeled with RPE1 using the Molecular Devices Gemini XPS microplate reader.
Figure 32B:
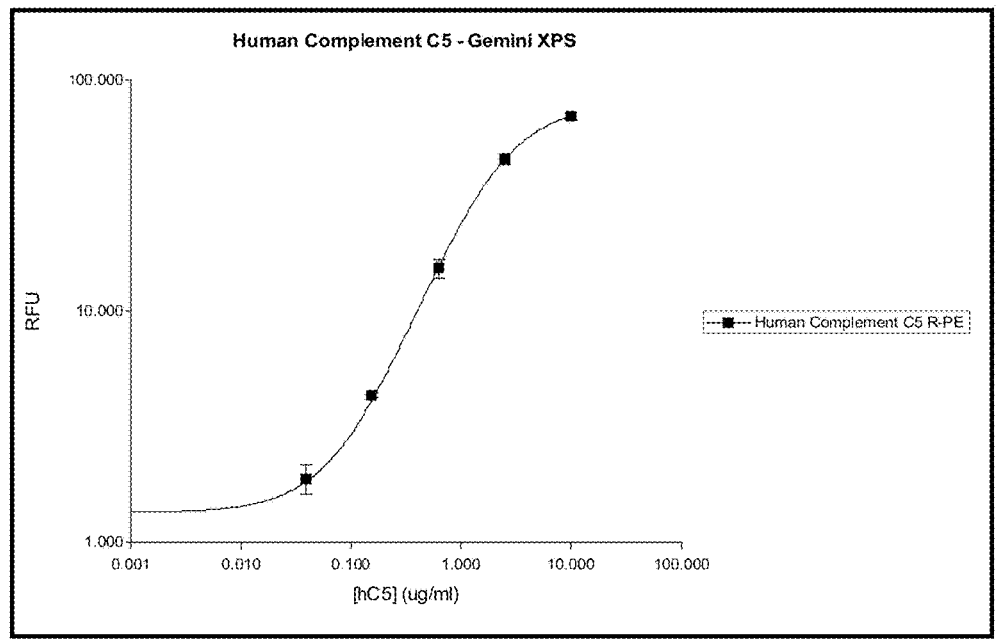

Human Complement C5 ELISA system performance using a sandwich immunoassay technique and read using the Molecular Devices SpectraMax 340PC microplate reader has been evaluated (FIG. 24). Human Complement C5 new assay system using Pierce DyLight 488, ATTO 590, APC and RPE1 labeled detection antibodies to perform sandwich immunoassays and read using the BioTek FLx800 microplate reader (FIG. 25, 27, 29, 31) and Molecular Devices Gemini XPS microplate reader have also been evaluated (FIG. 26, 28, 30, 32).

The data above demonstrates the performance similarities in human complement C5 determination of the new system versus the ELISA system. The ELISA system is more sensitive than the new assay system, but the new system has a wider dynamic range. The performance characterization is summarized in table 6.

TABLE 6

ELISA performance vs. new assay system in the sandwich immunoassay system to determine Human Complement C5

|  | ELISA System | DyLight 488/Gemni XPS | DyLight 488/FLx800 | ATTO 590/Gemni XPS | ATTO 590/FLx800 |
|---|---|---|---|---|---|
| Standard Range | 10-0.156 ng/ml | 10-0.0391 µg/ml | 10-0.0391 µg/ml | 10-0.0391 µg/ml | 10-0.0391 µg/ml |
| Intra-assay CV | 4.4 | 5.2 | 4.8 | 4.5 | 11.9 |
| Inter-assay CV | 7.7 | 10.8 | 6.6 | 14.4 | 10.6 |
| Sample value | 97.8 µg/ml | 114.3 µg/ml | 105.7 µg/ml | 108.5 µg/ml | 101.6 µg/ml |
| Sensitivity | 0.156 ng/ml | 0.0391 µg/ml | 0.0391 µg/ml | 0.0391 µg/ml | 0.0391 µg/ml |
|  | ELISA System | APC/Gemni XPS | APC/FLx800 | RPE1/Gemni XPS | RPE1/FLx800 |
| Standard Range | 10-0.156 ng/ml | 10-0.0391 µg/ml | 10-0.0391 µg/ml | 10-0.0391 µg/ml | 10-0.0391 µg/ml |
| Intra-assay CV | 4.4 | 4.7 | 4.8 | 5.6 | 2.9 |
| Inter-assay CV | 7.7 | 13.2 | 7.6 | 11.2 | 11.3 |
| Sample value | 97.8 µg/ml | 98.1 µg/ml | 108.0 µg/ml | 107.2 µg/ml | 102.6 µg/ml |
| Sensitivity | 0.156 ng/ml | 0.0391 µg/ml | 0.0391 µg/ml | 0.02 µg/ml | 0.0391 µg/ml |

The multiplexing capability of the new Human Complement C6 assay system was characterized against the ELISA system as a single assay.

Human Complement C6 Assays—Materials:
Human C5 (Complement Technology, Inc. Cat#A120)
Human Complement C5 Polyclonal Antibody (in house rabbit antibody raised against purified protein from human plasma purchased from The Binding Site Group Ltd, UK)
DyLight 488 NHS Ester (Thermo Scientific Cat #46402)
ATTO 590 EX594/EM624 (ATTO-TEC GmbH Cat # AD 590-35)
R-Phycocyanins I (R-PE1) (Phyco-Biotech Cat #RPE1)
Allophycocyanin (APC) (Phyco-Biotech Cat #APC)
Buffers:
PBS—NaCl 137 mM, KCl 2.7 mM, Na2HPO4.2H2O 10 mM, KH2PO4 2.0 mM, pH 7.4
FAB—PBS with 0.02% BSA and 0.02% Sodium Azide
Wash—PBS with 0.1% TWEEN®-20 and 0.02% Sodium Azide
SuperBlock Blocking Buffer in PBS (Thermo Scientific Cat#37518)

Current ELISA Protocol:
The microplate is coated with a polyclonal antibody specific for Human Complement C5 at 4 µg/ml. The plate is then blocked with 300 µl of blocking buffer for 4 minutes. The Human Complement C5 protein is prepared in duplicate standard points by serially diluting the standard (1 mg/ml) 1:100000 to produce the first standard point of 10 ng/ml, and then 1:2 with FAB to generate 5, 2.5, 1.25, 0.625, 0.313, and 0.156 ng/ml solutions. FAB serves as the zero standard (0 ng/ml).

A biotinylated polyclonal antibody specific for C5 is diluted 1:50 with FAB.

The Streptavidin-Peroxidase Conjugate is spun down briefly and the desired amount of conjugate is diluted 1:100 with FAB.

A ready-to-use stabilized peroxidase chromogen substrate tetramethylbenzidine (TMB) is used at 1x.

Lastly, 0.5 N hydrochloric acid is used to stop the chromogen substrate reaction.

Human plasma and serum are diluted 1:20000 in FAB, the Common Reference is diluted 1:2000 in FAB, and the Fixed Reference is diluted 1:250 in FAB. The ELISA assay was performed as diagrammed in FIG. 77.

Current DyLight 488 Fluorescent Protocol:
The microplate is coated with a polyclonal antibody specific for Human Complement C6 at a concentration of 7 µg/ml. The plate is then blocked with 300 µl of blocking buffer for 4 minutes. The Human Complement C6 protein is prepared in duplicate standard points by serially diluting the standard (1 mg/ml) 1:100 to produce the first standard point of 10 µg/ml, and then 1:4 with FAB to generate 2.5, 0.625, 0.156, and 0.039 µg/ml solutions. FAB serves as the zero standard (0 µg/ml).

A DyLight 488 fluorescent probe specific for C6 is diluted 1:100 with FAB.

Human plasma and serum are diluted 1:100 in FAB, the Common Reference reconstituted with 1 ml of FAB and further diluted 1:10 in FAB, and the Fixed Reference is reconstituted with 1 ml of FAB and loaded as 1x. The DyLight 488 fluorescent assay was performed as diagrammed in FIG. 78.

Current ATTO 590 Fluorescent Protocol:
The microplate is coated with a polyclonal antibody specific for Human Complement C6 at a concentration of 7 µg/ml. The plate is then blocked with 300 µl of blocking buffer for 4 minutes. The Human Complement C6 protein is prepared in duplicate standard points by serially diluting the standard (1 mg/ml) 1:100 to produce the first standard point of 10 µg/ml, and then 1:4 with FAB to generate 2.5, 0.625, 0.156, and 0.039 µg/ml solutions. FAB serves as the zero standard (0 µg/ml).

An ATTO 590 fluorescent probe specific for C6 is diluted 1:10 with FAB.

Human plasma and serum are diluted 1:100 in FAB, the Common Reference reconstituted with 1 ml of FAB and further diluted 1:10 in FAB, and the Fixed Reference is reconstituted with 1 ml of FAB and loaded as 1x. The ATTO 590 fluorescent assay was performed as diagrammed in FIG. 79.

Current APC Fluorescent Protocol:
The microplate is coated with a polyclonal antibody specific for Human Complement C6 at a concentration of 7 µg/ml. The plate is then blocked with 300 µl of blocking buffer for 4 minutes. The Human Complement C6 protein is prepared in duplicate standard points by serially diluting the standard (1 mg/ml) 1:100 to produce the first standard point of 10 µg/ml, and then 1:4 with FAB to generate 2.5, 0.625, 0.156, and 0.039 µg/ml solutions. FAB serves as the zero standard (0 µg/ml).

An APC fluorescent probe specific for C6 is diluted 1:10 with FAB.

Human plasma and serum are diluted 1:100 in FAB, the Common Reference reconstituted with 1 ml of FAB and further diluted 1:10 in FAB, and the Fixed Reference is reconstituted with 1 ml of FAB and loaded as 1x. The APC fluorescent assay was performed as diagrammed in FIG. 80.

Current RPE Fluorescent Protocol:
The microplate is coated with a polyclonal antibody specific for Human Complement C5 at a concentration of 7 µg/ml. The plate is then blocked with 300 µl of blocking buffer for 4 minutes. The Human Complement C5 protein is prepared in duplicate standard points by serially diluting the standard (1 mg/ml) 1:100 to produce the first standard point of 10 µg/ml, and then 1:4 with FAB to generate 2.5, 0.625, 0.156, and 0.039 µg/ml solutions. FAB serves as the zero standard (0 µg/ml).

A RPE fluorescent probe specific for C5 is diluted 1:30 with FAB.

Human plasma and serum are diluted 1:100 in FAB, the Common Reference reconstituted with 1 ml of FAB and further diluted 1:10 in FAB, and the Fixed Reference is reconstituted with 1 ml of FAB and loaded as 1x. The RPE fluorescent assay was performed as diagrammed in FIG. 81.

Current ATTO 590 Multiplex Protocol:
The microplate is coated with two polyclonal antibodies, one specific for Human Complement C5 and another specific for Human Complement C6, each at a concentration of 7 µg/ml. The plate is then blocked with 300 µl of blocking buffer for 4 minutes. The Human Complement C5 protein (1 mg/ml) is diluted 1:50 to generate a stock solution of 20 µg/ml. The Human Complement C5 protein (1 mg/ml) is diluted 1:50 to generate a stock solution of 20 µg/ml. The 20 µg/ml solutions are combined in equal parts to generate a solution that consists of 10 µg/ml of Human Complement C5 and C6. This will act as the standard. A standard curve is prepared in duplicate standard points by serially diluting the standard (10 µg/ml C5/C6) 1:4 with FAB to generate 2.5, 0.625, 0.156, and 0.039 µg/ml solutions. FAB serves as the zero standard (0 µg/ml).

A DyLight 488 fluorescent probe specific for C5 is diluted 1:40 with FAB. An ATTO 590 fluorescent probe specific for C6 is diluted 1:5 with FAB. The diluted fluorescent probe solutions are then combined in equal parts.

Human plasma and serum are diluted 1:100 in FAB, the Common Reference reconstituted with 1 ml of FAB and further diluted 1:10 in FAB, and the Fixed Reference is reconstituted with 1 ml of FAB and loaded as 1×. The ATTO 590 multiplex assay was performed as diagrammed in FIG. 82.

Current DyLight 488 Multiplex Protocol:

The microplate is coated with two polyclonal antibodies, one specific for Human Complement C5 and another specific for Human Complement C6, each at a concentration of 7 μg/ml. The plate is then blocked with 300 μl of blocking buffer for 4 minutes. The Human Complement C5 protein (1 mg/ml) is diluted 1:50 to generate a stock solution of 20 μg/ml. The Human Complement C5 protein (1 mg/ml) is diluted 1:50 to generate a stock solution of 20 μg/ml. The 20 μg/ml solutions are combined in equal parts to generate a solution that consists of 10 μg/ml of Human Complement C5 and C6. This will act as the standard. A standard curve is prepared in duplicate standard points by serially diluting the standard (10 μg/ml C5/C6) 1:4 with FAB to generate 2.5, 0.625, 0.156, and 0.039 μg/ml solutions. FAB serves as the zero standard (0 μg/ml).

A DyLight 488 fluorescent probe specific for C6 is diluted 1:40 with FAB. An ATTO 590 fluorescent probe specific for C5 is diluted 1:10 with FAB. The diluted fluorescent probe solutions are then combined in equal parts.

Human plasma and serum are diluted 1:100 in FAB, the Common Reference reconstituted with 1 ml of FAB and further diluted 1:10 in FAB, and the Fixed Reference is reconstituted with 1 ml of FAB and loaded as 1×. The DyLight 488 multiplex assay was performed as diagrammed in FIG. 83.

Current RPE Multiplex Protocol:

The microplate is coated with two polyclonal antibodies, one specific for Human Complement C5 and another specific for Human Complement C6, each at a concentration of 7 μg/ml. The plate is then blocked with 300 μl of blocking buffer for 4 minutes. The Human Complement C5 protein (1 mg/ml) is diluted 1:50 to generate a stock solution of 20 μg/ml. The Human Complement C5 protein (1 mg/ml) is diluted 1:50 to generate a stock solution of 20 μg/ml. The 20 μg/ml solutions are combined in equal parts to generate a solution that consists of 10 μg/ml of Human Complement C5 and C6. This will act as the standard. A standard curve is prepared in duplicate standard points by serially diluting the standard (10 μg/ml C5/C6) 1:4 with FAB to generate 2.5, 0.625, 0.156, and 0.039 μg/ml solutions. FAB serves as the zero standard (0 μg/ml).

A RPE fluorescent probe specific for C6 is diluted 1:10 with FAB. An APC fluorescent probe specific for C5 is diluted 1:5 with FAB. The diluted fluorescent probe solutions are then combined in equal parts.

Human plasma and serum are diluted 1:100 in FAB, the Common Reference reconstituted with 1 ml of FAB and further diluted 1:10 in FAB, and the Fixed Reference is reconstituted with 1 ml of FAB and loaded as 1×. The RPE multiplex assay was performed as diagrammed in FIG. 84.

Current APC Multiplex Protocol:

The microplate is coated with two polyclonal antibodies, one specific for Human Complement C5 and another specific for Human Complement C6, each at a concentration of 7 μg/ml. The plate is then blocked with 300 μl of blocking buffer for 4 minutes. The Human Complement C5 protein (1 mg/ml) is diluted 1:50 to generate a stock solution of 20 μg/ml. The Human Complement C5 protein (1 mg/ml) is diluted 1:50 to generate a stock solution of 20 μg/ml. The 20 μg/ml solutions are combined in equal parts to generate a solution that consists of 10 μg/ml of Human Complement C5 and C6. This will act as the standard. A standard curve is prepared in duplicate standard points by serially diluting the standard (10 μg/ml C5/C6) 1:4 with FAB to generate 2.5, 0.625, 0.156, and 0.039 μg/ml solutions. FAB serves as the zero standard (0 μg/ml).

A RPE fluorescent probe specific for C5 is diluted 1:15 with FAB. An APC fluorescent probe specific for C6 is diluted 1:5 with FAB. The diluted fluorescent probe solutions are then combined in equal parts.

Human plasma and serum are diluted 1:100 in FAB, the Common Reference reconstituted with 1 ml of FAB and further diluted 1:10 in FAB, and the Fixed Reference is reconstituted with 1 ml of FAB and loaded as 1×. The APC multiplex assay was performed as diagrammed in FIG. 85.

Figure 33A:
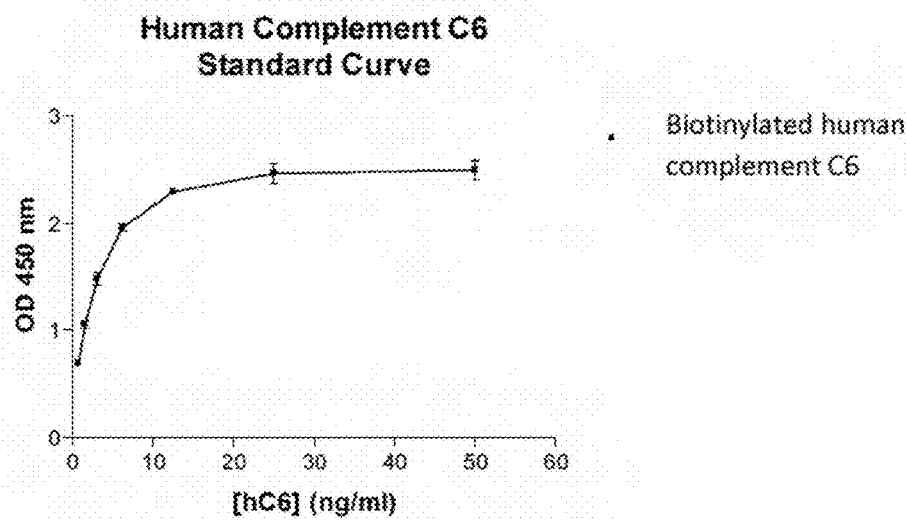
FIG. 33 (a) and (b) are standard curves generated from data obtained using a biotinylated human Complement C6 ELISA system using a sandwich immunoassay technique and read using the Molecular Devices SpectraMax 340PC microplate reader.
Figure 33B:
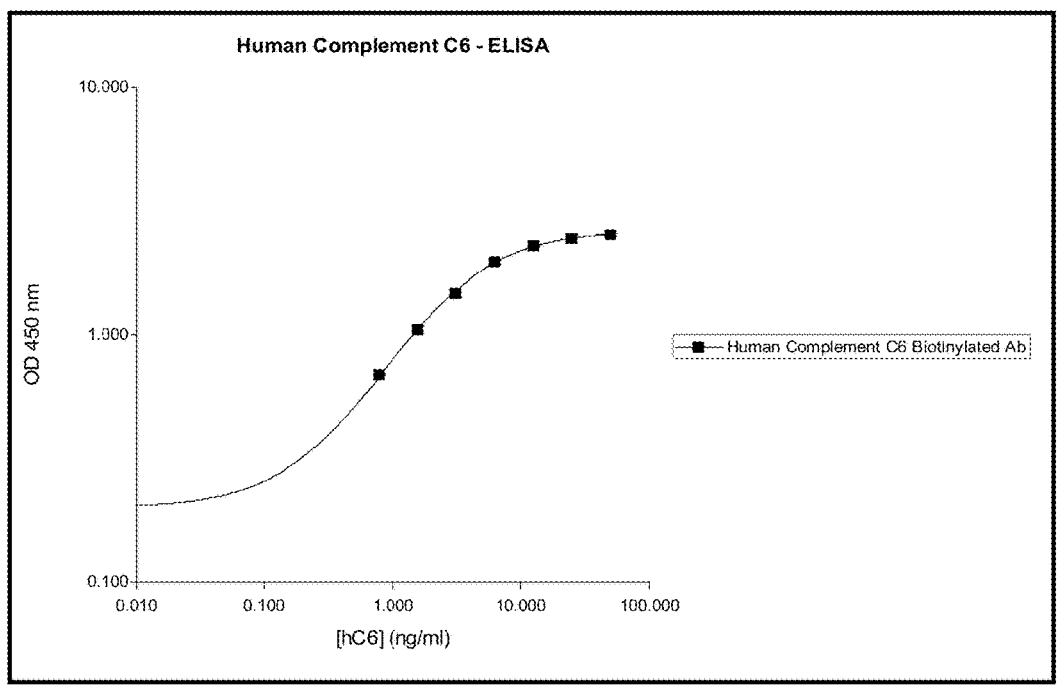
Figure 34A:
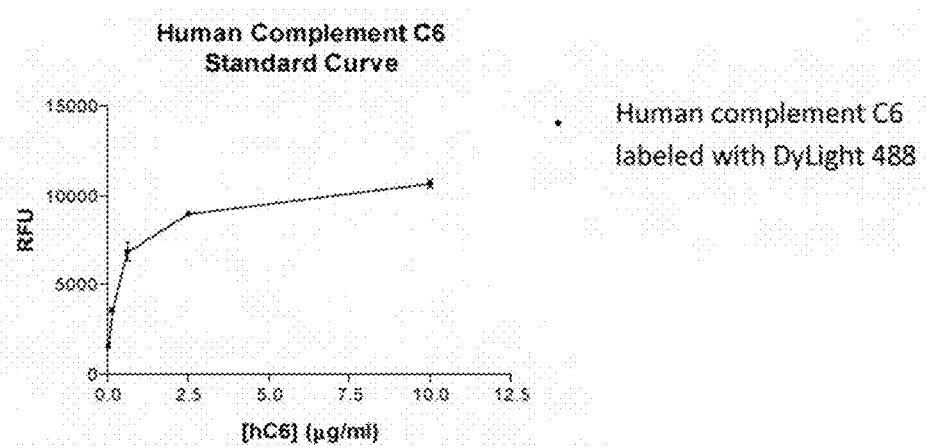
FIG. 34 (a) and (b) are standard curves generated using the disclosed assay system to perform sandwich immunoassays using Human Complement C6 over-labeled with DyLight 488 using the BioTek FLx800 microplate reader.
Figure 34B:
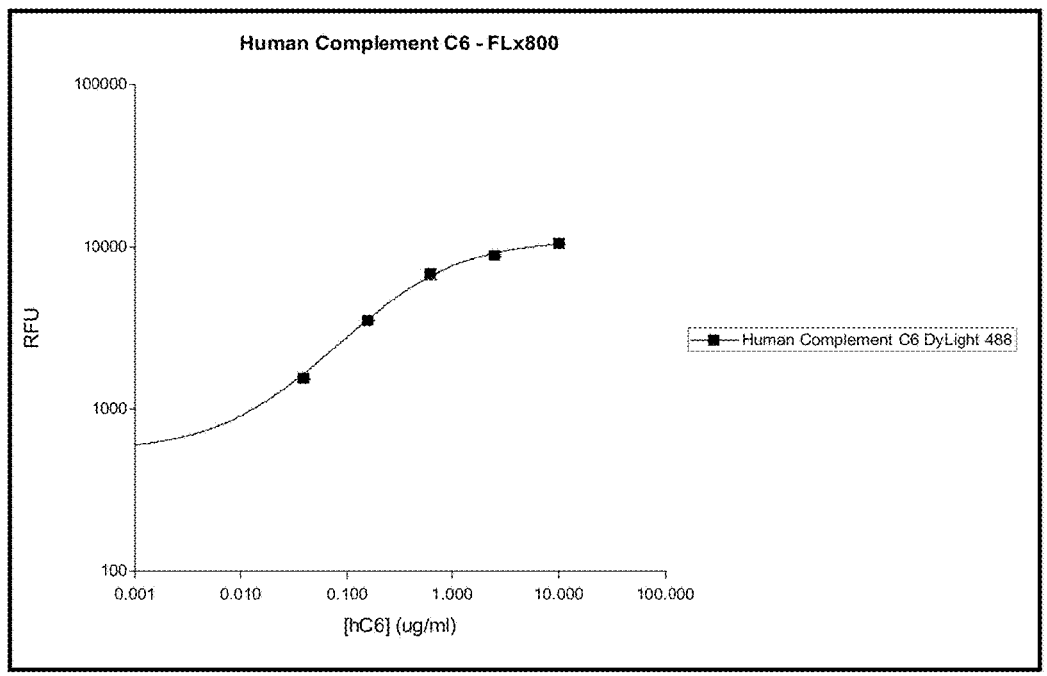
Figure 35A:
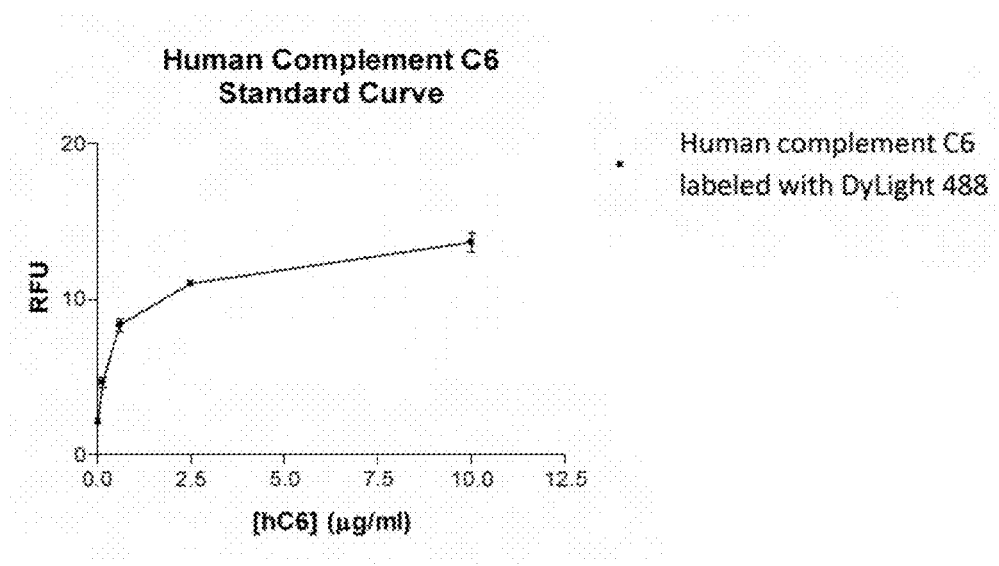
FIG. 35 (a) and (b) are standard curves generated using the disclosed assay system to perform sandwich immunoassays using Human Complement C6 over-labeled with DyLight 488 using the Molecular Devices Gemini XPS microplate reader.
Figure 35B:
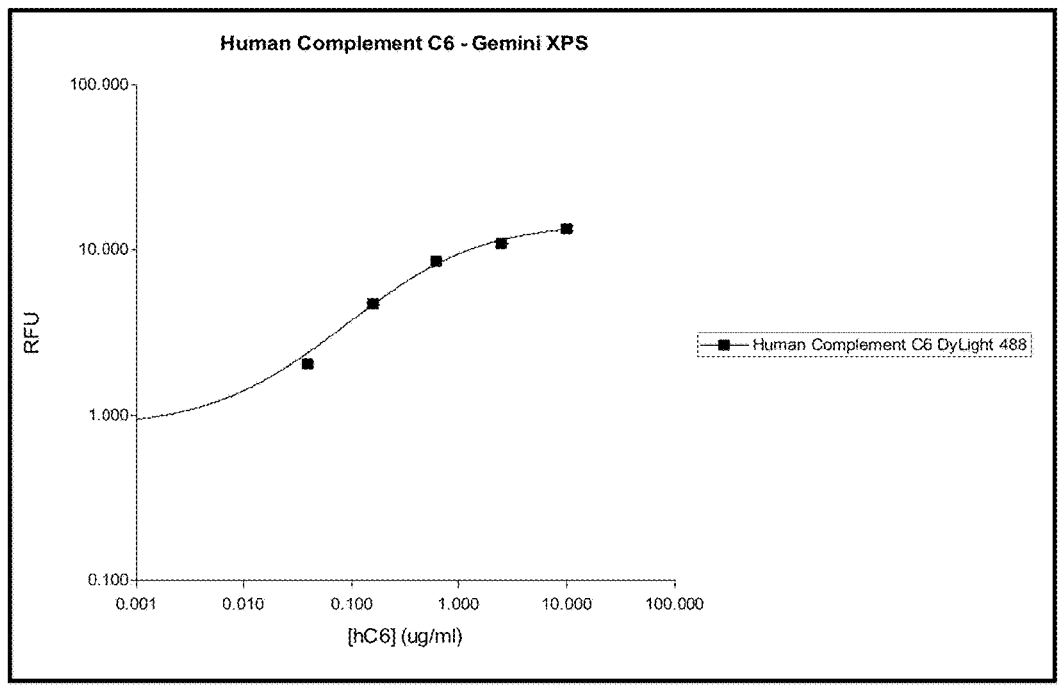
Figure 36A:
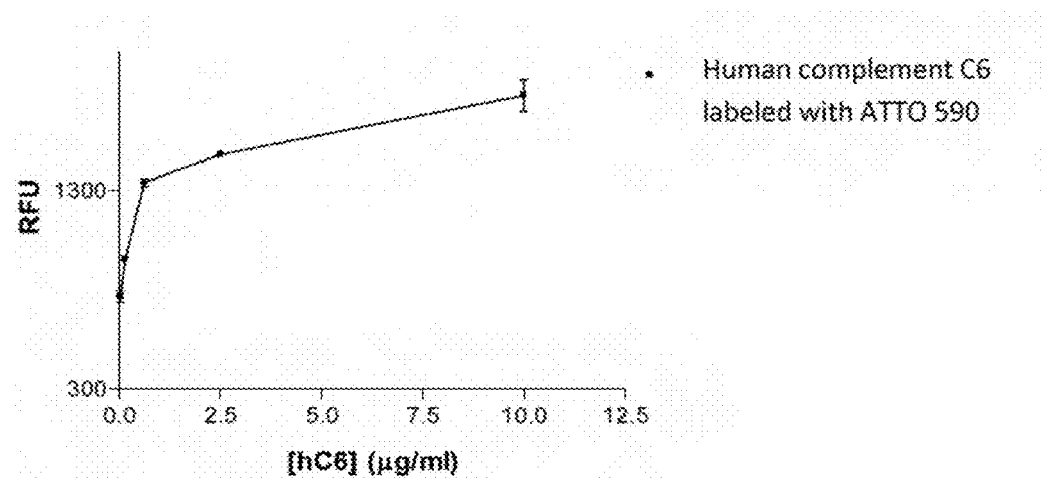
FIG. 36 (a) and (b) are a standard curve generated using the disclosed assay system to perform sandwich immunoassays using Human Complement C6 over-labeled with ATTO 590 using the BioTek FLx800 microplate reader.
Figure 36B:
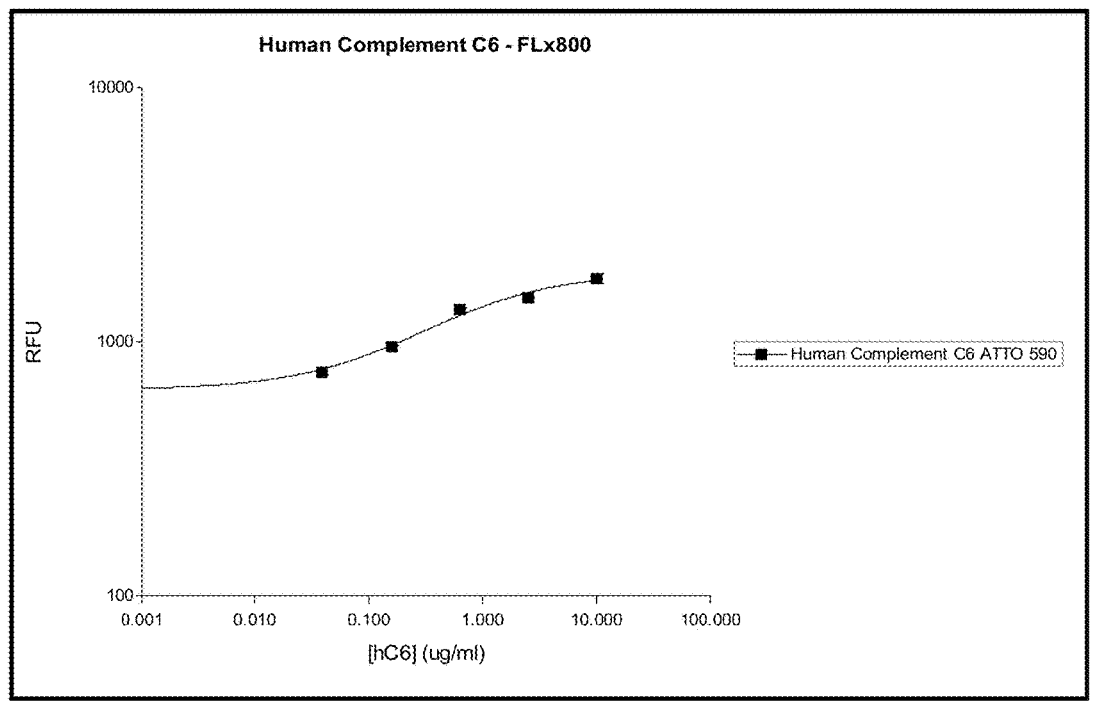
Figure 37A:
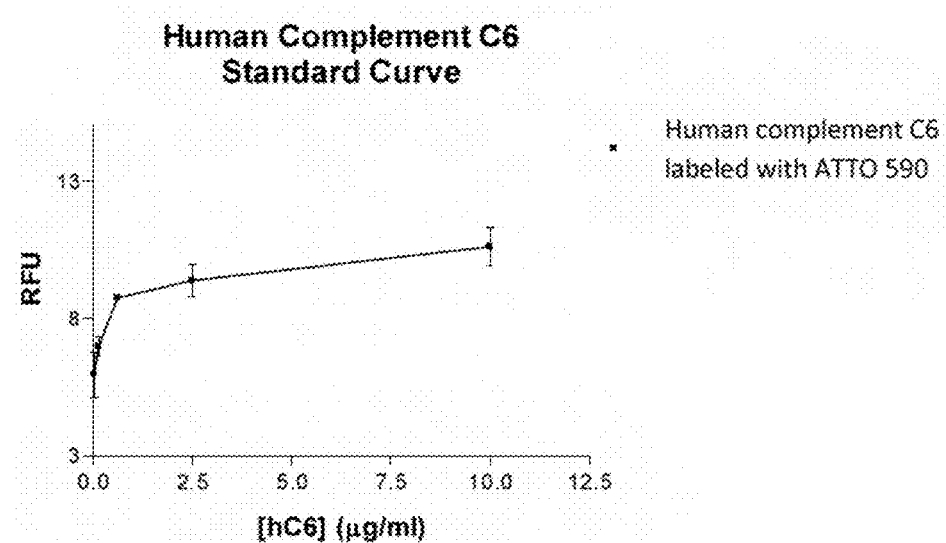
FIG. 37 (a) and (b) are standard curves generated using the disclosed assay system to perform sandwich immunoassays using Human Complement C6 over-labeled with ATTO 590 using the Molecular Devices Gemini XPS microplate reader.
Figure 37B:
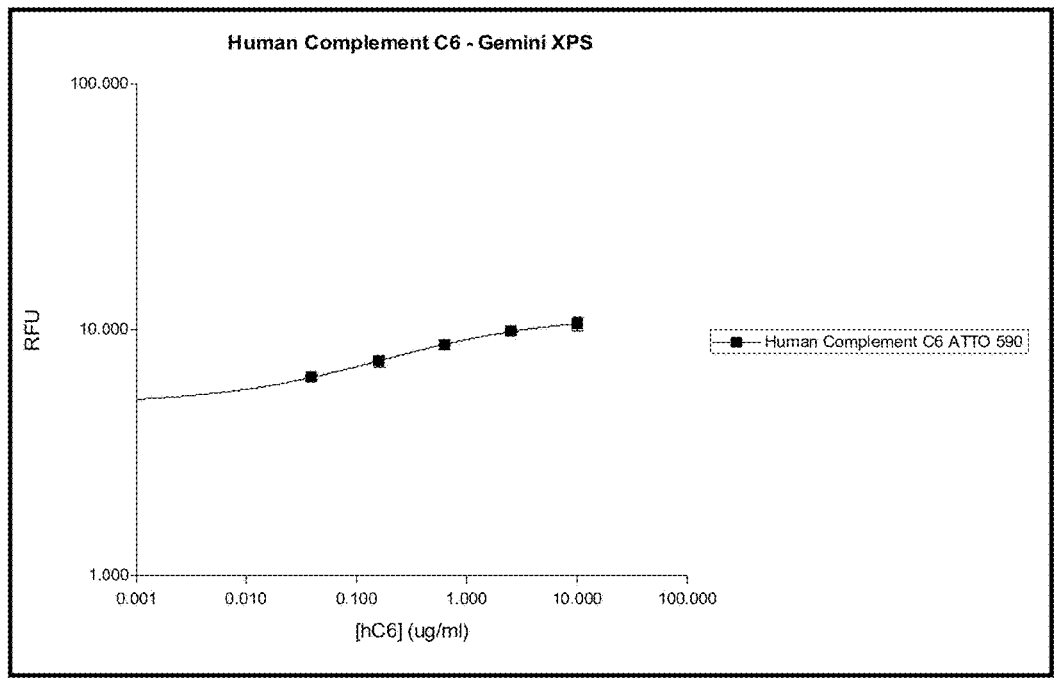
Figure 38A:
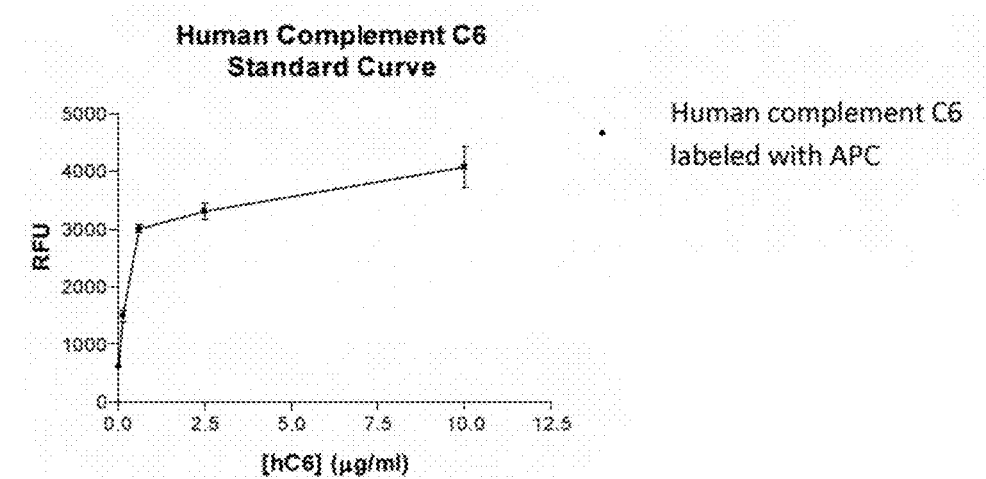
FIG. 38 (a) and (b) are standard curves generated using the disclosed assay system to perform sandwich immunoassays using Human Complement C6 over-labeled with APC using the BioTek FLx800 microplate reader.
Figure 38B:
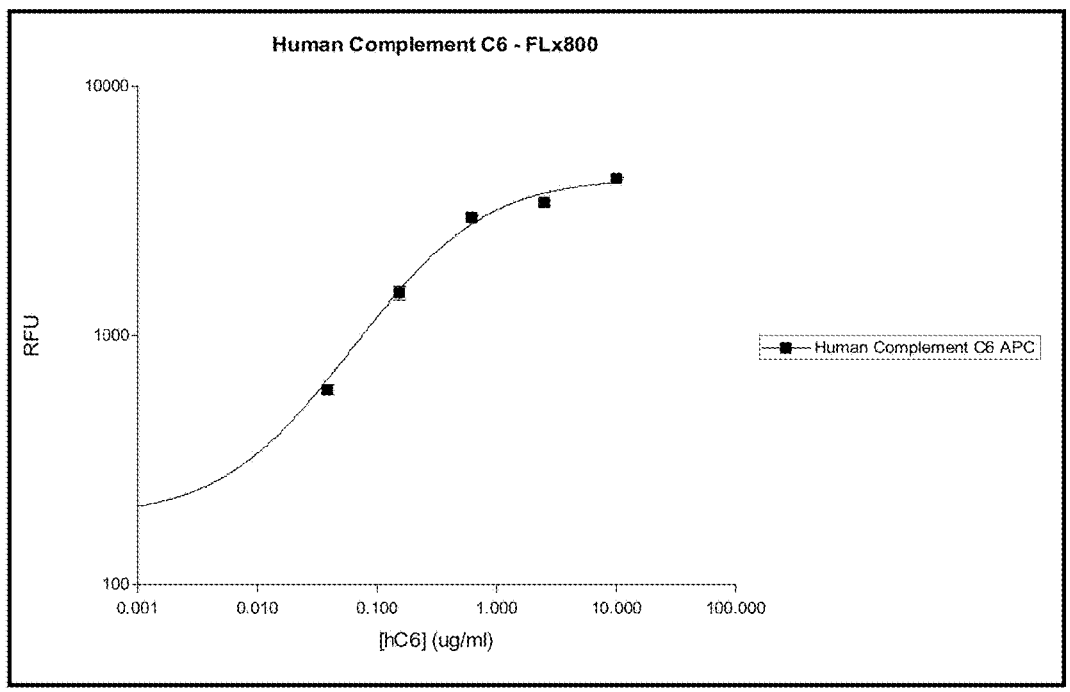
Figure 39A:
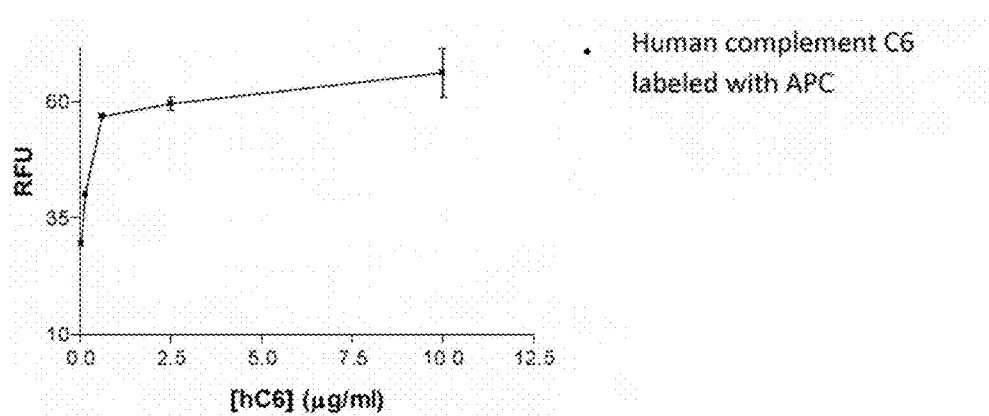
FIG. 39 (a) and (b) are standard curves generated using the disclosed assay system to perform sandwich immunoassays using Human Complement C6 over-labeled with APC using the Molecular Devices Gemini XPS microplate reader.
Figure 39B:
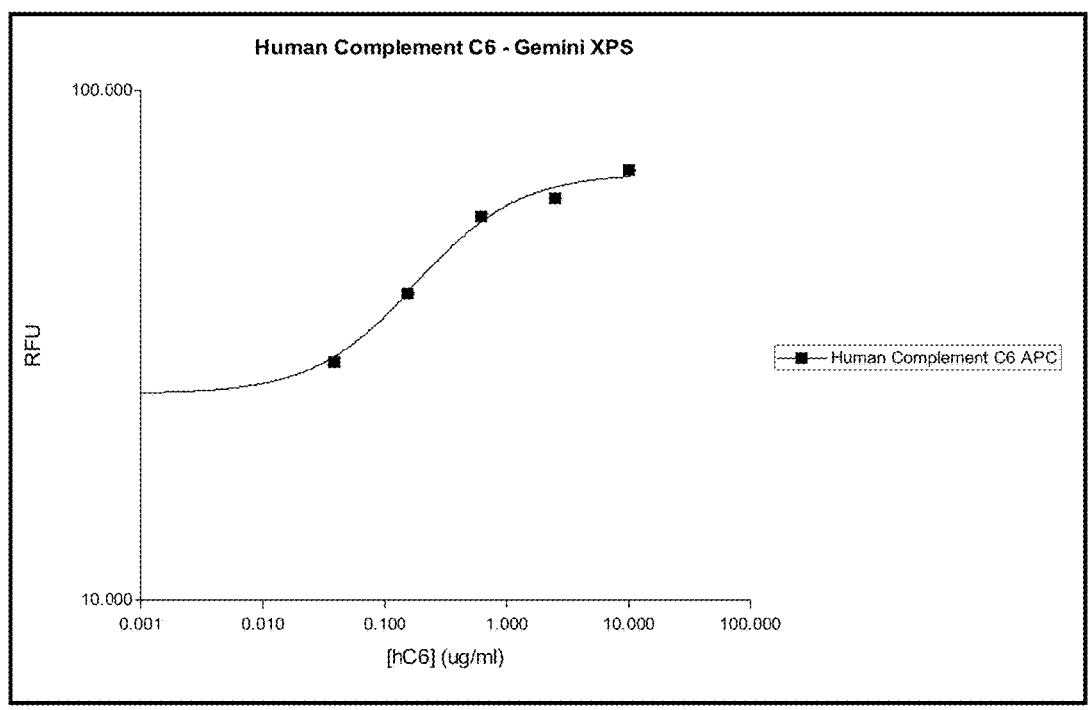
Figure 40A:
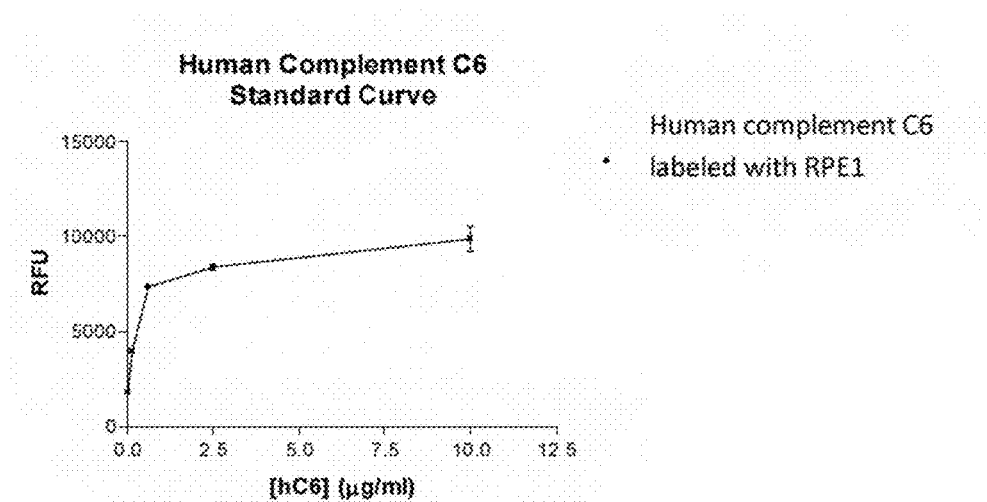
FIG. 40 (a) and (b) are standard curves generated using the disclosed assay system to perform sandwich immunoassays using Human Complement C6 over-labeled with RPE1 using the BioTek FLx800 microplate reader.
Figure 40B:
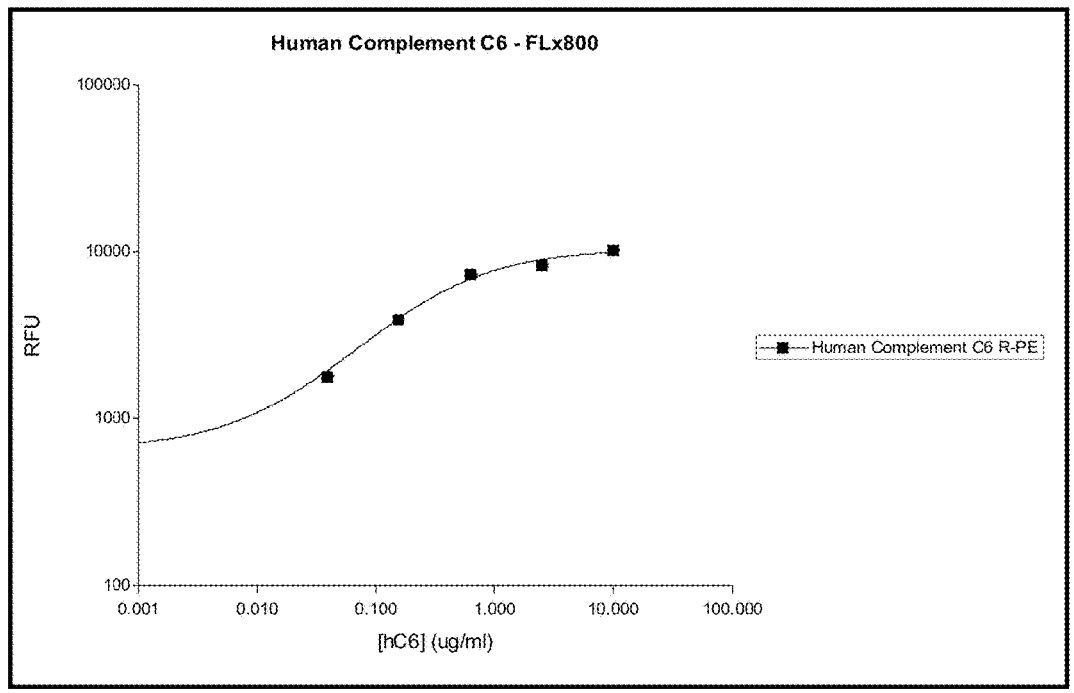
Figure 41A:
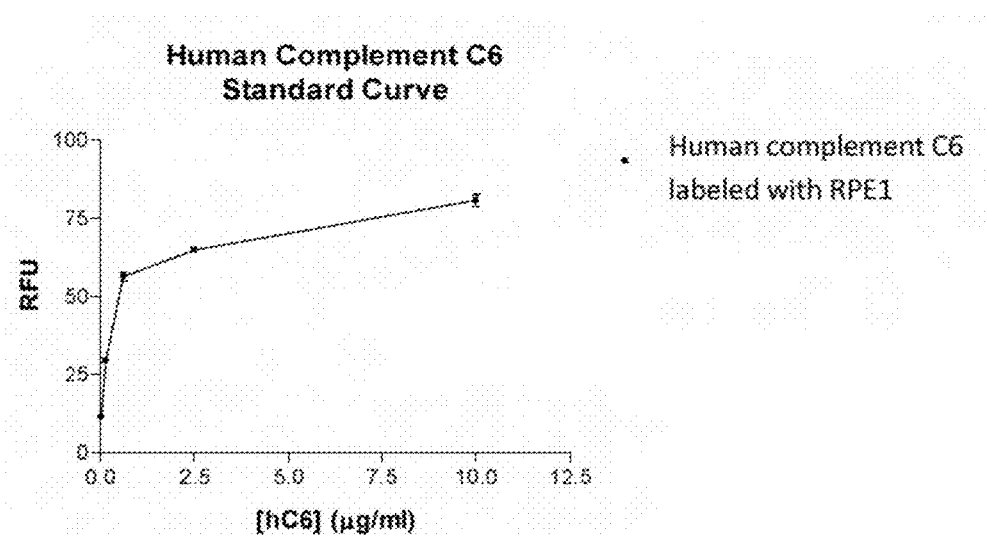
FIG. 41 (a) and (b) are standard curves generated using the disclosed assay system to perform sandwich immunoassays using Human Complement C6 over-labeled with RPE1 using the Molecular Devices Gemini XPS microplate reader.
Figure 41B:
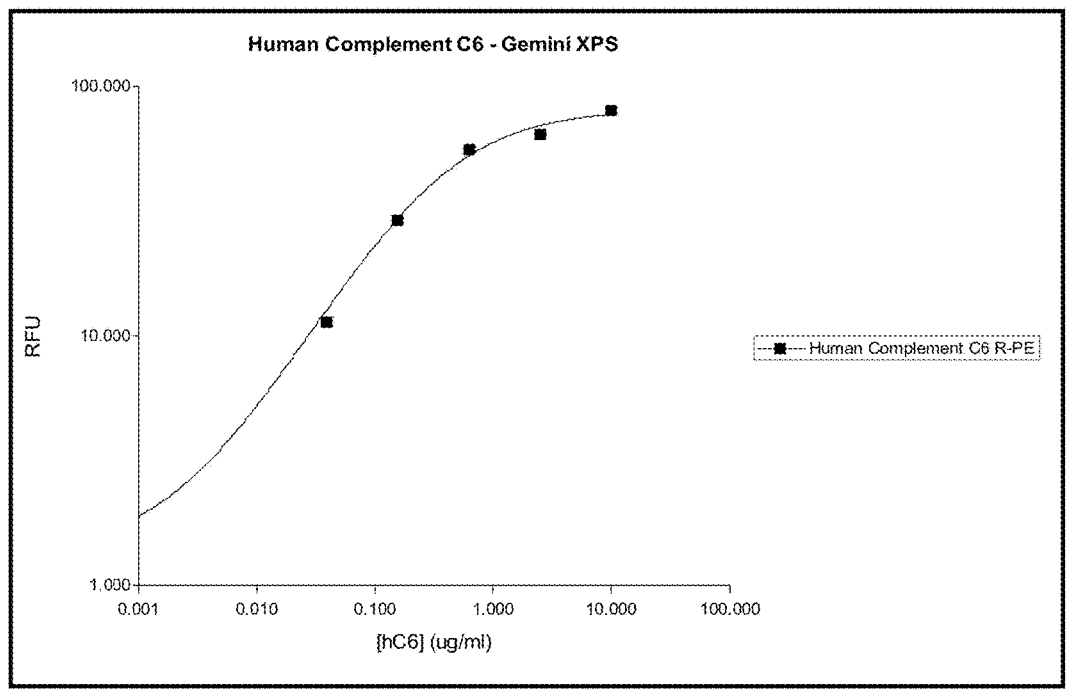

Human Complement C6 ELISA system performance using a sandwich immunoassay technique and read using the Molecular Devices SpectraMax 340PC microplate reader has been evaluated (FIG. 33). Human Complement C6 new assay system using Pierce DyLight 488, ATTO 590, APC and RPE1 labeled detection antibodies to perform sandwich immunoassays and read using the BioTek FLx800 microplate reader (FIG. 34, 36, 38, 40) and Molecular Devices Gemini XPS microplate reader have also been evaluated (FIG. 35, 37, 39, 41).

The data demonstrates the performance similarities in human complement C6 determination of the new system versus the ELISA system. The ELISA system is more sensitive than the new assay system, but the new system has wider dynamic range. The performance characterization is summarized in table 7.

TABLE 7

ELISA performance vs. new assay system in the sandwich immunoassay system to determine human complement C6

|  | ELISA System | DyLight 488/Gemni XPS | DyLight 488/FLx800 | ATTO 590/Gemni XPS | ATTO 590/FLx800 |
| --- | --- | --- | --- | --- | --- |
| Standard Range | 50-0.781 ng/ml | 10-0.0391 μg/ml | 10-0.0391 μg/ml | 10-0.0391 μg/ml | 10-0.0391 μg/ml |
| Intra-assay CV | 2.2 | 3.7 | 4.2 | 4.3 | 11.5 |
| Inter-assay CV | 12.9 | 11.5 | 15.3 | 13.1 | 15.8 |
| Sample value | 28.6 μg/ml | 28.1 μg/ml | 28.0 μg/ml | 35.5 μg/ml | 28.3 μg/ml |
| Sensitivity | 0.195 ng/ml | 0.01 μg/ml | 0.01 μg/ml | 0.0391 μg/ml | 0.0391 μg/ml |

TABLE 7-continued

ELISA performance vs. new assay system in the sandwich immunoassay system to determine human complement C6

|  | ELISA | APC/Gemni System | APC/FLx800 XPS | RPE1/Gemni | RPE1/FLx800 XPS |
|---|---|---|---|---|---|
| Standard Range | 50-0.781 ng/ml | 10-0.0391 µg/ml | 10-0.0391 µg/ml | 10-0.0391 µg/ml | 10-0.0391 µg/ml |
| Intra-assay CV | 2.2 | 2.6 | 5.9 | 4.6 | 4.6 |
| Inter-assay CV | 12.9 | 6.2 | 4.8 | 14.3 | 12.7 |
| Sample value | 28.6 µg/ml | 16.9 µg/ml | 20.9 µg/ml | 30.6 µg/ml | 26.7 µg/ml |
| Sensitivity | 0.195 ng/ml | 0.0391 ug/ml | 0.0391 ug/ml | 0.01 µg/ml | 0.01 µg/ml |

The new Human complement C5 and C6 assays have shown similar performances compared to those of the ELISA system.

I. Human Complement C5 and Complement C6 Multiplex Assay

Next, demonstrated below is the similarity of performance between current ELISA and the new multiplex assay of the Human Complement C5 assay and Human Complement C6 assay using different fluorescent proteins and dyes. Pierce DyLight 488 and ATTO 590 dyes are used to label Human Complement C5 and C6 to form a multiplex. RPE1 and APC labeled Human Complement C5 multiplex with APC and RPE1 labeled Human Complement C6. Results are evaluated below.

Figure 42A:
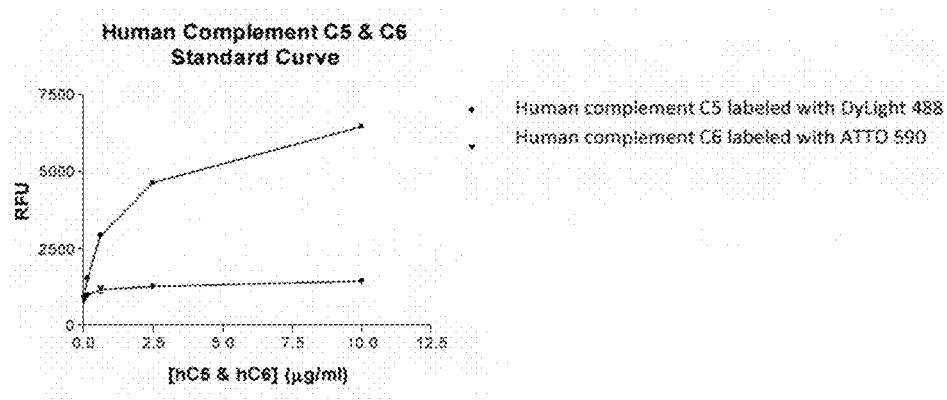
FIG. 42 (a) and (b) are standard curves generated using the disclosed assay system to perform a multiplex assay using a multiplex of human Complement C5 antibody labeled with DyLight 488 and human Complement C6 labeled with ATTO 590, read using the BioTek FLx800 microplate reader.
Figure 42B:
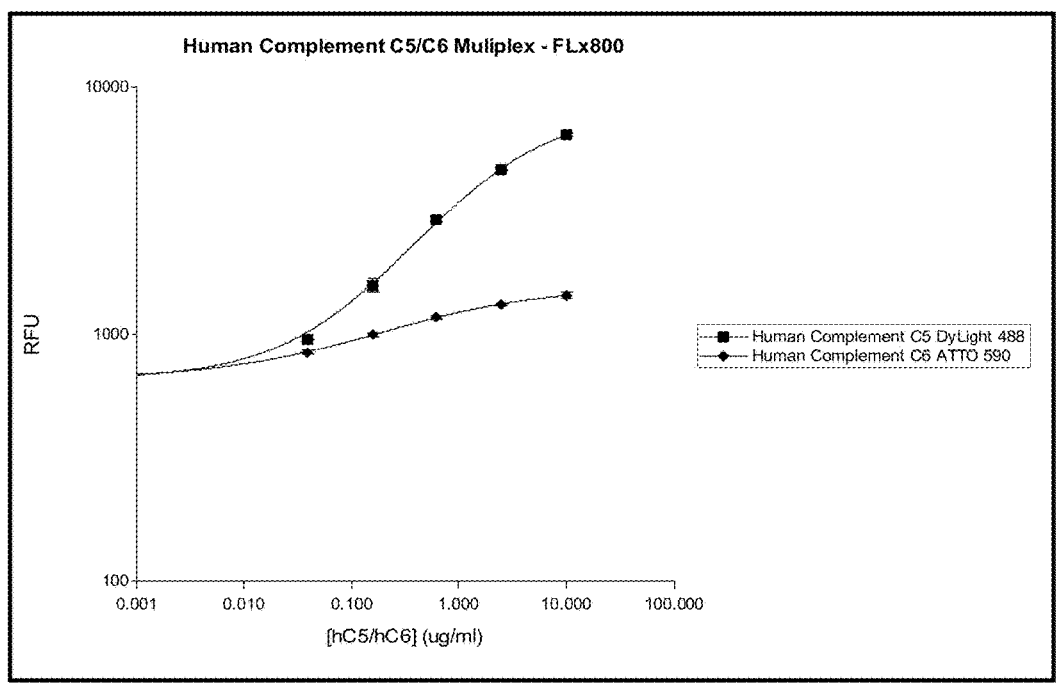
Figure 43A:
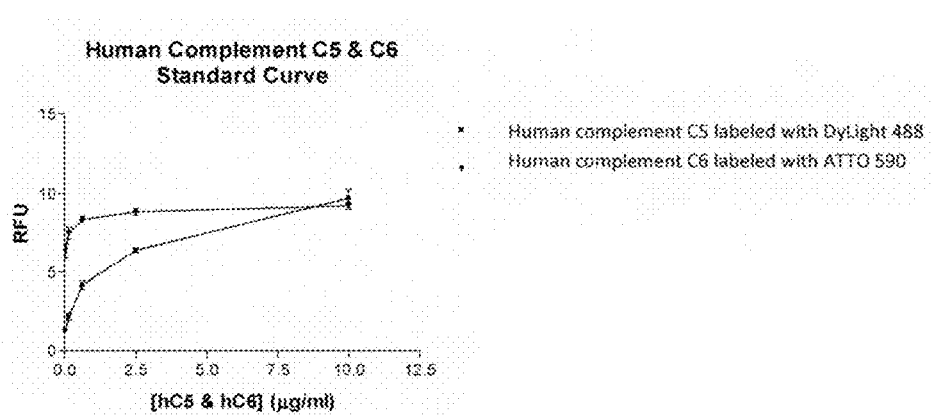
FIG. 43 (a) and (b) are standard curves generated using the disclosed assay system to perform a multiplex assay using a multiplex of human Complement C5 antibody labeled with DyLight 488 and human Complement C6 labeled with ATTO 590, read using the Molecular Devices Gemini XPS microplate reader.
Figure 43B:
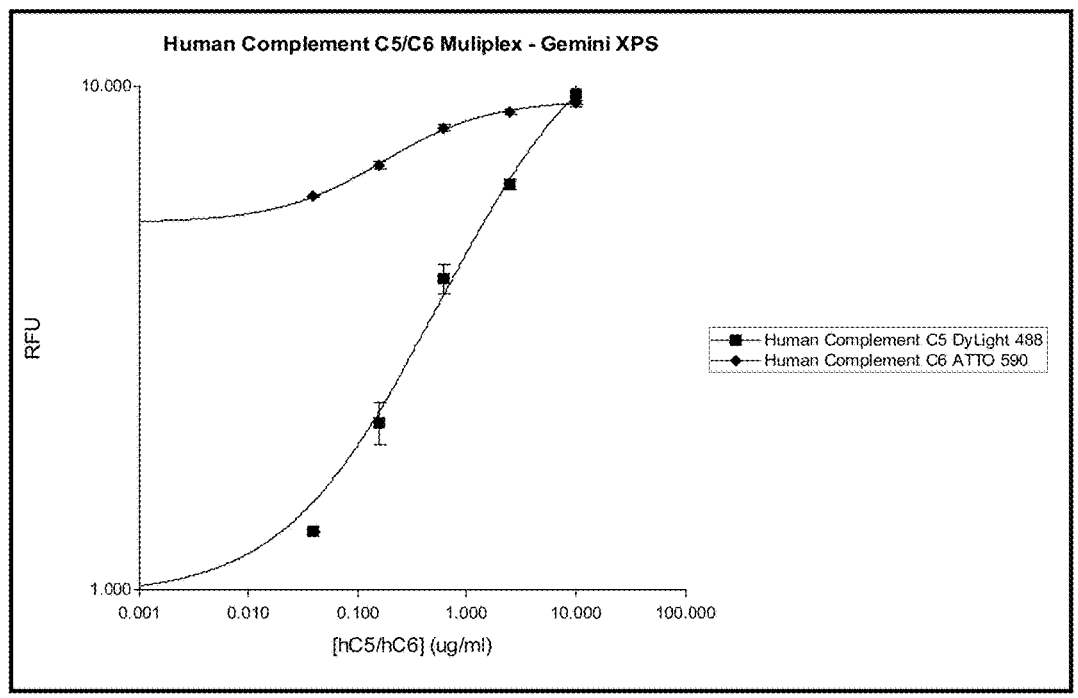

1. Human Complement C5 antibody labeled with DyLight 488 and Human Complement C6 labeled with ATTO 590 multiplex are read using the BioTek FLx800 microplate reader (FIG. 42) and Molecular Devices Gemini XPS microplate reader (FIG. 43).

The data shows that Human Complement C5 antibody labeled with DyLight 488 and Human Complement C6 antibody labeled with ATTO 590 multiplex in one assay and can be read without significant interference between each other. Table 8 summarizes the performance of this multiplex.

TABLE 8

Human complement C5 antibody labeled DyLiqht 488 and Human complement C6 antibody labeled ATTO 590 multiplex performance

|  | C5 ELISA System | C6 ELISA System | C5 DyLight 488/Gemini XPS | C5 DyLight 488/FLx800 | C6 ATTO 590/Gemini XPS | C6 ATTO 590/FLx800 |
|---|---|---|---|---|---|---|
| Standard Range | 10-0.156 ng/ml | 50-0.781 ng/ml | 10-0.0391 µg/ml | 10-0.0391 µg/ml | 10-0.0391 µg/ml | 10-0.0391 µg/ml |
| Intra-assay CV | 4.4 | 2.2 | 3.6 | 5.6 | 4.4 | 16.9 |
| Inter-assay CV | 10.7 | 7.9 | 6.1 | 16.7 | 17.6 | 12.6 |
| Sample value | 97.8 µg/ml | 28.6 µg/ml | 75.6 µg/ml | 72.4 µg/ml | 26.1 µg/ml | 23.4 µg/ml |
| Sensitivity | 0.156 ng/ml | 0.195 ng/ml | 0.0391 µg/ml | 0.0391 µg/ml | 0.0391 µg/ml | 0.0391 µg/ml |

Figure 44A:
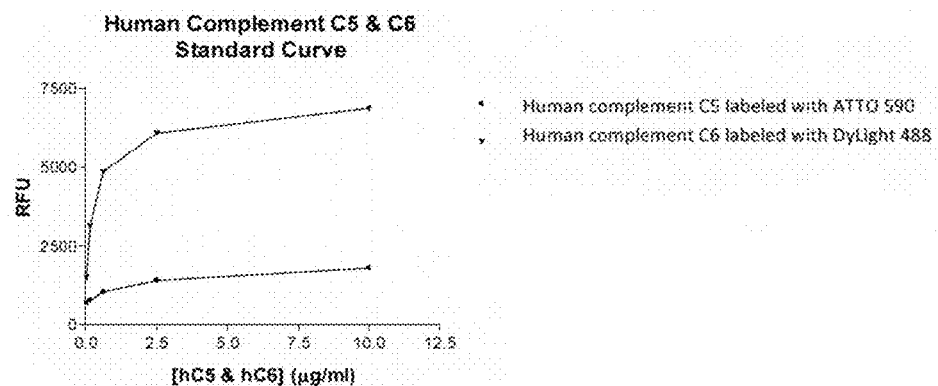
FIG. 44 (a) and (b) are standard curves generated using the disclosed assay system to perform a multiplex assay using a multiplex of Human complement C5 antibody labeled with ATTO 590 and Human complement C6 antibody labeled with DyLight 488, read using the BioTek FLx800 microplate reader.
Figure 44B:
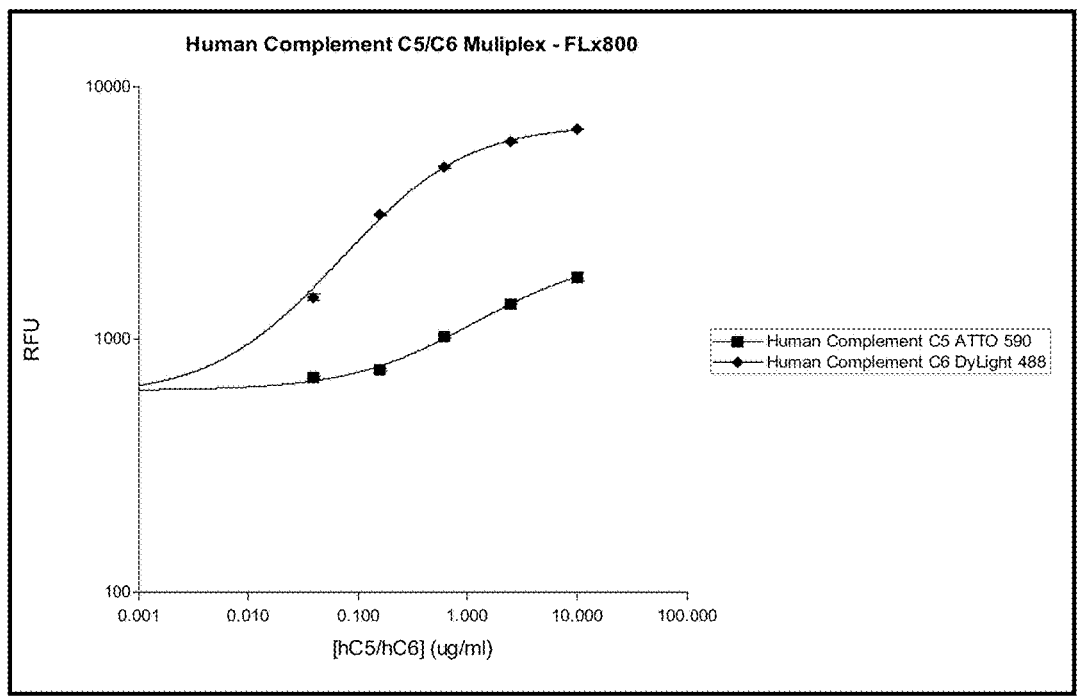
Figure 45A:
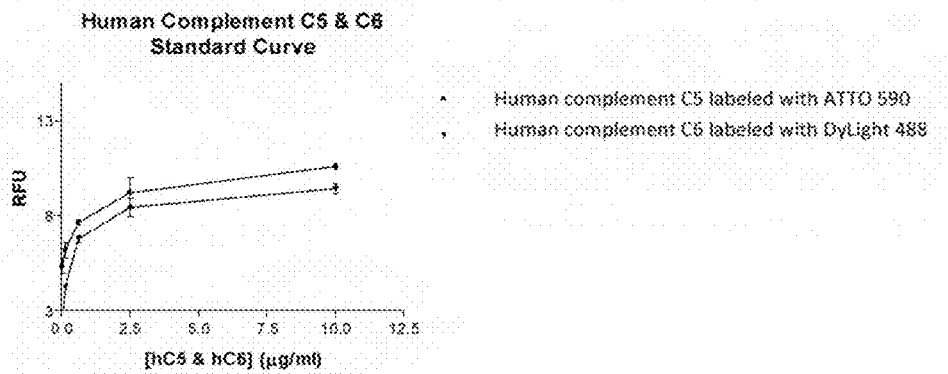
FIG. 45 (a) and (b) are standard curves generated using the disclosed assay system to perform a multiplex assay using a multiplex of Human complement C5 antibody labeled with ATTO 590 and Human complement C6 antibody labeled with DyLight 488, read using the Molecular Devices Gemini XPS microplate reader.
Figure 45B:
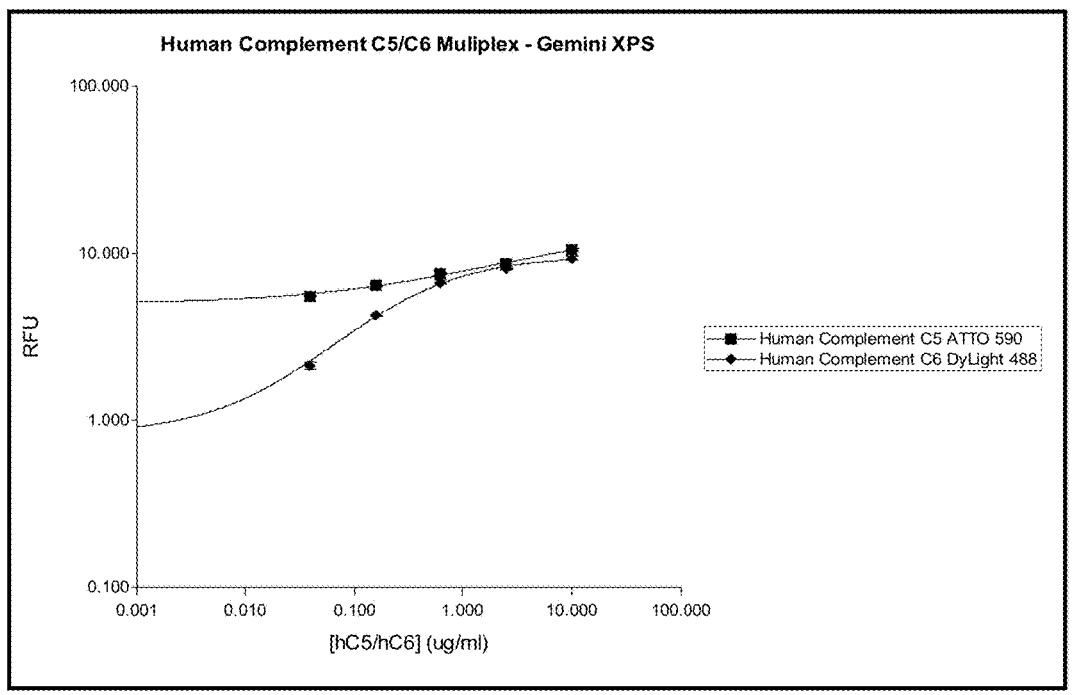

2. Human complement C5 antibody labeled with ATTO 590 and Human complement C6 antibody labeled with DyLight 488 multiplex and are read using the BioTek FLx800 microplate reader (FIG. 44) and the Molecular Devices Gemini XPS microplate reader (FIG. 45).

The data shows that the Human Complement C5 antibody labeled with ATTO 590 and Human Complement C6 antibody labeled with DyLight 488 multiplex in one assay and can be read without significant interference with each other. Table 9 summarizes the performance of this multiplex.

TABLE 9

Human complement C5 antibody labeled ATTO 590 and Human complement C6 antibody labeled DyLight 488 multiplex performance

|  | C5 ELISA System | C6 ELISA System | C5 ATTO 590/Gemini XPS | C5 ATTO 590/FLx800 | C6 DyLight 488/Gemini XPS | C6 DyLight 488/FLx800 |
|---|---|---|---|---|---|---|
| Standard Range | 10-0.156 ng/ml | 50-0.781 ng/ml | 10-0.0391 µg/ml | 10-0.0391 µg/ml | 10-0.0391 µg/ml | 10-0.0391 µg/ml |

TABLE 9-continued

Human complement C5 antibody labeled ATTO 590 and Human complement C6 antibody labeled DyLight 488 multiplex performance

|  | C5 ELISA System | C6 ELISA System | C5 ATTO 590/Gemini XPS | C5 ATTO 590/FLx800 | C6 DyLight 488/Gemini XPS | C6 DyLight 488/FLx800 |
|---|---|---|---|---|---|---|
| Intra-assay CV | 4.4 | 2.2 | 5.3 | 11.3 | 2.6 | 3.0 |
| Inter-assay CV | 10.7 | 7.9 | 7.4 | 17.1 | 16.7 | 4.6 |
| Sample value | 97.8 µg/ml | 28.6 µg/ml | 56.7 µg/ml | 58.3 µg/ml | 31.9 µg/ml | 29.5 µg/ml |
| Sensitivity | 0.156 ng/ml | 0.195 ng/ml | 0.0391 µg/ml | 0.0391 µg/ml | 0.01 µg/ml | 0.01 µg/ml |

Figure 46A:
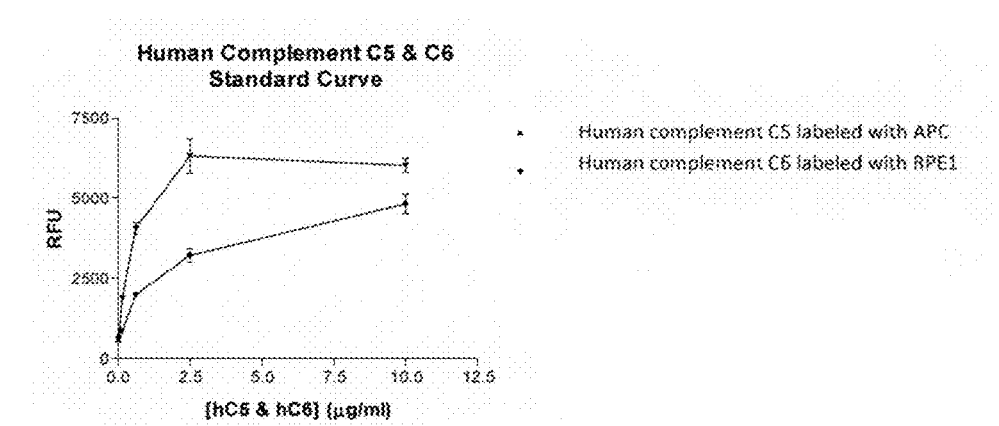
FIG. 46 (a) and (b) are standard curves generated using the disclosed assay system to perform a multiplex assay using a multiplex of Human complement C5 antibody labeled with APC and Human complement C6 antibody labeled with RPE1, read using the BioTek FLx800 microplate reader.
Figure 46B:
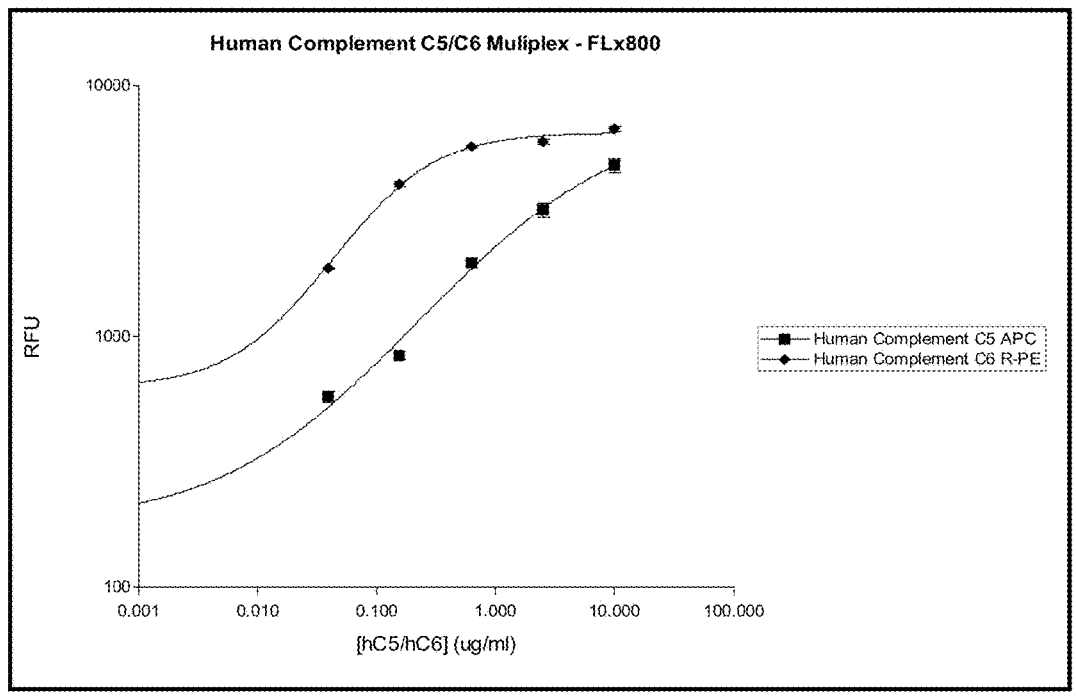
Figure 47A:
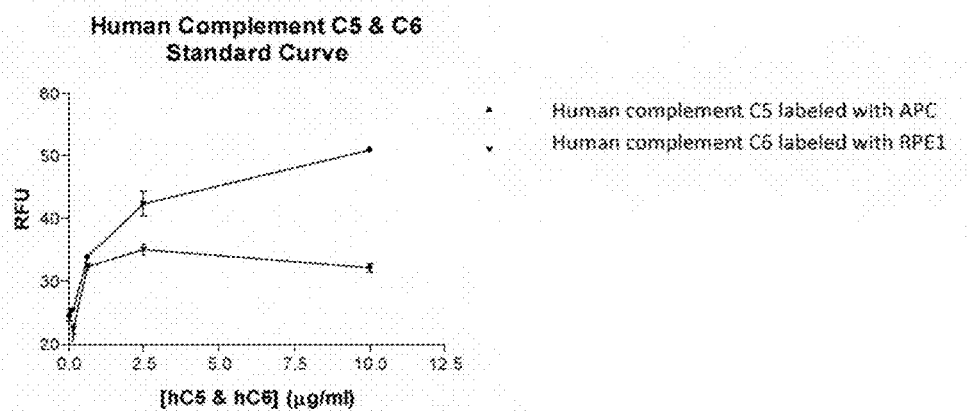
FIG. 47 (a) and (b) are standard curves generated using the disclosed assay system to perform a multiplex assay using a multiplex of Human complement C5 antibody labeled with APC and Human complement C6 antibody labeled with RPE1, read using the Molecular Devices Gemini XPS microplate reader.
Figure 47B:
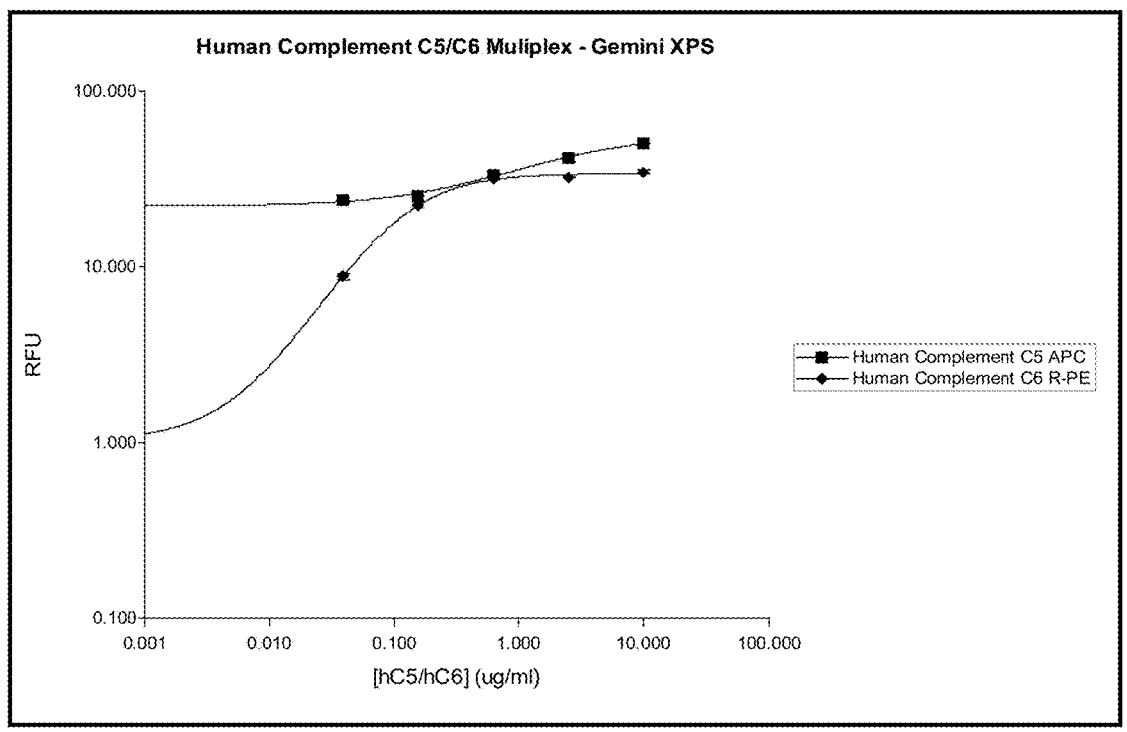

3. Human complement C5 antibody labeled with APC and Human complement C6 labeled with RPE1 multiplex and are read using the BioTek FLx800 microplate reader (FIG. 46) and the Molecular Devices Gemini XPS microplate reader (FIG. 47).

C5 antibody labeled with APC and Human complement C6 antibody labeled with RPE1 multiplex in one assay and can be read without significant interference between each other. Table 10 summarizes the performance of this multiplex.

TABLE 10

Human Complement C5 antibody labeled APC and Human Complement C6 antibody labeled RPE1 multiplex performance

|  | C5 ELISA System | C6 ELISA System | C5 APC/Gemini XPS | C5 APC/FLx800 | C6 RPE1/Gemini XPS | C6 RPE1/FLx800 |
|---|---|---|---|---|---|---|
| Standard Range | 10-0.156 ng/ml | 50-0.781 ng/ml | 10-0.0391 µg/ml | 10-0.0391 µg/ml | 2.5-0.0391 µg/ml | 2.5-0.0391 µg/ml |
| Intra-assay CV | 4.4 | 2.2 | 3.5 | 5.4 | 3.9 | 3.4 |
| Inter-assay CV | 10.7 | 7.9 | 13.0 | 16.4 | 14.2 | 12.8 |
| Sample value | 97.8 µg/ml | 28.6 µg/ml | 96.9 µg/ml | 69.8 µg/ml | 20.7 µg/ml | 18.6 µg/ml |
| Sensitivity | 0.156 ng/ml | 0.195 ng/ml | 0.0391 µg/ml | 0.0391 µg/ml | 0.01 µg/ml | 0.01 µg/ml |

Figure 48A:
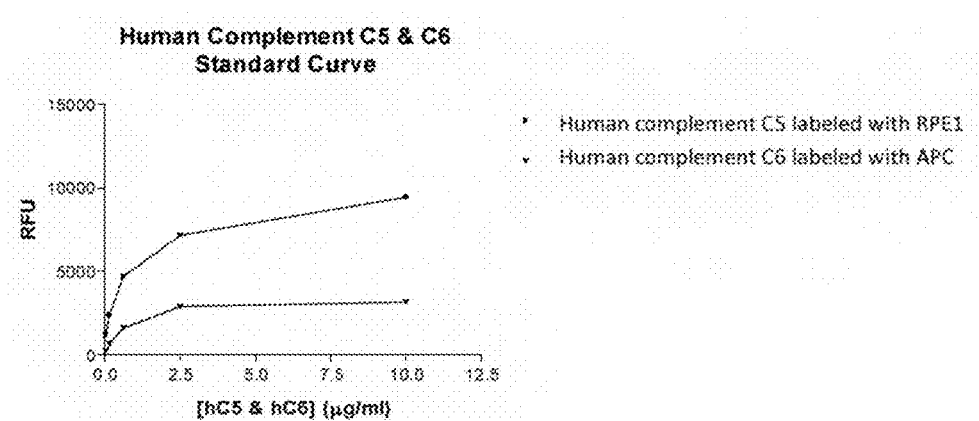
FIG. 48 (a) and (b) are standard curves generated using the disclosed assay system to perform a multiplex assay using a multiplex of Human complement C5 antibody labeled with RPE1 and Human complement C6 antibody labeled with APC, read using the BioTek FLx800 microplate reader.
Figure 48B:
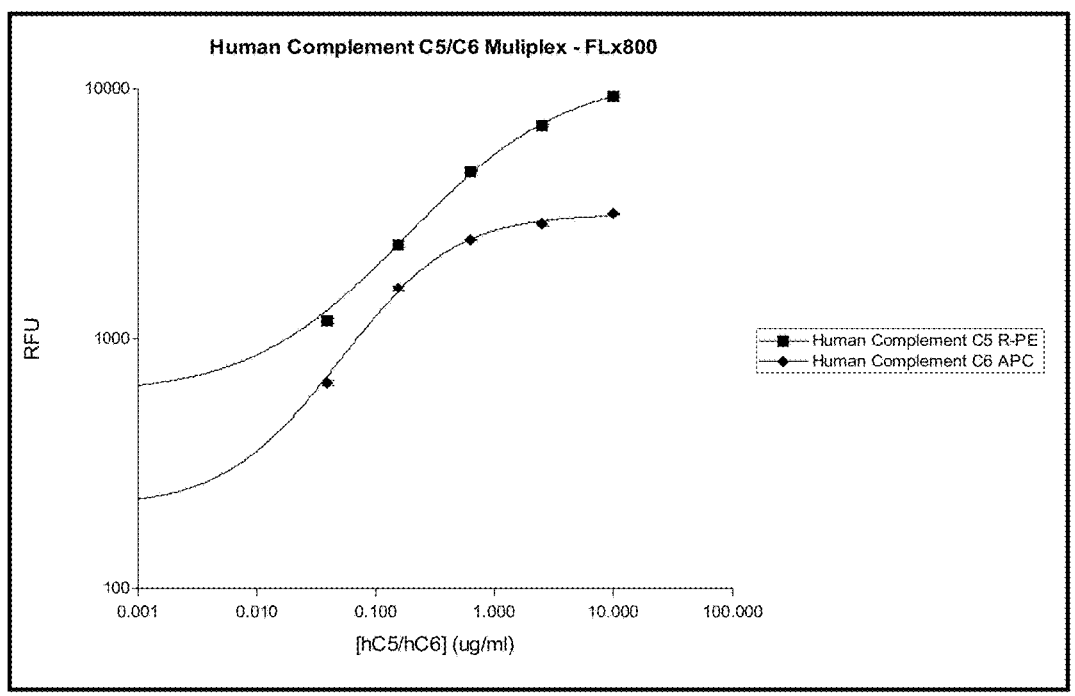
Figure 49A:
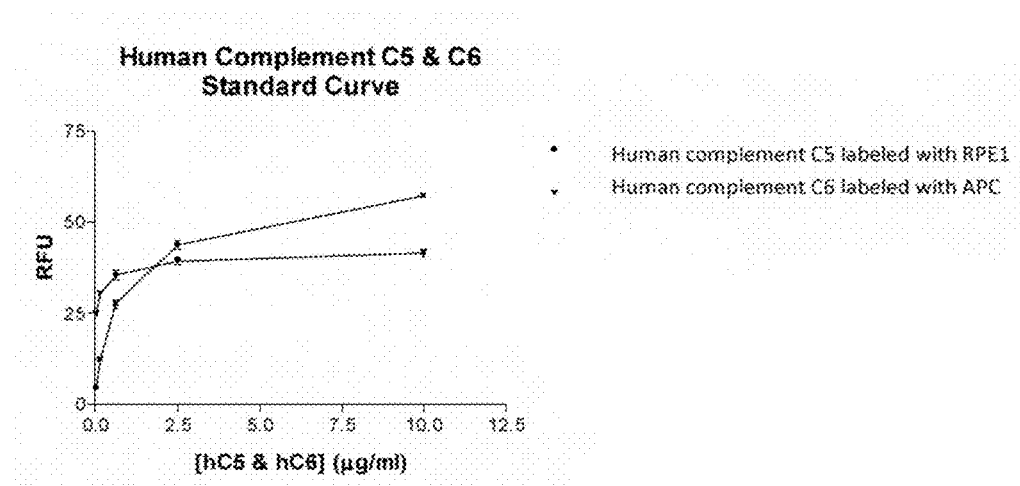
FIG. 49 (a) and (b) are standard curves generated using the disclosed assay system to perform a multiplex assay using a multiplex of Human complement C5 antibody labeled with RPE1 and Human complement C6 antibody labeled with APC, read using the Molecular Devices Gemini XPS microplate reader.
Figure 49B:
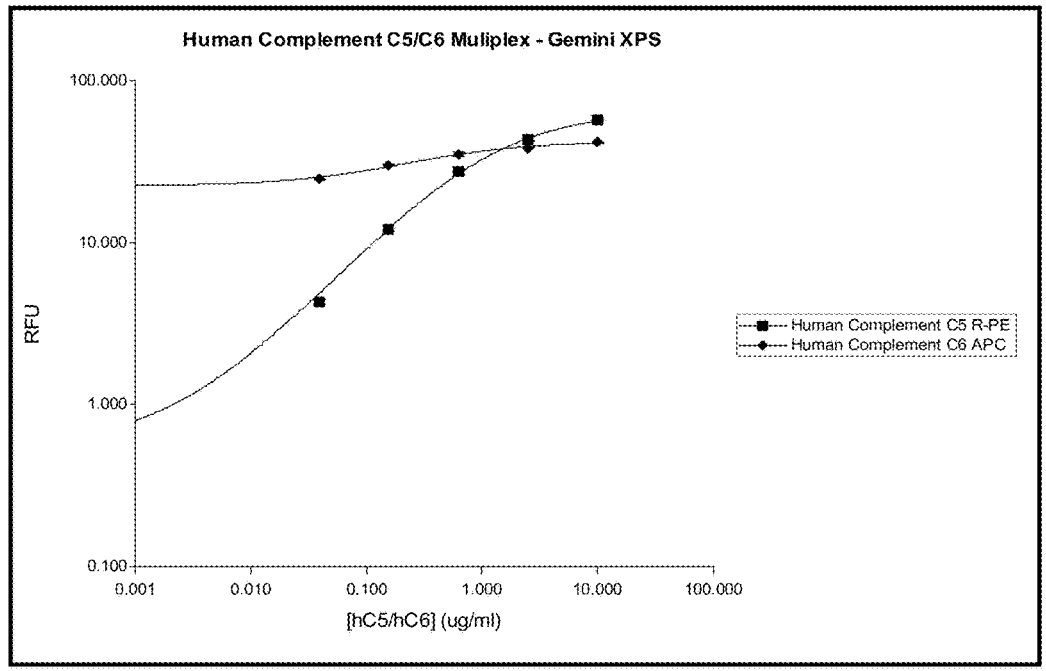
Figure 50:
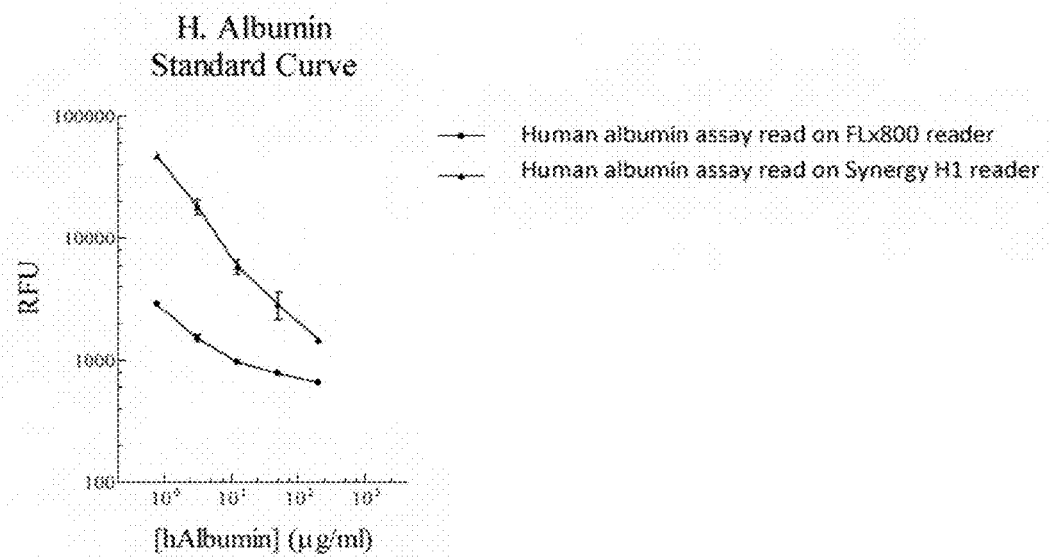
FIG. 50 shows human albumin standard curves generated with data using the disclosed assay system read on a FLx800 reader (squares) and on a Synergy H1 reader (triangles).

4. Human complement C5 antibody labeled with RPE1 and Human complement C6 labeled with APC multiplex and are read using the BioTek FLx800 microplate reader (FIG. 48) and the Molecular Devices Gemini XPS microplate reader (FIG. 49).

The data shows that Human complement C5 antibody labeled with APC and Human complement C6 antibody labeled with RPE1 multiplex in one assay and can be read without significant interference between each other. Table 9 summarizes the performance of this multiplex.

TABLE 11

Human complement C5 antibody labeled APC and Human complement C6 antibody labeled RPE1 multiplex performance

|  | C5 ELISA System | C6 ELISA System | C5 RPE1/Gemini XPS | C5 RPE1/FLx800 | C6 APC/Gemini XPS | C6 APC/FLx800 |
|---|---|---|---|---|---|---|
| Standard Range | 10-0.156 ng/ml | 50-0.781 ng/ml | 10-0.0391 µg/ml | 10-0.0391 µg/ml | 2.5-0.0391 µg/ml | 2.5-0.0391 µg/ml |
| Intra-assay CV | 4.4 | 2.2 | 3.0 | 3.9 | 3.9 | 6.5 |
| Inter-assay CV | 10.7 | 7.9 | 10.1 | 13.9 | 10.9 | 13.7 |
| Sample value | 97.8 µg/ml | 28.6 µg/ml | 87.3 µg/ml | 80.3 µg/ml | 31.1 µg/ml | 20.7 µg/ml |
| Sensitivity | 0.156 ng/ml | 0.195 ng/ml | 0.02 µg/ml | 0.0391 µg/ml | 0.0391 µg/ml | 0.0391 µg/ml |

Example 9: Evaluation of Fluorescent Plate Readers

Three fluorescent plate readers were evaluated using the new assay system, as follows:
1. Gemini Fluorescence Microplate Reader XPS from Molecular Devices The Gemini™ XPS Fluorescence Microplate Reader uses dual monochromators for variable wavelength selection between 250 nm and 850 nm to eliminate the need for searching out the right pair of excitation and emission filters. Dual monochromators also enable wavelength scanning across a range of wavelengths in increments as small as 1 nm to optimize assay parameters.
2. The FLx800™ Multi-Detection Microplate Reader from BioTek The FLx800™ Multi-Detection Microplate Reader combines excellent specifications and performance with convenience and ease of use. This design incorporates powerful performance at a price much lower than traditional fluorescence-luminescence microplate readers. The FLx800 line includes several models with options that meet the specific needs of research and OEM users. Top and bottom readings are available to read from 6-well to 384-well micro plates.
3. Synergy™ H1 from BioTek Synergy™ H1 is a flexible monochromator-based multi-mode microplate reader that can be turned into a high-performance patented Hybrid system with the addition of a filter-based optical module. The monochromator optics uses a third generation quadruple grating design that allows working at any excitation or emission wavelength with a 1 nm step. This system supports top and bottom fluorescence intensity, UV-visible absorbance and high performance luminescence detection. It is the ideal system for all the standard microplate applications found in life science research laboratories. The plate reader we evaluated was monochromator optics reader.

Results:

Gemini XPS system tends to give very low RFU compared with BioTek FLx 800 or Synergy H1. The fold difference is in the range of 100 to 1000 fold difference. However, the assay performances are comparable with each other in terms of sample value, intra-assay CV, and inter assay CV from the assays we have shown in the previous section.

For BioTek, two different types of readers were evaluated in three assays to demonstrate whether the Synergy H1 might be a better choice for the assay we developed.

Figure 51:
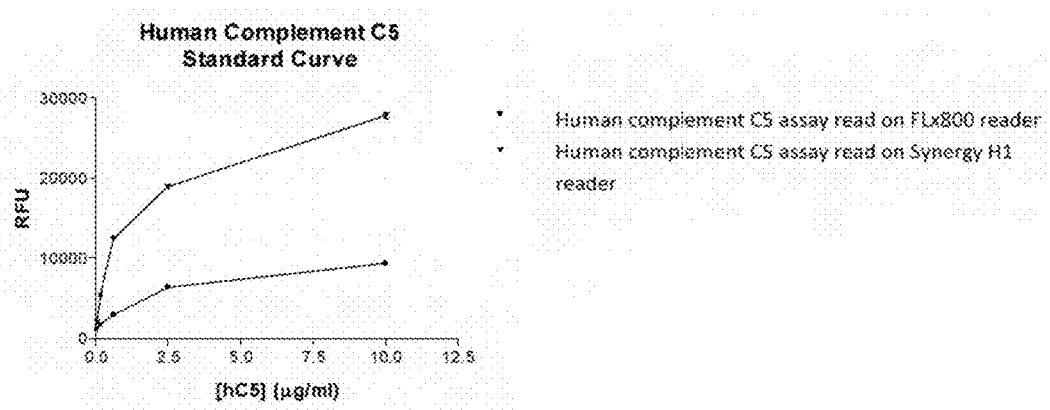
FIG. 51 shows human Complement C5 standard curves generated with data using the disclosed assay system read on a FLx800 reader (squares) and on a Synergy H1 reader (inverted triangles).
Figure 52:
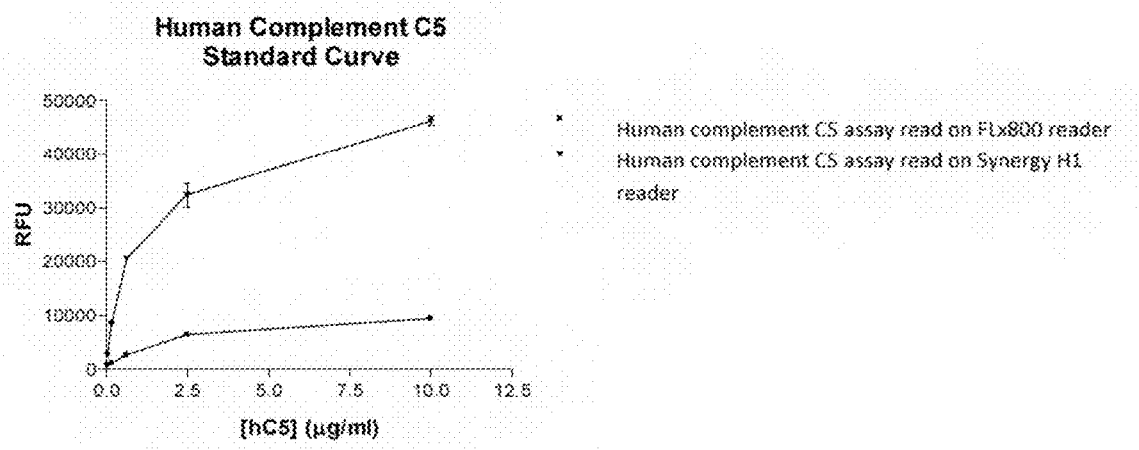
FIG. 52 shows human Complement C5 standard curves generated with data using the disclosed assay system read on a FLx800 reader (squares) and on a Synergy H1 reader (inverted triangles).

Human albumin labeled with RPE1 has been evaluated for both readers as shown in FIG. 45. Human complement C5 antibody labeled with DyLight 488 and RPE1 have been tested on both readers (FIGS. 51 and 52). The data above indicates BioTek Synergy H1 has much better performance when compared with the FLx800 reader.

Figure 53:
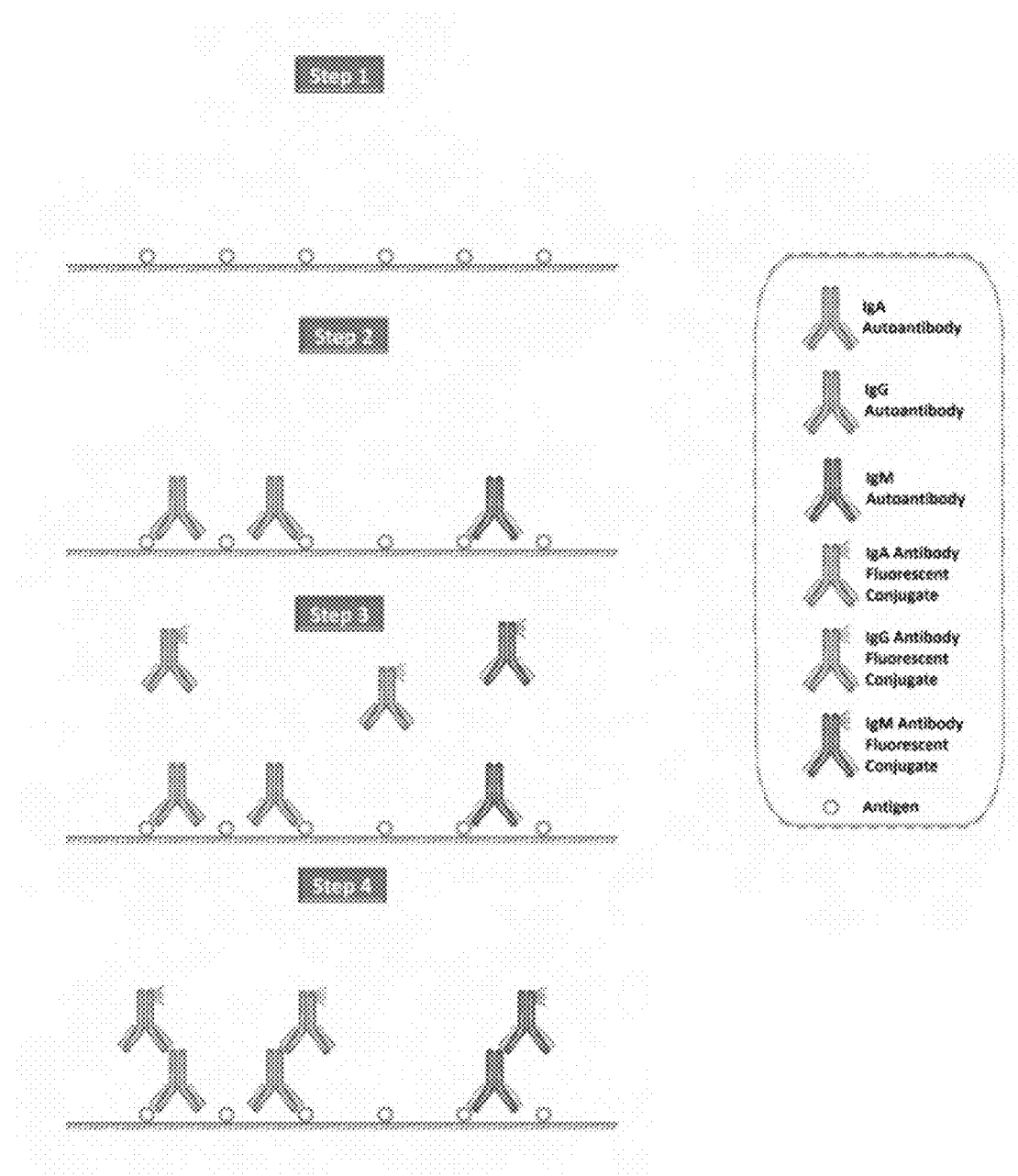
FIG. 53 is a schematic illustration of multiplexing on a protein coated plate for detecting autoantibody IgA, IgG, and IgM against such protein.

Example 10: Multiplex Assay for Autoantibody Against Beta 2-Glycoprotein 1 (Beta 2GP1) in Plasma Samples FIG. 53 is a schematic illustration of multiplexing on a protein coated plate for detecting autoantibody IgA, IgG, and IgM against such protein. The steps are as follows:
Step 1) Antigen is coated uniformly on the microplate.
Step 2) Standard and samples are added to wells. IgA, IgG, and IgM autoantibodies bind the target antigen in the Standard or samples. All unbound materials are washed away.
Step 3) IgA, IgG, and IgM Fluorescent Probes are added to wells and incubated, where they bind to their respective autoantibodies.
Step 4) The microplate is washed and the endpoint fluorescence is measured. The fluorescence intensity is proportional to the concentration of the IgA, IgGG, and IgM autoantibodies in the Standard or samples.

Beta 2 glycoprotein 1 (beta 2GP1, also called apolipoprotein H) is a 326 amino acid polypeptide synthesized by hepatocytes, endothelial cells and trophoblast cells. It contains 5 homologous domains of approximately 60 amino acids each. Domain 5, located at the C terminus, contains a hydrophobic core surrounded by 14 positively charged amino acid residues that promote electrostatic interactions with plasma membranes via interactions with negatively charged phospholipids. Pathologic levels of beta 2 GP1 antibodies occur in patients with anti-phospholipid syndrome (APS). APS is associated with a variety of clinical symptoms notably thrombosis, pregnancy complications, unexplained cutaneous circulatory disturbances (livido reticularis or pyoderma gangrenosum), thrombocytopenia or hemolytic anemia, and nonbacterial thrombotic endocarditis. Beta 2GP1 antibodies are found with increased frequency in patients with systemic rheumatic diseases, especially systemic lupus erythematosus.

A multiplex assay was used to quickly and accurately evaluate plasma levels of the autoantibody against beta 2GP1 as follows.

Materials and Methods:

Materials:

High Binding Plate (Corning Cat #2592)

Reference disease standard (purchased from Bioreclamation) for autoantibody IgA, IgM or IgG to beta 2-glycoprotein I1.

In house developed rabbit polyclonal against human IgA, IgG or IgM for over-labeled with fluorescent protein or dyes. (Over-labeling method detailed above).

Above rabbit IgG against human IgA over-labeled with RPE, rabbit IgG against human IgG over-labeled with Yellow dye (ATTO-430LS dye), and rabbit IgG against human IgM over-labeled with APC.

Normal individual donor and disease patient donor purchased from Bioreclamation.

Beta 2-glycoprotein 1 (Beta 2GP1) purchased from Enzyme Research Laboratory.

Dilution Buffer (Diluent) prepared using affinity column couple to human IgA, IgG, and IgM to deplete normal human plasma to become IgA, IgG and IgM poor plasma as a dilution buffer.

Blocking Buffer—50% FBS

Wash Buffer—PBS pH 7.5 plus 0.1% TWEEN®-20

Stabilizing Solution—$dH_2O$

Fetal Bovine Serum (Biosera)

Methods:
1. Coat beta 2GP1 in PBS at 2 ug/ml overnight at 4° C.
2. Block the plate with 50% (Fetal Bovine Serum) for 4 minutes and then decant the FBS.
3. Mix equal parts of the IgA, IgG, and IgM autoantibodies at 480 Arbitrary Units (AU)/ml to generate a stock solution of 160 AU/ml for each standard. Prepare duplicate or triplicate standard points by serially diluting the standard solution (160 AU/ml) 1:2 with Diluent to generate 80, 40, 20, 10, 5, and 2.5 AU/ml solutions. Diluent serves as the zero standards (0 AU/ml). Any remaining solution should be frozen at −20° C. and used within 30 days.

4. Add 100 µl of beta 2GP1 Standard or sample per well. Cover wells with a sealing film and incubate for 30 minutes at 37° C. Start the timer after the last addition.
5. Wash five times with 200 µl of Wash Buffer manually. Invert the plate each time and decant the contents; hit 4-5 times on absorbent material to completely remove the liquid. If using a machine, wash six times with 300 µl of Wash Buffer and then invert the plate, decanting the contents; hit 4-5 times on absorbent material to completely remove the liquid.
6. Mix equal parts of the IgA Red, IgG Yellow, and IgM Blue fluorescent probe. Add 100 µl of the fluorescent probe mixture per well. Cover wells with a sealing film and incubate for 30 minutes at 37° C. Start the timer after the last addition.
7. Wash the microplate as described above.
8. Immediately add 50 µl of Stabilizing Solution to each well.
9. For IgA Red, read the endpoint fluorescence on a microplate reader at an excitation wavelength of 488 nm and emission wavelength of 576 nm. For IgG Yellow, read the endpoint fluorescence on a microplate reader at an excitation wavelength of 433 nm and emission wavelength of 547 nm. For IgM Blue, read the endpoint fluorescence on a microplate reader at an excitation wavelength of 595 nm and emission wavelength of 660 nm. All reads should be completed within 2 hours of adding the Stabilizing Solution.

Results and Discussion

Figure 54:
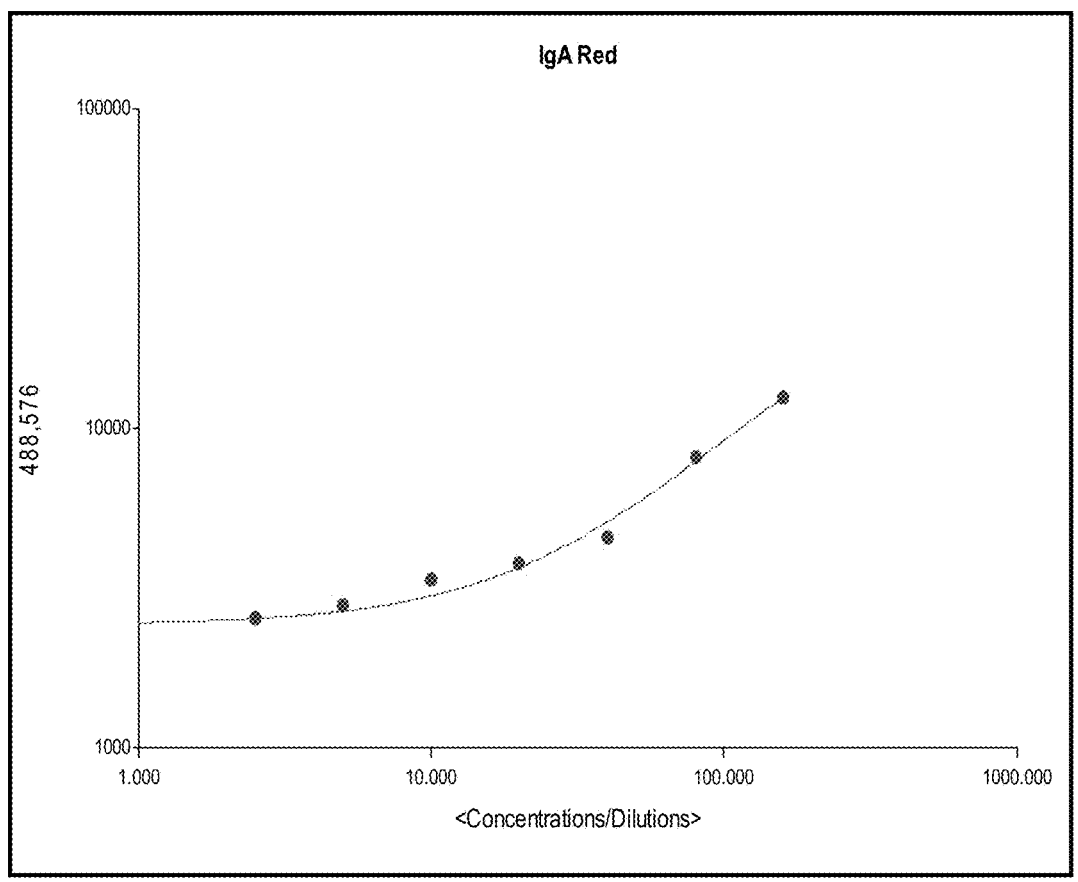
FIG. 54 is a standard curve of autoantibody IgA against human beta 2GP1.
Figure 55:
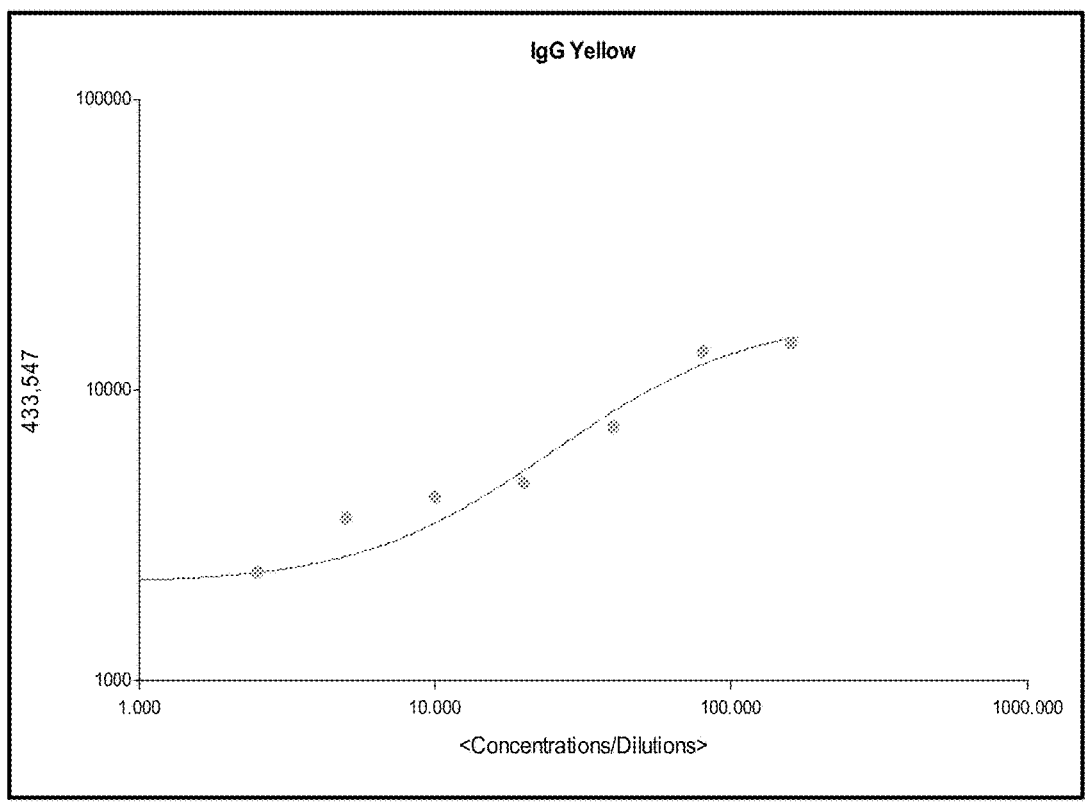
FIG. 55 is a standard curve of autoantibody IgG against human beta 2GP1.
Figure 56:
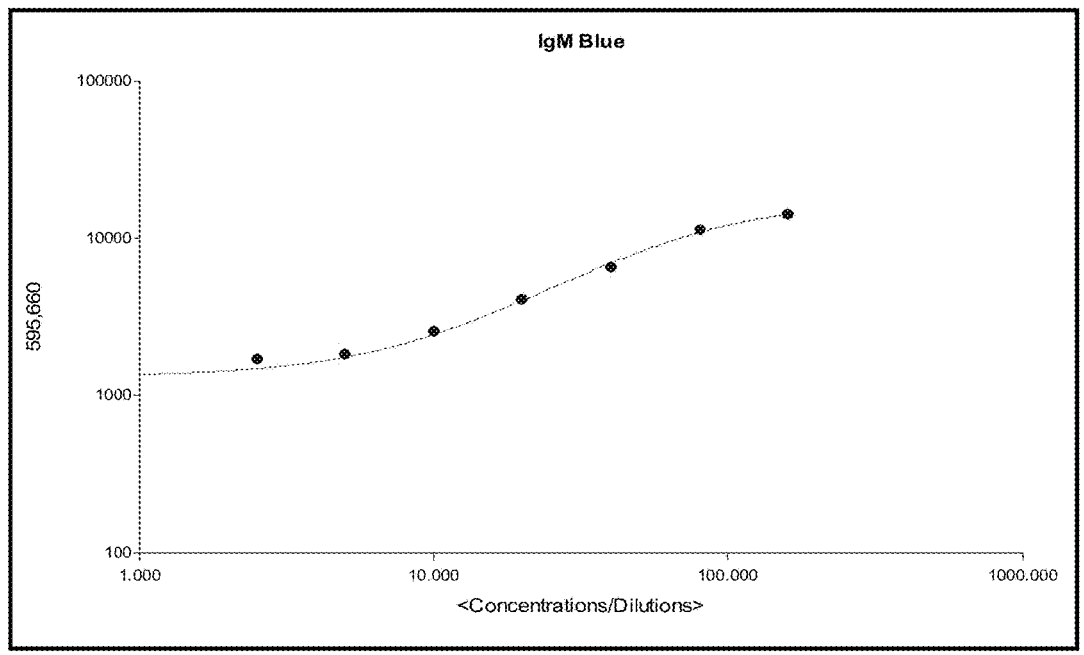
FIG. 56 is a standard curve of autoantibody IgM against human beta 2GP1.
Figure 57:
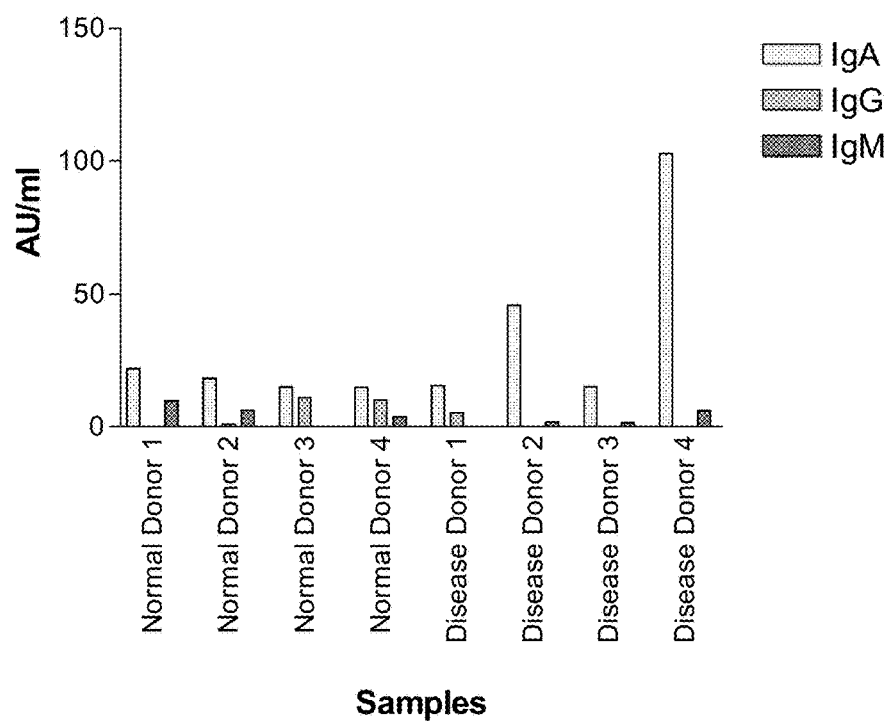
FIG. 57 is a bar graph comparing normal donor and diseased donor IgA, IgG and IgM autoantibody level against beta 2GP1 levels.

The assay standard curves for IgA autoantibody, IgG autoantibody and IgM autoantibody against human beta 2GP1 are shown respectively in FIG. 54, FIG. 55 and FIG. 56. IgA, IgG and IgM levels in samples from normal donors and diseased donors are shown in FIG. 57.

The reference values for the determination of disease state are as follows:
<10.0 U/mL (negative)
10.0-14.9 U/mL (borderline)
>or =15.0 U/mL (positive)

The data indicate that Normal Donor 1 is positive for IgA autoantibody against beta 2GP1 while other normal donors are negative. Disease donor 1 and 3 seems to be normal and disease donor 2 and 4 have strong positive on IgA against beta 2 GP1. The results demonstrate that the multiplex immunoassay can accurately measure IgA, IgG and IgM autoantibody against beta 2GP1.

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

What is claimed is:

1. An immunoassay kit for conducting an immunoassay in a fluorescence plate reader to detect at least two analytes in a sample comprising:
   a solid support;
   a first capture antibody specific for a first analyte;
   a first over-labeled fluorescent probe capable of providing a detectable signal; and
   at least a second capture antibody specific for a second analyte and a second over-labeled fluorescent probe;
   wherein an over-labeled fluorescent probe comprises at least two conjugation moieties and fluorescent moieties, wherein each of the at least two conjugation moieties are labeled with at least two of the fluorescent moieties and are covalently conjugated to the over-labeled fluorescent probe.

2. The immunoassay kit according to claim 1, further comprising n additional capture antibodies, each n additional capture antibody specific for a different analyte, and n additional over-labeled fluorescent probes.

3. The immunoassay kit according to claim 2, wherein the first over-labeled fluorescent probe is specific for the first analyte, the second over-labeled fluorescent probe is specific for the second analyte, and any n additional over-labeled fluorescent probes are each specific for an $n^{th}$ additional analyte.

4. The immunoassay kit according to claim 2, wherein the first over-labeled fluorescent probe is specific for the first capture antibody, the second over-labeled fluorescent probe is specific for the second capture antibody, and any n additional over-labeled fluorescent probes are each specific for an $n^{th}$ capture antibody.

5. The immunoassay kit according to claim 2, wherein the first, second and any n additional capture antibodies are randomly immobilized on the solid support.

6. The immunoassay kit according to claim 1, wherein the fluorescent moieties are selected from the group consisting of Li-COR, CF fluorescent dyes, DyLight Dyes, Alexa Fluor, CY dyes, ATTO, Chromis dyes, R-phycocyanins, allophycocyanin, green fluorescent protein, fluorescent cDNA, and combinations thereof.

7. The immunoassay kit according to claim 6, wherein the fluorescent moieties are selected from the group consisting of DyLight 350, DyLight 405, DyLight 488, DyLight 594, DyLight 633, DyLight 650, ATTO 390, ATTO 565, ATTO, 590, ATTO 430LS, ATTO 490LS, and combinations thereof.

8. The immunoassay kit according to claim 1, wherein each over-labeled fluorescent probe specific for one analyte has a different fluorescent signal from the other over-labeled fluorescent probe specific for other analytes in the sample.

9. The immunoassay kit according to claim 1, wherein each over-labeled fluorescent probe specific for one capture antibody has a different fluorescent signal from the other over-labeled fluorescent probe specific for other capture antibodies.

10. The immunoassay kit according to claim 1, wherein the conjugation moieties are selected from the group consisting of BSA, Ovalbumin (OVA), Keyhole limpet hemocyanin (KLH), SEQ ID NO: 1 (KCKCKCKCKCKCKCK), and combinations thereof.

11. The immunoassay kit according to claim 1, wherein the conjugation moieties are the same for each over-labeled fluorescent probe.

12. The immunoassay kit according to claim 1, wherein the immunoassay has less than about 10% cross-reactivity with any one or more cross-reacting analytes present in the sample.

13. The immunoassay kit according to claim 1, wherein the immunoassay has less than about 5% cross-reactivity with any one or more cross-reacting analytes present in the sample.

14. The immunoassay kit according to claim 1, wherein at least one signal from each over-labeled fluorescent probes is detectable using a fluorescent intensity reader.

15. The immunoassay kit according to according to claim 1, wherein the solid support is selected from the group consisting of a magnetic particle, bead, test tube, microtiter plate, cuvette, membrane, a scaffolding molecule, film, filter paper, disc, and chip.

16. The immunoassay kit according to according to claim 1, wherein at least one analyte is selected from the group consisting of Human alpha1-acid Glycoprotein, Human alpha Fetoprotein, Human alpha1-Microglobulin, Human alpha2-HS-Glycoprotein, Human Adiponectin, Mouse Adiponectin, Rat Adiponectin, Mouse Albumin, Rabbit Albumin, Swine Albumin, Human Pancreatic Amylase, Rat ANP, Human alpha1-antitripsin, Human Apolipoprotein Al, Human ApolipoproteinAII, Human Apolipoprotein B, Human Apolipoprotein CI, Human Apolipoprotein CII, Human Apolipoprotein CIII, Human Apolipoprotein E, Human Apolipoprotein H, Human Antithrombin III, Mouse Antithrombin II, Rat BNP-32, Rat BNP-45, Human Complement C1q, Human Complement C1r, Human Complement C1, Human Complement C2, Human Complement C3, Human Complement C4, Human Complement C5, Human Complement C6, Human Complement C7, Human Complement C8, Human Complement C9, Human Ceruloplasmin, Rat Ceruloplasmin, Human C-Reactive Protein, Rat C-Reactive Protein, Canine C-Reactive Protein, Mouse C-Reactive Protein, Human Elastase (ELA-2), Human Complement Factor B, Human Complement Factor D, Mouse Complement Factor D, Human Complement Factor H, Human Complement Factor I, Human Ferritin, Canine Fibrinogen, Human Fibrinogen, Mouse Fibrinogen, Rat Fibrinogen, Human Fibronectin, Mouse Fibronectin, Human Factor IX, Human Factor V, Human Factor VII, Human Factor X, Human Factor XI, Human Factor XII, Human Factor XIII, Human GC-Globulin, Human GPIIb/IIIa, Bovine Haptoglobulin, Canine Haptoglobulin, Human Haptoglobulin, Swine Haptoglobulin, Rat Haptoglobulin, Human Hemopexin, Human IgA, Human IgD, Human IgG3, Human IgG, Human IgM, Human Kininogen (HMW), Human Lactoferrin, Human Lp(a), Human Lysozyme, Human alpha 2 Macroglobulin, Mouse alpha Macroglobulin, Rat alpha Macroglobulin, Human beta 2-Microglobulin, Rat beta 2-Microglobulin, Human PAI-1, Human PAI-1/tPA, Human Prekallikrein (PK), Bovine Plasminogen, Human Plasminogen, Mouse Plasminogen, Rat Plasminogen, Human Prealbumin, Human Protein C, Human Protein S, Human Protein Z, Human Prothrombin, Swine Prothrombin, Mouse Prothrombin, Human RBP4, Human RBP, Mouse RBP4, Rat RBP4, Canine RBP4, Human Serum Amyloid P, Human TAT Complex, Mouse TAT Complex, Human TF, Human TFPI, Human Thrombin, Human tPA, Human Transferrin, Rat Transferrin, Mouse Transferrin, Human uPA, Human vWF, Human Alpha 1 Antichymotrypsin, Human PSA, Human Total, PSA, Human IgE, Human ApoJ, Human C1qBP, Human Cancer Antigens, Human Cystatin C and combinations thereof.

* * * * *

SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: SYNTHESIZED

<400> SEQUENCE: 1

Lys Cys Lys Cys Lys Cys Lys Cys Lys Cys Lys Cys Lys Cys Lys
1               5                   10                  15